(12) United States Patent
Holyoke, Jr. et al.

(10) Patent No.: US 9,314,025 B2
(45) Date of Patent: *Apr. 19, 2016

(54) MIXTURES OF MESOIONIC PESTICIDES

(71) Applicant: E I DU PONT DE NEMOURS AND COMPANY, Wilmington, DE (US)

(72) Inventors: Caleb William Holyoke, Jr., Newark, DE (US); Wenming Zhang, Newark, DE (US); My-Hanh Thi Tong, Bear, DE (US); Thomas Francis Pahutski, Jr., Elkton, MD (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/184,778

(22) Filed: Feb. 20, 2014

(65) Prior Publication Data

US 2014/0187776 A1    Jul. 3, 2014

Related U.S. Application Data

(63) Continuation of application No. 13/386,190, filed as application No. PCT/US2010/044285 on Aug. 3, 2010, now Pat. No. 8,697,707.

(60) Provisional application No. 61/231,483, filed on Aug. 5, 2009.

(51) Int. Cl.
| | | |
|---|---|---|
| *A01N 43/90* | (2006.01) | |
| *A01N 63/00* | (2006.01) | |
| *A01N 25/00* | (2006.01) | |
| *C07D 471/04* | (2006.01) | |

(52) U.S. Cl.
CPC ..................................... *A01N 43/90* (2013.01)

(58) Field of Classification Search
None
See application file for complete search history.

(56) References Cited

U.S. PATENT DOCUMENTS

| | | | |
|---|---|---|---|
| 5,089,501 | A | 2/1992 | Molleyres |
| 5,151,427 | A | 9/1992 | Holyoke, Jr. et al. |
| 8,552,007 | B2 | 10/2013 | Holyoke, Jr. et al. |
| 2010/0323887 | A1* | 12/2010 | Holyoke et al. ............... 504/100 |
| 2012/0115722 | A1 | 5/2012 | Holyoke, Jr. et al. |
| 2012/0122679 | A1 | 5/2012 | Zhang et al. |
| 2012/0122680 | A1 | 5/2012 | Holyoke, Jr. et al. |
| 2012/0277100 | A1 | 11/2012 | Zhang et al. |
| 2013/0190171 | A1 | 7/2013 | Pahutski, Jr. |
| 2013/0338002 | A1 | 12/2013 | Holyoke, Jr. et al. |

FOREIGN PATENT DOCUMENTS

| | | |
|---|---|---|
| AU | 633661 B2 | 6/1991 |
| EP | 415889 A2 | 3/1991 |

(Continued)

OTHER PUBLICATIONS

Bottcher, A. et al., Journal of Organic Chemistry, vol. 50, No. 25, 1985, pp. 5050-5055.
Urban, R. et al., Helvetica Chimica Acta, vol. 53, No. 5, 1970, pp. 905-922.
Rogers, M. E. et al., Journal of Medicinal Chemistry, vol. 24, No. 11, 1981, pp. 1284-1287.
Glennon, R. A. et al., Journal of Pharmaceutical Sciences, vol. 67, No. 12, 1978, pp. 1762-1765.
Giandinoto, S. et al., Journal of Heterocyclic Chemistry, vol. 33, No. 6, 1996, pp. 1839-1845.
Hellberg, M. et al., Bioorganic and Medicinal Chemistry, vol. 8, No. 8, 2000, pp. 1917-1923.

(Continued)

*Primary Examiner* — Tracy Vivlemore
*Assistant Examiner* — Monica Shin
(74) *Attorney, Agent, or Firm* — Roman Kucharczyk

(57) ABSTRACT

Disclosed are compositions comprising (a) at least one compound selected from compounds of Formula 1, N-oxides, and salt thereof,
wherein
  $R^1$ is phenyl optionally substituted with up to 5 substituents independently selected from $R^3$, or pyridinyl optionally substituted with up to 4 substituents independently selected from $R^3$;
  $R^2$ is $C_1$-$C_4$ haloalkyl; or thiazolyl, pyridinyl or pyrimidinyl, each optionally substituted with up to 2 substituents independently selected from the group consisting of halogen and $C_1$-$C_4$ alkyl;
  each $R^3$ is independently halogen, cyano, $C_1$-$C_4$ alkyl, $C_1$-$C_4$ haloalkyl, $C_1$-$C_4$ alkoxy, $C_1$-$C_4$ haloalkoxy, $C(R^4)$=$NOR^4$ or Q;
  each $R^4$ is independently $C_1$-$C_4$ alkyl;
  Z is CH=CH or S; and
  each Q is independently phenyl or pyridinyl, each optionally substituted with up to 3 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy; and
  (b) at least one invertebrate pest control agent.
Also disclosed are methods for controlling an invertebrate pest comprising contacting the invertebrate pest or its environment with a biologically effective amount of a composition of the invention.

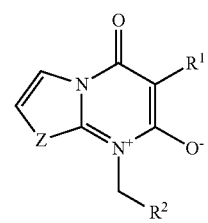

1 Claim, No Drawings

(56) References Cited

FOREIGN PATENT DOCUMENTS

| EP | 430883 A2 | 6/1991 |
|---|---|---|
| EP | 430885 A2 | 6/1991 |
| WO | 2012106495 A1 | 8/2012 |

OTHER PUBLICATIONS

Glennon, R. A. et al., Journal of Heterocyclic Chemistry, vol. 17, No. 2, 1980, pp. 337-340.
Coburn, R. A. et al., Journal of Heterocyclic Chemistry, vol. 10, No. 4, 1973, pp. 487-494.
Schubert, E. M. et al., Journal of Heterocyclic Chemistry, vol. 22, No. 3, 1985, pp. 889-905.
Kappe, T., Encyclopedia of Reagents for Organic Synthesis, 2001, no page number available (carbon suboxide entry), John Wiley & Sons, Ltd.
Cesar, V. et al., Journal of the American Chemical Society, vol. 130, No. 34, 2008, pp. 11286-11287.
Jonas, U. et al., Tetrahedron, vol. 60, No. 44, 2004, pp. 10011-10018.
Ritter, H. et al., Macromolecules, vol. 36, No. 20, 2003, pp. 7520-7526.
Ritter, H. et al., Macromolecules, vol. 36, No. 20, 2003, pp. 7552-7559.
Ritter, H. et al., Macromolecular Chemistry and Physics, vol. 204, No. 10, 2003, pp. 1297-1304.
Ritter, H. et al., Macromolecular Chemistry and Physics, vol. 204, No. 8, 2003, pp. 1079-1084.
Ritter, H. et al., Designed Monomers and Polymers, vol. 4, No. 2, 2001, pp. 177-194.
Wentrup, C. et al., Journal of the Chemical Society, Perkin Trans. 2, No. 10, 2000, pp. 2096-2108.
Ritter, H. et al., Macromolecular Chemistry and Physics, vol. 201, No. 11, 2000, pp. 1200-1205.
Issac, Y., Bulletin of the Chemical Society of Japan, vol. 72, No. 3, 1999, pp. 503-509.
Ritter, H. et al., Macromolecular Rapid Communications, vol. 17, No. 10, 1996, pp. 723-730.
Ritter, H. et al., Macromolecular Rapid Communications, vol. 16, No. 6, 1995, pp. 407-415.
Kappe, T. et al., Heterocycles, vol. 40, No. 2, 1995, pp. 681-689.
Ritter, H. et al., Macromolecular Chemistry and Physics, vol. 195, No. 12, 1994, pp. 3823-3824.
Kappe, T. et al., Archiv der Pharmazie (Weinheim), vol. 324, No. 11, 1991, pp. 863-866.
Gotthardt, H. et al., Chemische Berichte, vol. 121, No. 6, 1988, pp. 1143-1146.
Gotthardt, H. et al., Chemische Berichte, vol. 119, No. 4, 1986, pp. 1315-1330.
Gotthardt, H. et al., Chemische Berichte, vol. 118, No. 11, 1985, pp. 4567-4577.
Gotthardt, H. et al., Chemische Berichte, vol. 118, No. 11, 1985, pp. 4578-4587.
Friedrichsen, W. et al., Zeitschrift fuer Naturforschung, vol. 37b2, 1982, pp. 222-233.
Friedrichsen, W. et al., Liebigs Annalen der Chemie, No. 3, 1981, pp. 521-531.
Moore, H. et al., Journal of the American Chemical Society, vol. 103, No. 7, 1981, pp. 1769-1777.
Kappe, T. et al., Chemische Berichte, vol. 112, No. 5, 1979, pp. 1584-1594.
Moore, H. et al., Heterocycles, vol. 12, No. 1, 1979, pp. 45-49.
Friedrichsen, W. et al., Liebigs Annalen der Chemie, No. 10, 1978, pp. 1655-1665.
Ziegler, E. et al., Zeitschrift fuer Naturforschung, vol. 32b, No. 10, 1977, pp. 1204-1208.
Huhn, M. et al., Tetrahedron, vol. 32, No. 17, 1976, pp. 2117-2120.
Kappe, T. et al., Chemische Berichte, vol. 109, No. 11, 1985, pp. 3668-3674.
Kappe, T. et al., Synthesis, No. 4, 1975, pp. 247-249.
Maki, Y. et al., Journal of the Chemical Society, Chemical Communications, No. 17, 1972, pp. 999-1000.
Kotarska, A. et al., Societatis Scientiarum Lodziensis, Acta Chimica, vol. 16, 1971, pp. 89-93.
Potts, K. et al., Journal of Organic Chemistry, vol. 37, No. 9, 1972, pp. 1422-1425.
Kappe, T. et al., Monatshefte fur Chemie, vol. 102, No. 3, 1971, pp. 781-787.
Kappe, T. et al., Monatshefte fur Chemie, vol. 102, No. 2, 1971, pp. 412-424.
Potts, K. et al., Journal of Organic Chemistry, vol. 36, No. 1, 1971, pp. 8-10.
Berre, A. et al., Bulletin de la Societe Chimique de France, vol. 9, 1969, pp. 3133-3138.
Ingalls, E. et al., Journal of Heterocyclic Chemistry, vol. 4, No. 4, 1967, pp. 523-526.
Prystas, M., Collection of Czechoslovak Chemical Communications, vol. 32, No. 12, 1967, pp. 4241-4259.
Prystas, M. et al., Collection of Czechoslovak Chemical Communications, vol. 32, No. 3, 1967, pp. 1298-1304.
Kheifets, G. et al., Doklady Akademii Nauk SSSR, vol. 166, No. 3, 1966, pp. 635-638.
Katritzky, A. et al., Journal of the Chemical Society, 1962, pp. 1544-1548.
Kheifets, G. et al., Zhurnal Organicheskoi Khimii, vol. 2, No. 8, 1966, pp. 1497-1502.
Glennon, R. et al., Journal of Medicinal Chemistry, vol. 27, 1984, pp. 1364-1367.
Glennon, R. et al., Journal of Medicinal Chemistry, vol. 24, 1981, pp. 658-661.
Bass, R. et al., Journal of Heterocyclic Chemistry, vol. 22, 1985, pp. 465-474.
Bass, R. et al., Organic Magnetic Resonance, vol. 21, No. 9, 1983, pp. 527-531.
Friedrichsen, W. et al., Heterocycles, vol. 19, No. 6, 1982, pp. 1083-1113.
XP002628604 (Gotthardt, H. et al., Chemische Berichte, vol. 120, No. 1, 1987, pp. 109-114).
XP002628606 (Katritzky, A. et al., Journal of the Chemical Society, 1962, pp. 1540-1544).
XP002628608 (Stoelting, D. et al., Journal of Heterocyclic Chemistry, vol. 39, No. 4, 2002, pp. 719-725).
XP002628612 (Prabhakar, Y. et al., Journal of Pharmacobio-Dynamics, vol. 7, No. 6, 1984, pp. 366-371).
XP002628614 (Coburn, R. et al., Journal of Heterocyclic Chemistry, vol. 10, No. 4, 1973, pp. 479-485).
XP002628617 (Siddiqi, S. et al., Nucleosides & Nucleotides, vol. 15, Nos. 1-3, 1996, pp. 693-717).
XP002628619 (Schindler, G. et al., Zeitschrift fuer Naturforschung, Teil B, vol. 31 B, No. 4, 1976, pp. 500-504).
XP002628622 (Szargan, R. et al., Recent Adv. Anal. Spectrosc., Proc. Int. Conf. At. Spectroscs., 9th, 1982 (Meeting date 1981), pp. 175-184).
XP002628623 (Gotthardt, H. et al., Chemische Berichte, vol. 118, No. 5, 1985, pp. 2079-2094).
XP002628625 (Rickborn, B., Organic Reactions, vol. 53, 1998, no pages given).
XP002628626 (Kappe, T. et al., Heterocycles, vol. 40, No. 2, pp. 681-689), 1995.
U.S. Appl. No. 13/386,065 Office Action dated Aug. 14, 2013.
U.S. Appl. No. 13/386,065 Interview Summary dated Oct. 23, 2013.
U.S. Appl. No. 13/386,160 Office Action dated Apr. 10, 2013.
U.S. Appl. No. 13/967,629 Office Action dated Jan. 21, 2014.

* cited by examiner

MIXTURES OF MESOIONIC PESTICIDES

This application is a continuation of application Ser. No. 13/386,160, filed Jan. 20, 2012, which is a national stage entry of PCT/US2010/44285, filed Aug. 3, 2010. PCT/US2010/44285 claims priority benefit from Provisional Application 61/231,483, filed Aug. 5, 2009.

FIELD OF THE INVENTION

This invention relates to pesticidal mixtures comprising certain pyrimidinium compounds, their N-oxides, and salts, and at least one other invertebrate pest control agent, suitable for agronomic, nonagronomic and animal health uses, and methods of their use for controlling invertebrate pests such as arthropods in both agronomic and nonagronomic environments, and for treatment of parasite infections in animals or infestations in the general environment.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public health is also important. Many products are commercially available for these purposes, but the need continues for new compounds that are more effective, less costly, less toxic, environmentally safer or have different sites of action.

The control of animal parasites in animal health is essential, especially in the areas of food production and companion animals. Existing methods of treatment and parasite control are being compromised due to growing resistance to many current commercial parasiticides. The discovery of more effective ways to control animal parasites is therefore imperative.

U.S. Pat. No. 5,151,427 discloses mesoionic pyrimidinium compounds of Formula i as anthelmintics

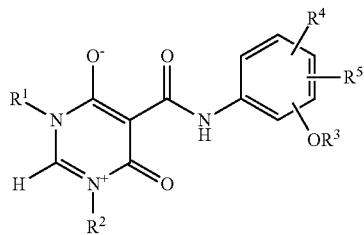

i wherein, inter alia, $R^1$ and $R^2$ are independently $C_1$-$C_6$ alkyl, $R^3$ is a heteroaromatic 6-membered ring, and $R^4$ and $R^5$ are independently hydrogen or $C_1$-$C_4$ alkyl.

The mixtures of the present invention are not disclosed in this publication.

SUMMARY OF THE INVENTION

This invention is directed to a composition comprising (a) at least one compound selected from compounds of Formula 1 (including all stereoisomers), N-oxides, and salts thereof,

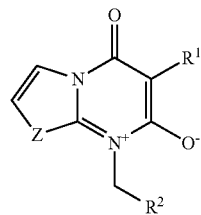

1 wherein
 $R^1$ is phenyl optionally substituted with up to 5 substituents independently selected from $R^3$, or pyridinyl optionally substituted with up to 4 substituents independently selected from $R^3$;
 $R^2$ is $C_1$-$C_4$ haloalkyl; or thiazolyl, pyridinyl or pyrimidinyl, each optionally substituted with up to 2 substituents independently selected from the group consisting of halogen and $C_1$-$C_4$ alkyl;
 each $R^3$ is independently halogen, cyano, $C_1$-$C_4$ alkyl, $C_1$-$C_4$ haloalkyl, $C_1$-$C_4$ alkoxy, $C_1$-$C_4$ haloalkoxy, $C(R^4)$=$NOR^4$ or Q;
 each $R^4$ is independently $C_1$-$C_4$ alkyl;
 Z is CH=CH or S; and
 each Q is independently phenyl or pyridinyl, each optionally substituted with up to 3 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy;
and
(b) at least one invertebrate pest control agent selected from the group consisting of abamectin, acetamiprid, amitraz, avermectin, azadirachtin, bensultap, bifenthrin, buprofezin, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, fenothiocarb, fenoxycarb, fenvalerate, fipronil, flonicamid, flubendiamide, flufenoxuron, hexaflumuron, hydramethylnon, imidacloprid, indoxacarb, lufenuron, metaflumizone, methomyl, methoprene, methoxyfenozide, nitenpyram, nithiazine, novaluron, oxamyl, phosmet, pymetrozine, pyrethrin, pyridaben, pyridalyl, pyriproxyfen, ryanodine, spinetoram, spinosad, spirodiclofen, spiromesifen, spirotetramat, tebufenozide, thiacloprid, thiamethoxam, thiodicarb, thiosultap-sodium, tolfenpyrad, tralomethrin, triazamate, triflumuron, *Bacillus thuringiensis* delta-endotoxins, all strains of *Bacillus thuringiensis* and all strains of nucleo polyhedrosis viruses.

This invention is also directed to aforesaid composition wherein component (a) is selected from at least one compound of Formula 1 (including all stereoisomers).

This invention is also directed to the compositions described above, and further herein, provided that (a) when $R^1$ is unsubstituted phenyl and $R^2$ is $CF_3$, then Z is S; (b) when $R^1$ is 2-fluorophenyl and $R^2$ is 2-chloro-5-thiazolyl, then Z is S; and (c) when $R^1$ is 2-fluorophenyl or 3-(trifluoromethoxy) phenyl and $R^2$ is 6-chloro-3-pyridinyl, then Z is CH=CH.

This invention also provides a composition comprising any of the compositions described above and at least one additional component selected from the group consisting of surfactants, solid diluents and liquid diluents. In one embodiment, this invention also provides a composition for controlling an invertebrate pest comprising the composition described above and at least one additional component selected from the group consisting of surfactants, solid diluents and liquid diluents, said composition further comprising at least one additional biologically active compound or agent.

This invention is also directed to a composition comprising (a) at least one compound selected from compounds of Formula 1, N-oxides, and salts thereof,

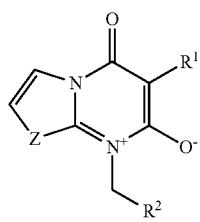

1 wherein
R$^1$ is phenyl optionally substituted with up to 5 substituents independently selected from R$^3$, or pyridinyl optionally substituted with up to 4 substituents independently selected from R$^3$;
R$^2$ is C$_1$-C$_4$ haloalkyl; or thiazolyl, pyridinyl or pyrimidinyl, each optionally substituted with up to 2 substituents independently selected from the group consisting of halogen and C$_1$-C$_4$ alkyl;
each R$^3$ is independently halogen, cyano, C$_1$-C$_4$ alkyl, C$_1$-C$_4$ haloalkyl, C$_1$-C$_4$ alkoxy, C$_1$-C$_4$ haloalkoxy, C(R$^4$)=NOR$^4$ or Q;
each R$^4$ is independently C$_1$-C$_4$ alkyl;
Z is CH=CH or S; and
each Q is independently phenyl or pyridinyl, each optionally substituted with up to 3 substituents independently selected from the group consisting of halogen, cyano, C$_1$-C$_4$ alkyl, C$_1$-C$_4$ haloalkyl, C$_1$-C$_4$ alkoxy and C$_1$-C$_4$ haloalkoxy;
and at least one additional biologically active compound or agent selected from the group consisting of
(b) at least one invertebrate pest control agent selected from the group consisting of abamectin, acetamiprid, amitraz, avermectin, azadirachtin, bensultap, bifenthrin, buprofezin, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, fenothiocarb, fenoxycarb, fenvalerate, fipronil, flonicamid, flubendiamide, flufenoxuron, hexaflumuron, hydramethylnon, imidacloprid, indoxacarb, lufenuron, metaflumizone, methomyl, methoprene, methoxyfenozide, nitenpyram, nithiazine, novaluron, oxamyl, phosmet, pymetrozine, pyrethrin, pyridaben, pyridalyl, pyriproxyfen, ryanodine, spinetoram, spinosad, spirodiclofen, spiromesifen, spirotetramat, tebufenozide, thiacloprid, thiamethoxam, thiodicarb, thiosultap-sodium, tolfenpyrad, tralomethrin, triazamate, triflumuron, *Bacillus thuringiensis* delta-endotoxins, all strains of *Bacillus thuringiensis* and all strains of nucleo polyhedrosis viruses; and
(c) at least one fungicide;

provided that when the at least one additional biologically active compound or agent is selected from group (b) and (i) when R$^1$ is unsubstituted phenyl and R$^2$ is CF$_3$, then Z is S; (ii) when R$^1$ is 2-fluorophenyl and R$^2$ is 2-chloro-5-thiazolyl, then Z is S; and (iii) when R$^1$ is 2-fluorophenyl or 3-(trifluoromethoxy)phenyl and R$^2$ is 6-chloro-3-pyridinyl, then Z is CH=CH.

This invention further provides a composition for protecting an animal from an invertebrate parasitic pest comprising any of the compositions described above and at least one carrier.

This invention provides a method for controlling an invertebrate pest comprising contacting the invertebrate pest or its environment with a biologically effective amount of any of the aforesaid compositions.

This invention also provides a method for controlling an invertebrate pest comprising contacting the invertebrate pest or its environment with a biologically effective amount of any of the aforesaid compositions wherein the environment is a plant.

This invention also provides a method for controlling an invertebrate pest comprising contacting the invertebrate pest or its environment with a biologically effective amount of any of the aforesaid compositions wherein the environment is an animal.

This invention also provides a method for controlling an invertebrate pest comprising contacting the invertebrate pest or its environment with a biologically effective amount of any of the aforesaid compositions wherein the environment is a seed.

This invention also provides a method for controlling an invertebrate pest comprising contacting the invertebrate pest or its environment with a biologically effective amount of any of the aforesaid compositions wherein the environment is a seed coated with the aforesaid compositions comprising the compound of claim 1 and optionally a film former or adhesive agent.

This invention also provides a method for protecting a seed from an invertebrate pest comprising contacting the seed with any of the compositions described above. This invention also relates to the treated seed.

This invention further provides a method for treating, preventing, inhibiting and/or killing ecto and/or endoparasites comprising administering to and/or on an animal a parasiticidally effective amount of any of the compositions described above. This invention also relates to such method wherein a parasiticidally effective amount of any of the compositions described above is administered to an environment (e.g., a stall or blanket) in which an animal resides.

This invention is also directed to compounds of Formula 1 selected from the group consisting of:
3-(2-chloro-6-fluorophenyl)-1-[(6-chloro-3-pyridinyl)methyl]-2-hydroxy-4-oxo-4H-pyrido[1,2-a]pyrimidinium inner salt;
1-[(2-chloro-5-thiazolyl)methyl]-3-(2-ethoxyphenyl)-2-hydroxy-4-oxo-4H-pyrido[1,2-a]pyrimidinium inner salt;
1-[(2-chloro-5-thiazolyl)methyl]-2-hydroxy-3-(3-methylphenyl)-4-oxo-4H-pyrido[1,2-a]pyrimidinium inner salt;
3-(3-chloro-2-fluorophenyl)-1-[(6-chloro-3-pyridinyl)methyl]-2-hydroxy-4-oxo-4H-pyrido[1,2-a]pyrimidinium inner salt;
2-hydroxy-4-oxo-1-(5-pyrimidinylmethyl)-3-[3-(trifluoromethyl)phenyl]-4H-pyrido[1,2-a]pyrimidinium inner salt;

1-[(2-chloro-5-thiazolyl)methyl]-2-hydroxy-4-oxo-3-(4'-(trifluoromethyl)[1,1'-biphenyl]-3-yl)-4H-pyrido[1,2-a]pyrimidinium inner salt;

1-[(2-chloro-5-thiazolyl)methyl]-3-(4'-fluoro[1,1'-biphenyl]-3-yl)-2-hydroxy-4-oxo-4H-pyrido[1,2-a]pyrimidinium inner salt; and 3-(5-chloro-2-fluorophenyl)-1-[(6-fluoro-3-pyridinyl)methyl]-2-hydroxy-4-oxo-4H-pyrido[1,2-a]pyrimidinium inner salt.

DETAILS OF THE INVENTION

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" refers to a living organism of the Phylum Nematoda. The term "helminths" includes roundworms, heartworms, and phytophagous nematodes (Nematoda), flukes (Tematoda), Acanthocephala, and tapeworms (Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from an invertebrate parasitic pest by administering a parasiticidally effective (i.e. biologically effective) amount of a compound of the invention, typically in the form of a composition formulated for veterinary use, to the animal to be protected. As referred to in the present disclosure and claims, the terms "parasiticidal" and "parasiticidally" refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal.

In the above recitations, the term "alkyl", used either alone or in compound words such as "haloalkyl" includes straight-chain or branched alkyl, such as, methyl, ethyl, n-propyl, i-propyl, or the different butyl isomers.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $CF_3$, $CH_2Cl$, $CH_2CF_3$ and $CCl_2CF_3$.

"Alkoxy" includes, for example, methoxy, ethoxy, n-propyloxy, isopropyloxy and the different butoxy isomers. "Haloalkoxy" is defined similarly to "haloalkyl"; examples of "haloalkoxy" include $OCF_3$, $OCH_2Cl$, $OCH_2CF_3$ and $OCCl_2CF_3$.

The $R^3$ substituent $C(R^4)=NOR^4$ represents an oxime having either of the two regioisomeric structures shown below.

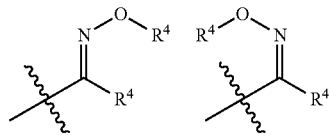

The total number of carbon atoms in a substituent group is indicated by the "$C_i$-$C_j$" prefix where i and j are numbers from 1 to 4. For example, $C_1$-$C_4$ alkyl designates methyl through butyl.

When a radical (e.g., phenyl or pyridinyl in the definition of $R^1$) is optionally substituted with listed substituents with the number of substituents stated (e.g., "up to 5"), then the radical may be unsubstituted or substituted with a number of substituents ranging up to the high number stated (e.g., "5"), and the attached substituents are independently selected from the substituents listed.

The term "unsubstituted" in connection with a group such as a ring means the group does not have any substituents other than its one or more attachments to the remainder of Formula 1. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 3.

The number of optional substituents may be restricted by an expressed limitation. For example, the phrase "optionally substituted with up to 5 substituents" means that 0, 1, 2, 3, 4 or 5 substituents can be present (if the number of potential connection points allows). When a range specified for the number of substituents exceeds the number of positions available for substituents on a ring, the actual higher end of the range is recognized to be the number of available positions.

A wide variety of synthetic methods are known in the art to enable preparation of aromatic heterocyclic rings; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

The compounds of Formula 1 are mesoionic inner salts. "Inner salts", also known in the art as "zwitterions", are electrically neutral molecules but carry formal positive and negative charges on different atoms in each valence bond structure according to valence bond theory. Furthermore the molecular structure of the compounds of Formula 1 can be represented by the six valence bond structures shown below, each placing the formal positive and negative charges on different atoms. Because of this resonance, the compounds of Formula 1 are also described as "mesoionic". Although for sake of simplicity, the molecular structure of Formula 1 is depicted as a single valence bond structure herein, this particular valence bond structure is to be understood as representative of all six valence bond structures relevant to bonding in molecules of compounds of Formula 1. Therefore reference to Formula 1 herein relates to all six applicable valence bond structures and other (e.g., molecular orbital theory) structures unless otherwise specified.

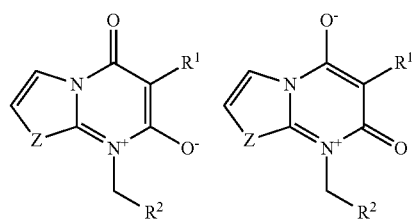

1

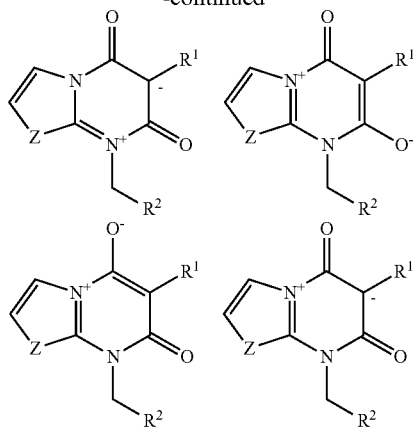

Compounds of Formula 1 can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of Formula 1 can exist as one or more conformational isomers due to restricted bond rotation caused by steric hinderance. For example, a compound of Formula 1 wherein $R^1$ is phenyl substituted in the ortho-position with a sterically demanding alkyl group (e.g., isopropyl) may exist as two rotamers due to restricted rotation about the $R^1$-pyrimidinium ring bond. This invention comprises mixtures of conformational isomers. In addition, this invention comprises compounds that are enriched in one conformer relative to others.

Compounds selected from Formula 1, (including all stereoisomers, N-oxides, and salts thereof), typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. Synthetic methods for the preparation of N-oxides of heterocycles are very well known by one skilled in the art including the oxidation of heterocycles with peroxy acids such as peracetic and 3-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding non-salt forms, salts share the biological utility of the nonsalt forms. Thus a wide variety of salts of the compounds of Formula 1 are useful for control of invertebrate pests and animal parasites (i.e. are suitable for animal health use). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. Accordingly, the present invention comprises compounds selected from Formula 1, N-oxides and salts thereof.

Embodiments of the present invention as described in the Summary of the Invention include those described below. In the following Embodiments Formula 1 includes stereoisomers, N-oxides, and salts thereof, and reference to "a compound of Formula 1" includes the definitions of substituents specified in the Summary of the Invention unless further defined in the Embodiments.

Embodiment 1

The composition described in the Summary of the Invention wherein component (a) is a compound of Formula 1 wherein $R^1$ is phenyl optionally substituted with up to 3 substituents independently selected from $R^3$, or pyridinyl optionally substituted with up to 2 substituents independently selected from $R^3$.

Embodiment 2

The composition of Embodiment 1 wherein $R^1$ is phenyl optionally substituted with up to 3 substituents independently selected from $R^3$.

Embodiment 2a

The composition of Embodiment 2 wherein $R^1$ is phenyl substituted with 1, 2 or 3 substituents independently selected from $R^3$.

Embodiment 2b

The composition of Embodiment 2a wherein $R^1$ is phenyl substituted with 1, 2 or 3 substituents independently selected from $R^3$ other than Q.

Embodiment 2c

The composition of Embodiment 2a wherein $R^1$ is phenyl substituted with one substituent selected from Q and optionally up to 2 substituents independently selected from $R^3$ other than Q.

Embodiment 2d

The composition of Embodiment 2c wherein Q is phenyl optionally substituted with up to 3 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

Embodiment 2e

The composition of Embodiment 2c wherein Q is pyridinyl optionally substituted with up to 3 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

Embodiment 2f

The composition of Embodiment 2d wherein Q is phenyl optionally substituted with up to 3 substituents independently selected from the group consisting of halogen and $C_1$-$C_4$ haloalkyl.

Embodiment 2g

The composition of Embodiment 2e wherein Q is pyridinyl optionally substituted with up to 3 substituents independently selected from the group consisting of halogen and $C_1$-$C_4$ haloalkyl.

Embodiment 3

The composition of Embodiment 1 wherein $R^1$ is pyridinyl optionally substituted with up to 2 substituents independently selected from $R^3$.

Embodiment 3a

The composition of Embodiment 3 wherein $R^1$ is pyridinyl substituted with up to 2 substituents independently selected from $R^3$.

Embodiment 3b

The composition of Embodiment 3a wherein $R^1$ is pyridinyl substituted with up to 2 substituents independently selected from $R^3$ other than Q.

Embodiment 3c

The composition of Embodiment 3a wherein $R^1$ is pyridinyl substituted with one substituent selected from Q and optionally one substituent selected from $R^3$ other than Q.

Embodiment 3d

The composition of Embodiment 3c wherein Q is phenyl optionally substituted with up to 3 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

Embodiment 3e

The composition of Embodiment 3c wherein Q is pyridinyl optionally substituted with up to 3 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

Embodiment 3f

The composition of Embodiment 3d wherein Q is phenyl optionally substituted with up to 3 substituents independently selected from the group consisting of halogen or $C_1$-$C_4$ haloalkyl.

Embodiment 3g

The composition of Embodiment 3e wherein Q is pyridinyl optionally substituted with up to 3 substituents independently selected from the group consisting of halogen or $C_1$-$C_4$ haloalkyl.

Embodiment 3h

The composition of Embodiment 3 wherein each $R^3$ is independently halogen, $C_1$-$C_2$ alkyl, $C_1$-$C_2$ haloalkyl, $C_1$-$C_2$ alkoxy, $C_1$-$C_2$ haloalkoxy or Q.

Embodiment 3i

The composition of Embodiment 3h wherein each $R^3$ is independently halogen or $C_1$-$C_2$ haloalkyl.

Embodiment 4

The composition described in the Summary of the Invention or any of Embodiments 1 to 3g wherein each $R^3$ is independently halogen, $C_1$-$C_2$ alkyl, $C_1$-$C_2$ haloalkyl, $C_1$-$C_2$ alkoxy or $C_1$-$C_2$ haloalkoxy.

Embodiment 4a

The composition of Embodiment 4 wherein each $R^3$ is independently halogen or $C_1$-$C_2$ haloalkyl.

Embodiment 4b

The composition of Embodiment 4a wherein each $R^3$ is independently halogen.

Embodiment 5

The composition described in the Summary of the Invention or any of Embodiments 1 to 4b wherein component (a) is a compound of Formula 1 wherein $R^2$ is $C_1$-$C_4$ haloalkyl.

Embodiment 5a

The composition of Embodiment 5 wherein $R^2$ is $C_1$-$C_2$ haloalkyl.

Embodiment 5b

The composition of Embodiment 5a wherein $R^2$ is $CH_2CF_3$.

Embodiment 6

The composition described in the Summary of the Invention or any of Embodiments 1 to 4b wherein component (a) is a compound of Formula 1 wherein $R^2$ is thiazolyl, pyridinyl or pyrimidinyl, each optionally substituted with up to 2 substituents independently selected from the group consisting of halogen and $C_1$-$C_4$ alkyl.

Embodiment 6a

The composition described in the Summary of the Invention or any of Embodiments 1 to 4b wherein component (a) is a compound of Formula 1 wherein $R^2$ is thiazolyl optionally substituted with up to 2 substituents independently selected from the group consisting of halogen and $C_1$-$C_4$ alkyl.

Embodiment 6b

The composition of Embodiment 6a wherein $R^2$ is thiazolyl optionally substituted with up to 2 substituents independently selected from halogen.

Embodiment 6c

The composition of Embodiment 6b wherein $R^2$ is thiazolyl optionally substituted with Cl.

Embodiment 6d

The composition of Embodiment 6c wherein $R^2$ is 2-chloro-5-thiazolyl.

Embodiment 7

The composition described in the Summary of the Invention or any of Embodiments 1 to 4b wherein component (a) is a compound of Formula 1 wherein $R^2$ is pyridinyl optionally substituted with up to 2 substituents independently selected from the group consisting of halogen and $C_1$-$C_4$ alkyl.

Embodiment 7a

The composition of Embodiment 7 wherein $R^2$ is pyridinyl optionally substituted with up to 2 substituents independently selected from halogen.

Embodiment 7b

The composition of Embodiment 7a wherein $R^2$ is pyridinyl optionally substituted with Cl.

Embodiment 7c

The composition of Embodiment 7b wherein $R^2$ is 6-chloro-3-pyridinyl.

Embodiment 8

The composition described in the Summary of the Invention or any of Embodiments 1 to 4b wherein component (a) is a compound of Formula 1 wherein $R^2$ is pyrimidinyl optionally substituted with up to 2 substituents independently selected from the group consisting of halogen and $C_1$-$C_4$ alkyl.

Embodiment 8a

The composition of Embodiment 8 wherein $R^2$ is pyrimidinyl optionally substituted with $C_1$-$C_4$ alkyl.

Embodiment 8b

The composition of Embodiment 8a wherein $R^2$ is pyrimidinyl optionally substituted with $CH_3$.

Embodiment 8c

The composition of Embodiment 8b wherein $R^2$ is 2-methyl-5-pyrimidinyl.

Embodiment 8d

The composition of Embodiment 8b wherein $R^2$ is 5-pyrimidinyl.

Embodiment 9

The composition described in the Summary of the Invention or any of Embodiments 1 to 8d wherein component (a) is a compound of Formula 1 wherein Z is CH=CH.

Embodiment 10

The composition described in the Summary of the Invention or any of Embodiments 1 to 8d wherein component (a) is a compound of Formula 1 wherein Z is S.

Embodiments of this invention, including Embodiments 1-10 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-10 above as well as any other embodiments described herein, and any combination thereof, pertain to the compositions and methods of the present invention.

Specific embodiments include the compositions described in the Summary of the Invention wherein component (a) is a compound of Formula 1 selected from the group consisting of:
1-[(2-chloro-5-thiazolyl)methyl]-3-(2,6-difluorophenyl)-2-hydroxy-4-oxo-4H-pyrido[1,2-a]pyrimidinium inner salt;
1-[(2-chloro-5-thiazolyl)methyl]-3-(2,6-dimethoxyphenyl)-2-hydroxy-4-oxo-4H-pyrido[1,2-a]pyrimidinium inner salt;
1-[(2-chloro-5-thiazolyl)methyl]-2-hydroxy-3-(2-methoxyphenyl)-4-oxo-4H-pyrido[1,2-a]pyrimidinium inner salt;
3-(3,5-dimethoxyphenyl)-1-[(6-fluoro-3-pyridinyl)methyl]-2-hydroxy-4-oxo-4H-pyrido[1,2-a]pyrimidinium inner salt;
1-[(6-fluoro-3-pyridinyl)methyl]-2-hydroxy-4-oxo-3-[3-(trifluoromethyl)phenyl]-4H-pyrido[1,2-a]pyrimidinium inner salt;
1-[(6-chloro-3-pyridinyl)methyl]-3-(2-fluoro-3-methoxyphenyl)-2-hydroxy-4-oxo-4H-pyrido[1,2-a]pyrimidinium inner salt;
3-(4-fluorophenyl)-2-hydroxy-1-[(2-methyl-5-thiazolyl)methyl]-4-oxo-4H-pyrido[1,2-a]pyrimidinium inner salt;
2-hydroxy-4-oxo-3-phenyl-1-(5-thiazolylmethyl)-4H-pyrido[1,2-a]pyrimidinium inner salt;
3-(2-fluorophenyl)-1-[(6-fluoro-3-pyridinyl)methyl]-2-hydroxy-4-oxo-4H-pyrido[1,2-a]pyrimidinium inner salt;
1-[(6-fluoro-3-pyridinyl)methyl]-2-hydroxy-4-oxo-3-[3-(trifluoromethoxy)phenyl]-4H-pyrido[1,2-a]pyrimidinium inner salt;
3-(5-bromo-2-methoxyphenyl)-1-[(6-chloro-3-pyridinyl)methyl]-2-hydroxy-4-oxo-4H-pyrido[1,2-a]pyrimidinium inner salt;
1-[(6-chloro-3-pyridinyl)methyl]-3-[2-chloro-5-(trifluoromethyl)phenyl]-2-hydroxy-4-oxo-4H-pyrido[1,2-a]pyrimidinium inner salt;
1-[(6-fluoro-3-pyridinyl)methyl]-3-[2-fluoro-3-(trifluoromethyl)phenyl]-2-hydroxy-4-oxo-4H-pyrido[1,2-a]pyrimidinium inner salt;
1-[(2-chloro-5-thiazolyl)methyl]-3-[3-(6-fluoro-3-pyridinyl)-5-(trifluoromethoxy)phenyl]-2-hydroxy-4-oxo-4H-pyrido[1,2-a]pyrimidinium inner salt;
1-[(2-chloro-5-thiazolyl)methyl]-3-[3-chloro-5-(trifluoromethoxy)phenyl]-2-hydroxy-4-oxo-4H-pyrido[1,2-a]pyrimidinium inner salt;
1-[(2-chloro-5-thiazolyl)methyl]-3-[3-chloro-5-(trifluoromethyl)phenyl]-2-hydroxy-4-oxo-4H-pyrido[1,2-a]pyrimidinium inner salt;
1-[(6-chloro-3-pyridinyl)methyl]-2-hydroxy-4-oxo-3-(2,3,6-trifluorophenyl)-4H-pyrido[1,2-a]pyrimidinium inner salt;
3-(3-chloro-2,6-difluorophenyl)-1-[(6-chloro-3-pyridinyl)methyl]-2-hydroxy-4-oxo-4H-pyrido[1,2-a]pyrimidinium inner salt;
3-(2,3-difluorophenyl)-1-[(6-fluoro-3-pyridinyl)methyl]-2-hydroxy-4-oxo-4H-pyrido[1,2-a]pyrimidinium inner salt;
3-(5-chloro-2-methoxyphenyl)-1-[(6-fluoro-3-pyridinyl)methyl]-2-hydroxy-4-oxo-4H-pyrido[1,2-a]pyrimidinium inner salt;
3-(5-chloro-2-methoxyphenyl)-1-[(2-chloro-5-thiazolyl)methyl]-2-hydroxy-4-oxo-4H-pyrido[1,2-a]pyrimidinium inner salt;
1-[(6-fluoro-3-pyridinyl)methyl]-2-hydroxy-3-[2-methoxy-5-(trifluoromethyl)phenyl]-4-oxo-4H-pyrido[1,2-a]pyrimidinium inner salt;
1-[(2-chloro-5-thiazolyl)methyl]-2-hydroxy-3-[2-methoxy-5-(trifluoromethyl)phenyl]-4-oxo-4H-pyrido[1,2-a]pyrimidinium inner salt;
3-(2,4-difluorophenyl)-2-hydroxy-4-oxo-1-(5-thiazolylmethyl)-4H-pyrido[1,2-c]pyrimidinium inner salt;
3-(2-fluorophenyl)-2-hydroxy-4-oxo-1-[(2-methyl-5-thiazolyl)methyl]-4H-pyrido[1,2-a]pyrimidinium inner salt;
3-(2-chloro-6-fluorophenyl)-1-[(6-chloro-3-pyridinyl)methyl]-2-hydroxy-4-oxo-4H-pyrido[1,2-a]pyrimidinium inner salt;
1-[(2-chloro-5-thiazolyl)methyl]-3-(2-ethoxyphenyl)-2-hydroxy-4-oxo-4H-pyrido[1,2-a]pyrimidinium inner salt;
1-[(6-fluoro-3-pyridinyl)methyl]-3-[2-fluoro-5-(trifluoromethoxy)phenyl]-2-hydroxy-4-oxo-4H-pyrido[1,2-a]pyrimidinium inner salt;
1-[(2-chloro-5-thiazolyl)methyl]-2-hydroxy-3-(3-methylphenyl)-4-oxo-4H-pyrido[1,2-a]pyrimidinium inner salt;
1-[(6-chloro-3-pyridinyl)methyl]-2-hydroxy-3-(3-methoxyphenyl)-4-oxo-4H-pyrido[1,2-a]pyrimidinium inner salt;
1-[(6-chloro-3-pyridinyl)methyl]-3-(2-fluorophenyl)-2-hydroxy-4-oxo-4H-pyrido[1,2-a]pyrimidinium inner salt;

1-[(6-chloro-3-pyridinyl)methyl]-3-(2,5-difluorophenyl)-2-hydroxy-4-oxo-4H-pyrido[1,2-a]pyrimidinium inner salt;

3-(5-chloro-2-fluorophenyl)-1-[(6-chloro-3-pyridinyl)methyl]-2-hydroxy-4-oxo-4H-pyrido[1,2-a]pyrimidinium inner salt;

1-[(6-chloro-3-pyridinyl)methyl]-hydroxy-4-oxo-3-(2,4,6-trifluorophenyl)-4H-pyrido[1,2-a]pyrimidinium inner salt;

1-[(6-chloro-3-pyridinyl)methyl]-3-(2,3-difluorophenyl)-2-hydroxy-4-oxo-4H-pyrido[1,2-a]pyrimidinium inner salt;

3-(5-bromo-2-fluorophenyl)-1-[(6-chloro-3-pyridinyl)methyl]-2-hydroxy-4-oxo-4H-pyrido[1,2-a]pyrimidinium inner salt;

1-[(6-chloro-3-pyridinyl)methyl]-3-(2,6-difluorophenyl)-2-hydroxy-4-oxo-4H-pyrido[1,2-a]pyrimidinium inner salt;

1-[(2-chloro-5-thiazolyl)methyl]-3-[3-(trifluoromethoxy)phenyl]-2-hydroxy-4-oxo-4H-pyrido[1,2-a]pyrimidinium inner salt;

1-[(6-bromo-3-pyridinyl)methyl]-3-(2,4-difluorophenyl)-2-hydroxy-4-oxo-4H-pyrido[1,2-a]pyrimidinium inner salt;

1-[(2-chloro-5-thiazolyl)methyl]-2-hydroxy-3-(3-methoxyphenyl)-4-oxo-4H-pyrido[1,2-a]pyrimidinium inner salt;

3-[3-bromo-5-(trifluoromethoxy)phenyl]-1-[(2-chloro-5-thiazolyl)methyl]-2-hydroxy-4-oxo-4H-pyrido[1,2-a]pyrimidinium inner salt;

3-[3-bromo-5-(trifluoromethyl)phenyl]-1-[(2-chloro-5-thiazolyl)methyl]-2-hydroxy-4-oxo-4H-pyrido[1,2-a]pyrimidinium inner salt;

3-(3-chloro-2-fluorophenyl)-1-[(6-chloro-3-pyridinyl)methyl]-2-hydroxy-4-oxo-4H-pyrido[1,2-a]pyrimidinium inner salt;

2-hydroxy-4-oxo-1-(5-pyrimidinylmethyl)-3-[3-(trifluoromethyl)phenyl]-4H-pyrido[1,2-a]pyrimidinium inner salt;

1-[(2-chloro-5-thiazolyl)methyl]-2-hydroxy-4-oxo-3-(4'-(trifluoromethyl)[1,1'-biphenyl]-3-yl)-4H-pyrido[1,2-a]pyrimidinium inner salt;

1-[(2-chloro-5-thiazolyl)methyl]-3-(4'-fluoro[1,1'-biphenyl]-3-yl)-2-hydroxy-4-oxo-4H-pyrido[1,2-a]pyrimidinium inner salt;

3-(5-chloro-2-fluorophenyl)-1-[(6-fluoro-3-pyridinyl)methyl]-2-hydroxy-4-oxo-4H-pyrido[1,2-a]pyrimidinium inner salt;

8-[(6-chloro-3-pyridinyl)methyl]-6-(2,3-difluorophenyl)-7-hydroxy-5-oxo-5H-thiazolo[3,2-a]pyrimidinium inner salt;

3-(2,4-difluorophenyl)-1-[(6-fluoro-3-pyridinyl)methyl]-2-hydroxy-4-oxo-4H-pyrido[1,2-a]pyrimidinium inner salt;

1-[(2-chloro-5-thiazolyl)methyl]-2-hydroxy-4-oxo-3-[4-(trifluoromethyl)-2-pyridinyl]-4H-pyrido[1,2-a]pyrimidinium inner salt; and 3-(4-cyano-2-fluorophenyl)-1-[(6-chloro-3-pyridinyl)methyl]-2-hydroxy-4-oxo-4H-pyrido[1,2-a]pyrimidinium inner salt.

Further specific embodiments include the compositions described in the Summary of the Invention wherein component (a) is a compound of Formula 1 selected from the group consisting of:

3-(2-chloro-6-fluorophenyl)-1-[(6-chloro-3-pyridinyl)methyl]-2-hydroxy-4-oxo-4H-pyrido[1,2-a]pyrimidinium inner salt;

1-[(2-chloro-5-thiazolyl)methyl]-3-(2-ethoxyphenyl)-2-hydroxy-4-oxo-4H-pyrido[1,2-a]pyrimidinium inner salt;

1-[(2-chloro-5-thiazolyl)methyl]-2-hydroxy-3-(3-methylphenyl)-4-oxo-4H-pyrido[1,2-a]pyrimidinium inner salt;

3-(3-chloro-2-fluorophenyl)-1-[(6-chloro-3-pyridinyl)methyl]-2-hydroxy-4-oxo-4H-pyrido[1,2-a]pyrimidinium inner salt;

2-hydroxy-4-oxo-1-(5-pyrimidinylmethyl)-3-[3-(trifluoromethyl)phenyl]-4H-pyrido[1,2-a]pyrimidinium inner salt;

1-[(2-chloro-5-thiazolyl)methyl]-2-hydroxy-4-oxo-3-(4'-(trifluoromethyl)[1,1'-biphenyl]-3-yl)-4H-pyrido[1,2-a]pyrimidinium inner salt;

1-[(2-chloro-5-thiazolyl)methyl]-3-(4'-fluoro[1,1'-biphenyl]-3-yl)-2-hydroxy-4-oxo-4H-pyrido[1,2-a]pyrimidinium inner salt; and 3-(5-chloro-2-fluorophenyl)-1-[(6-fluoro-3-pyridinyl)methyl]-2-hydroxy-4-oxo-4H-pyrido[1,2-a]pyrimidinium inner salt.

Further specific embodiments include the compositions described in the Summary of the Invention wherein component (a) is a compound of Formula 1 selected from the group consisting of compound numbers 6, 7, 9, 10, 19, 26, 29, 34, 38, 39, 43, 48, 58, 74, 78, 85, 87, 88, 90, 94, 111, 117, 122, 209, 220, 268, 410, 510, 537, 547 and 548, wherein the compound number refers to compounds in Index Tables A-C.

Further specific embodiments include the compositions described in the Summary of the Invention wherein component (a) is a compound of Formula 1 selected from the group consisting of compound numbers 541, 542, 576, 583, 594, 654, 657, 669, 670, 682, 683, 687, 718, 725, 726, 727, 734, 735, 737, 744, 745, 746, 748, 749, 750, 926 and 930, wherein the compound number refers to compounds in Index Tables A-C.

Of note is that compositions of this invention are characterized by favorable metabolic and/or soil residual patterns and exhibit activity controlling a spectrum of agronomic and nonagronomic invertebrate pests.

Of particular note, for reasons of invertebrate pest control spectrum and economic importance, protection of agronomic crops from damage or injury caused by invertebrate pests by controlling invertebrate pests are embodiments of the invention. Compositions of this invention because of their favorable translocation properties or systemicity in plants also protect foliar or other plant parts which are not directly contacted with the compositions.

Also noteworthy as embodiments of the present invention are compositions comprising components (a) and (b) (i.e. in biologically effective amounts) as described in any of the preceding Embodiments, as well as any other embodiments described herein, and any combinations thereof, further comprising at least one additional component selected from the group consisting of a surfactant, a solid diluent and a liquid diluent, said compositions optionally further comprising at least one additional biologically active compound or agent (i.e. in a biologically effective amount).

Embodiments of the invention also include a composition for protecting an animal comprising components (a) and (b) (i.e. in parasiticidally effective amounts) of any of the preceding Embodiments and a carrier.

Embodiments of the invention further include methods for controlling an invertebrate pest comprising contacting the invertebrate pest or its environment with a biologically effective amount of a composition of any of the preceding Embodiments. Of particular note is a method for protecting an animal comprising administering to the animal a parasiticidally effective amount of a composition of any of the preceding Embodiments.

Embodiments of the invention also include a composition comprising of any of the preceding Embodiments, in the form of a soil drench liquid formulation. Embodiments of the invention further include methods for controlling an invertebrate pest comprising contacting the soil with a liquid composition as a soil drench comprising a biologically effective amount of a composition of any of the preceding Embodiments.

Embodiments of the invention also include a spray composition for controlling an invertebrate pest comprising a biologically effective amount of a composition of any of the preceding Embodiments and a propellant. Embodiments of the invention further include a bait composition for controlling an invertebrate pest comprising a biologically effective amount of a composition of any of the preceding Embodiments, one or more food materials, optionally an attractant, and optionally a humectant. Embodiments of the invention also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

Embodiments of the invention also include a method for protecting a seed from an invertebrate pest comprising contacting the seed with a biologically effective amount of a composition of any of the preceding Embodiments.

Embodiments of the invention also include methods for protecting an animal from an invertebrate parasitic pest comprising administering to the animal a parasiticidally effective amount of a composition of any of the preceding Embodiments.

Embodiments of the invention also include methods wherein the invertebrate pest or its environment is contacted with a biologically effective amount of a composition of any of the preceding Embodiments, and at least one additional component selected from the group consisting of surfactants, solid diluents and liquid diluents, said composition optionally further comprising a biologically effective amount of at least one additional biologically active compound or agent, provided that the methods are not methods of medical treatment of a human or animal body by therapy.

One or more of the following methods and variations as described in Schemes 1-10 can be used to prepare the compounds of Formula 1. The definitions of $R^1$, $R^2$ and Z in the compounds of Formulae 1-8 below are as defined above in the Summary of the Invention unless otherwise noted. Formulae 1a and 1b are various subsets or analogs of Formula 1, and all substituents for Formulae 1a and 1b are as defined above for Formula 1 unless otherwise indicated. Ambient or room temperature is defined as about 20-25° C.

Compounds of Formula 1 can be prepared by condensation of appropriately substituted compounds of Formula 2 with optionally substituted malonic acids (3a) in the presence of condensing agents as shown in Scheme 1. Condensing agents can be carbodiimides such as dicyclohexyl carbodiimide (see, for example, Koch, A. et al. *Tetrahedron* 2004, 60, 10011-10018) or other agents well known in the art to form amide bonds with or without activating agents such as N-hydroxybenzotriazole as described in *Science of Synthesis* 2005, 21, 17-25 and *Tetrahedron* 2005, 61, 10827-10852. This reaction is typically carried out in an inert organic solvent, such as dichloromethane or 1,2-dichloroethane, at temperatures from about 0 to about 80° C. for a period of 10 min to several days.

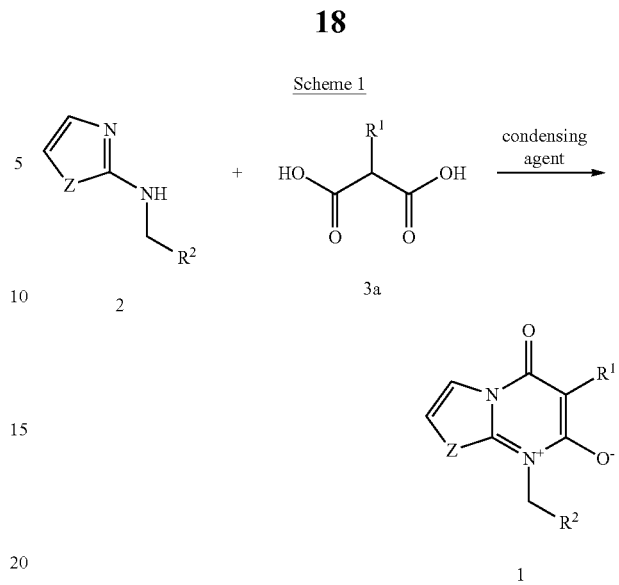

Scheme 1

Compounds of Formula 1 can also be prepared by the condensation of compounds of Formula 2 with malonic acid esters (3b) wherein R is a $C_1$-$C_5$ alkyl group, preferably a $C_1$-$C_4$ alkyl group, as shown in Scheme 2. These reactions can be performed neat or in the presence of inert solvents as described in *Bulletin of the Chemical Society of Japan* 1999, 72(3), 503-509. Inert solvents include, but are not limited to, high boiling hydrocarbons such as mesitylene, tetralin or cymene, or high boiling ethers such as diphenyl ether. Typical temperatures range from 50 to 250° C. Of note are temperatures from 150 to 200° C., which typically provide rapid reaction times and high yields. These reactions can also be performed in microwave reactors within the same temperature ranges. Typical reaction times range from 5 min to several hours.

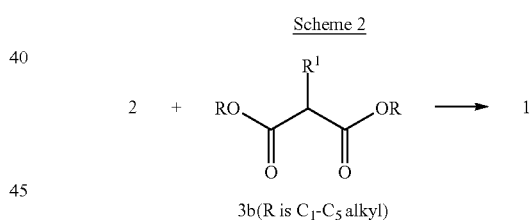

Scheme 2

Compounds of Formula 3a can be prepared by a variety of methods known in the art, for example by base hydrolysis of compounds of Formula 3b. Compounds of Formula 3b can be prepared by arylation of malonate esters catalyzed by palladium (*J. Org. Chem.* 2002, 67, 541-555) or copper (*Org. Lett.* 2002, 4, 269-272 and *Org. Lett.* 2005, 7, 4693-4695).

Alternatively, compounds of Formula 3b can be prepared by the method shown in Scheme 2a (see, for example, *J. Med. Chem.* 1982, 25(6), 745-747).

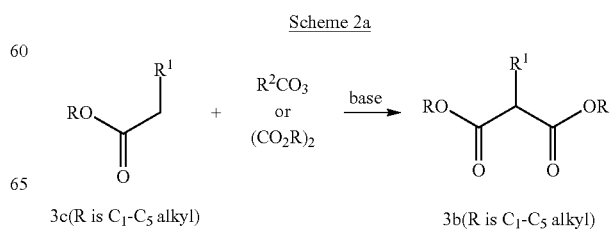

Scheme 2a

Compounds of Formula 3b can also be prepared by the method shown in Scheme 2b. Reaction of nitriles of Formula 3g with dialkyl carbonates yields nitrile esters of Formula 3h, and subsequent acidic hydrolysis in the presence of an alcohol provides the compounds of Formula 3b (see, for example, *Helvetica Chimica Acta* 1991, 74(2), 309-314).

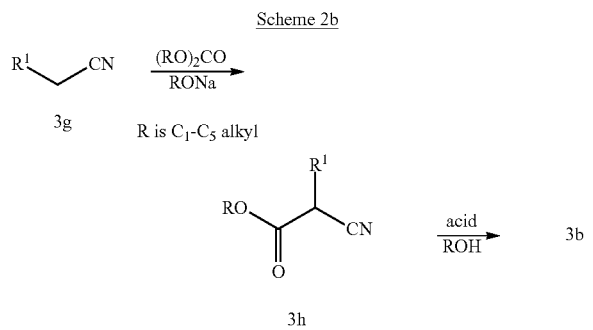

Compounds of Formula 1 can also be prepared by treatment of compounds of Formula 2 with activated esters of Formula 3c wherein LvO is an activated leaving group as shown in Scheme 3. Examples of Lv preferred for ease of synthesis or reactivity are phenyl, 4-nitrophenyl or halogen-substituted phenyl (e.g., 2,4,6-trichlorophenyl, pentachlorophenyl or pentafluorophenyl) as described in *Archiv der Pharmazie* (Weinheim, Germany) 1991, 324, 863-866. Other activated esters are well known in the art and include, but are not limited to, N-hydroxysuccinimide esters (see, for example, *J. Am. Chem. Soc.* 2002, 124, 6872-6878). Typical temperatures range from 50 to 200° C. Of note are temperatures from 50 to 150° C., which typically provide rapid reaction times and high yields. These reactions can be performed with or without solvent, such as toluene, and in microwave reactors within the same temperature ranges. Typical reaction times range from 5 min to 2 h.

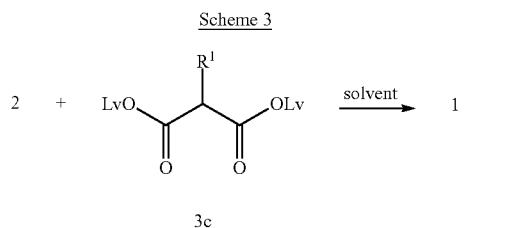

Compounds of the Formula 3c can be prepared, for example, from compounds of Formula 3a (see, for example, *J. Het. Chem.* 1980, 17, 337).

Compounds of Formula 1 can also be prepared by condensation of compounds of Formula 2 with compounds of Formula 3d or 3e, or by condensation of compounds of Formula 2 with mixtures of compounds of Formulae 3d and 3e as shown in Scheme 4. These reactions are typically performed in an inert solvent, such as dichloromethane, and optionally in the presence of two or more equivalents of an acid acceptor (see, for example, *Zeitschrift für Naturforschung, Teil B: Anorganische Chemie, Organische Chemie* 1982, 37B(2), 222-233). Typical acid acceptors include, but are not limited to, triethylamine, N,N-diisopropylethylamine, pyridine and substituted pyridines.

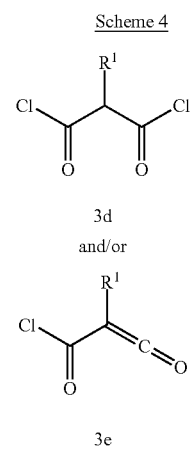

Compounds of Formula 1a (i.e. analogous to Formula 1 wherein $R^1$ is H), which are useful as starting compounds for the methods of Schemes 7 and 8, can be prepared by condensation of compounds of Formula 2 with carbon suboxide (3f) (see, for example, *J. Org. Chem.* 1972, 37(9), 1422-1425) as shown in Scheme 5. The reactions are typically performed in an inert solvent such as ether and can include the use of a catalyst such as $AlCl_3$.

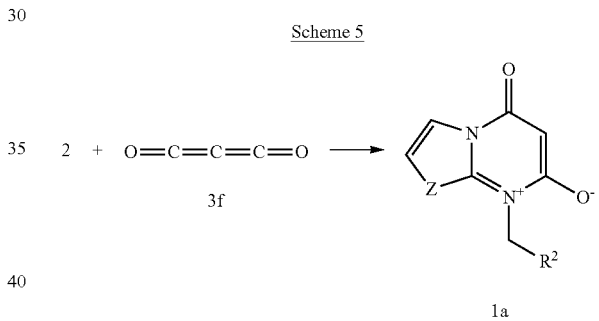

Compounds of Formula 1 can also be prepared from compounds of Formula 1b (i.e. Formula 1 wherein $R^1$ is Cl, Br or I, preferably Br or I) and compounds of Formula 4 wherein M with $R^1$ forms a boronic acid, boronic acid ester or trifluoroborate salt, or M is trialkylstannyl or zinc as shown in Scheme 6.

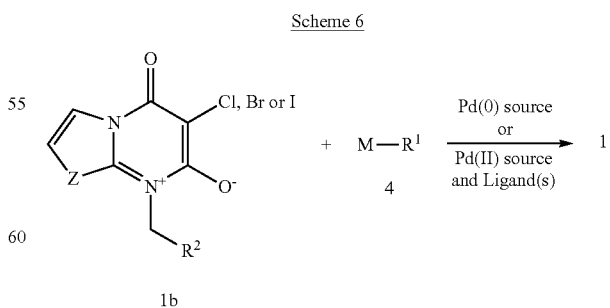

In a similar manner, compounds of Formula 1 wherein a substituent (e.g., $R^1$) consists of two directly bonded aromatic rings (e.g., a phenyl or pyridinyl ring bonded to a phenyl ring)

can be prepared by palladium-catalyzed coupling of the two appropriately substituted aromatic rings. These palladium-catalyzed couplings between an aromatic chloride, bromide or iodide and an aromatic boronic acid or ester, or an aromatic tin or zinc reagent are well known and have been extensively described in the art.

These coupling reactions are typically carried out in the presence of a palladium catalyst and a base optionally under an inert atmosphere. The palladium catalysts used for these coupling reactions typically comprises palladium in a formal oxidation state of either 0 (i.e. Pd(0)) or 2 (i.e. Pd(II)). A wide variety of such palladium-containing compounds and complexes are useful as catalysts for these reactions. Examples of palladium-containing compounds and complexes useful as catalysts in the methods include palladium on carbon, $PdCl_2(PPh_3)_2$ (dichlorobis(triphenylphosphine)palladium(II)), $Pd(PPh_3)_4$ (tetrakis-(triphenylphosphine)palladium(0)), $Pd(C_5H_7O_2)_2$ (palladium(II) acetylacetonate), $Pd_2(dba)_3$ (tris(dibenzylideneacetone)dipalladium(0)), and [1,1'-bis(diphenylphosphino)-ferrocene]dichloropalladium(II). These coupling methods are generally conducted in a liquid phase, and therefore the palladium catalyst preferably has good solubility in the liquid phase. Useful solvents include, for example, water, ethers such as 1,2-dimethoxyethane, amides such as N,N-dimethylacetamide, and non-halogenated aromatic hydrocarbons such as toluene.

The coupling methods can be conducted over a wide range of temperatures, ranging from about 25 to about 200° C. Of note are temperatures from about 60 to about 150° C., which typically provide fast reaction times and high product yields. The general methods and procedures for Stille, Negishi and Suzuki couplings with aryl iodides, bromides or chlorides and an aryl tin, aryl zinc or aryl boronic acid respectively are well known in the literature; see, for example, E. Negishi, *Handbook of Organopalladium Chemistry for Organic Synthesis*, Wiley-Interscience, 2002, New York, N.Y.

Compounds of Formula 1 can also be prepared from compounds of Formula 1a and compounds of Formula 5 wherein $X^1$ is Cl, Br or I (preferably Br or I) as shown in Scheme 7.

Scheme 7

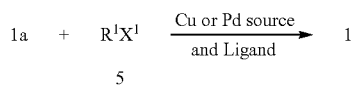

These reactions are typically carried out in the presence of a copper or palladium catalyst optionally under an inert atmosphere. The copper catalysts used for the present method typically comprise copper in metallic form (e.g., as a powder) or copper in a formal oxidation state of 1 (i.e. Cu(I)). Examples of copper-containing compounds useful as catalysts in the method of Scheme 7 include Cu, CuI, CuBr, CuCl. Examples of palladium-containing compounds useful as catalysts in the method of Scheme 7 include, but are not limited to, $Pd(OAc)_2$. Useful solvents for the method of Scheme 7 include, for example, ethers such as 1,4-dioxane, amides such as N,N-dimethylacetamide and dimethyl sulfoxide.

The method of Scheme 7 can be conducted over a wide range of temperatures from 25 to 200° C. Of note are temperatures from 40 to 150° C. The method of Scheme 7 can be conducted in the presence of a ligand. A wide variety of such copper-binding compounds are useful as ligands for the present method. Examples of useful ligands include 1,10-phenanthroline, N,N-dimethylethylenediamine, L-proline and 2-picolinic acid. The general methods and procedures for copper-catalyzed Ullmann-type coupling reactions are well known in the literature; see, for example, Xie, Ma, et al. *Org. Lett.* 2005, 7, 4693-4695.

Compounds of Formula 1b can be prepared from compounds of Formula 1a by halogenation using, for example, liquid bromine or N-halosuccinimides (6) as shown in Scheme 8. Typically the reaction is performed in an inert solvent, more typically a halogenated solvent such as methylene chloride or 1,2-dichloroethane. The reaction is typically performed at temperatures from 0 to 80° C., more typically at ambient temperature.

Scheme 8

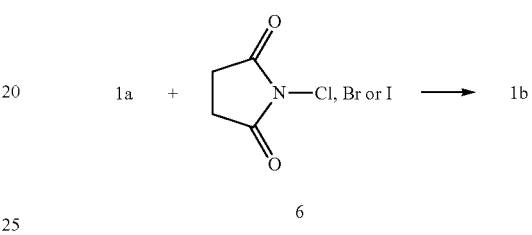

Compounds of Formula 1 can also be prepared by alkylation of compounds of Formula 7 using appropriately substituted alkylating agents and bases such as potassium carbonate as shown in Scheme 9 (see, for example, Kappe, T. et al. *Monatschefte fur Chemie* 1971, 102, 412-424 and Urban, M. G.; Arnold, W. *Helvetica Chimica Acta* 1970, 53, 905-922). Alkylating agents include, but are not limited to, alkyl chlorides, bromides, iodides and sulfonate esters. A wide variety of bases and solvents can be employed in the method of Scheme 9, and these bases and solvents are well known in the art.

Scheme 9

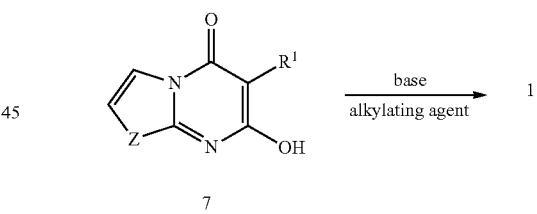

Compounds of Formula 7 can be prepared from compounds of Formula 2a by methods analogous to those shown in Schemes 1 through 5. Compounds of Formula 2a are commercially available or can be prepared by general methods well known in the art.

A particularly useful method for the preparation of compounds of Formula 2 is shown in Scheme 10. In the method of Scheme 10, compounds of Formula 2a are protected with suitable protecting groups such as, but not limited to, tert-butoxycarbonyl, acetyl or formyl to form the intermediate of Formula 2b wherein PG is a protecting group. The compound of Formula 2b is then alkylated with an appropriate reagent of Formula 8 (wherein X is a leaving group such as a halogen) to give an intermediate of Formula 2c. The protecting group is removed to provide a compound of Formula 2. Conditions for the formation and removal of protecting groups on an amine function are known in the literature (see, for example, Greene, T. W.; Wuts, P. G. M. *Protective Groups in Organic Synthesis*, 2nd ed.; Wiley: New York, 1991).

Compounds of Formula 2 can be prepared in a variety of ways known in the art; see, for example, Patai, S. *The Chemistry of Functional Groups: The Chemistry of Amidines and Imidates*; Wiley: Chichester, UK, 1975; *The Chemistry of Amidines and Imidates*; Patai, S.; Rappoport, Z., Eds.; Wiley: Chichester, UK, 1991; Vol. 2; Mega, T. et al. *Bulletin of the Chemical Society of Japan* 1988, 61(12), 4315-4321; Ife, R. et al. *European Journal of Medicinal Chemistry* 1989, 24(3), 249-257; Wagaw, S.; Buchwald, S. *Journal of Organic Chemistry* 1996, 61(21), 7240-7241; Shen, Q. et al. *Angewandte Chemie, International Edition* 2005, 44(9), 1371-1375; and Okano, K. et al. *Organic Letters* 2003, 5(26), 4987-4990.

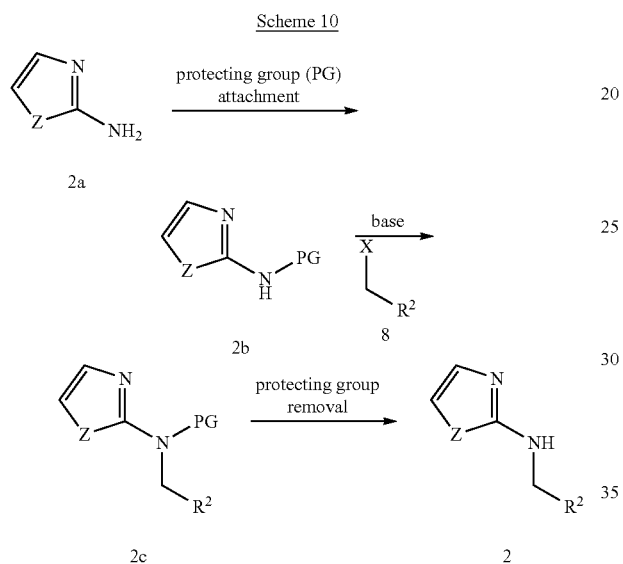

Schemes 1 through 10 illustrate methods to prepare compounds of Formula 1 having a variety of substituents noted for $R^1$, $R^2$ and Z. Compounds of Formula 1 having $R^1$, $R^2$ and Z substituents other than those particularly noted for Schemes 1 through 10 can be prepared by general methods known in the art of synthetic organic chemistry, including methods analogous to those described for Schemes 1 to 10.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. Ambient or room temperature is defined as about 20-25° C. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "dd" means doublet of doublets, "ddd" means doublet of doublet of doublets, "t" means triplet, "m" means multiplet, and "br s" means broad singlet. For mass spectral data, the numerical value reported is the molecular weight of the parent molecular ion (M) formed by addition of H$^+$ (molecular weight of 1) to the molecule to give a M+1 peak observed by mass spectrometry using atmospheric pressure chemical ionization (AP$^+$).

Synthesis Example 1

Preparation of 2-hydroxy-4-oxo-3-phenyl-1-(2,2,2-trifluoroethyl)-4H-pyrido[1,2-c]-pyrimidinium inner salt A mixture of diethyl phenylmalonate (0.62 g, 2.7 mmol) and N-(2,2,2-trifluoroethyl)-2-pyridinamine (0.87 g, 2.7 mmol, prepared by the method of Bissell, E. R.; Swanslger, R. W. *J. Chem. Eng. Data.* 1981, 26, 234-235) was heated to 180° C. for 2 h. After cooling, the reaction mixture was purified by chromatography on silica gel by elution with ethyl acetate to provide the title compound as a yellow solid (45 mg).

$^1$H NMR (CDCl$_3$) δ 9.61 (dd, 1H), 8.17 (ddd, 1H), 7.74 (d, 2H), 7.55 (d, 1H), 7.45 (t, 1H), 7.39 (m, 2H), 7.21-7.25 (m, 1H), 5.10 (br s, 2H).

Synthesis Example 2

Preparation of 1-[(6-chloro-3-pyridinyl)methyl]-3-[2-fluoro-5-(trifluoromethoxy)phenyl]-2-hydroxy-4-oxo-4H-pyrido[1,2-a]pyrimidinium inner salt Step A: Preparation of 6-chloro-N-2-pyridinyl-3-pyridinemethanamine A mixture of 2-fluoropyridine (1.4 g, 15 mmol) and 6-chloro-3-pyridinemethanamine (2.55 g, 18 mmol) in N-methylpyrrolidinone (5 mL) was heated at 230° C. in a microwave reactor for 30 min. This reaction was repeated four times using the same amounts of starting materials for each repetition. All five of the reaction mixtures were then poured into saturated aqueous sodium bicarbonate solution and extracted into ethyl acetate. The organic layer was washed with saturated aqueous sodium bicarbonate solution, dried over Na$_2$SO$_4$, and concentrated under reduced pressure. The crude product was then purified by chromatography on silica gel using 10% ethyl acetate in hexanes as the eluent to provide the title compound as an oil (5.1 g).

$^1$H NMR (CDCl$_3$) δ 8.38 (s, 1H), 8.1 (m, 1H), 7.67 (d, 1H), 7.42 (dd, 1H), 7.28 (d, 1H), 6.63 (m, 1H), 6.38 (d, 1H), 4.88 (s, 1H), 4.56 (d, 2H).

Step B: Preparation of 1-[(6-chloro-3-pyridinyl)methyl]-2-hydroxy-4-oxo-4H-pyrido[1,2-a]pyrimidinium inner salt A solution of dicyclohexylcarbodiimide (4.12 g, 20 mmol in 10 mL of dichloromethane) was added to a solution of 6-chloro-N-2-pyridinyl-3-pyridinemethanamine (i.e. the product of Step A) (2.19 g, 10 mmol) and malonic acid (1.04 g, 10 mmol) in dichloromethane (10 mL) in a round bottom flask. The reaction mixture was stirred at room temperature for 16-24 h. The reaction mixture was then filtered, and the filtration cake was washed with diethyl ether. The filtrate was concentrated under reduced pressure, and the resulting residue was washed with methanol to provide the title compound as a pale yellow solid (2.54 g).

$^1$H NMR (acetone-d$_6$) δ 9.32 (d, 1H), 8.52 (s, 1H), 8.29 (dd, 1H), 7.79 (m, 2H), 7.52 (t, 1H), 7.42 (d, 1H), 5.63 (s, 2H), 5.03 (s, 1H).

Step C: Preparation of 1-[(6-chloro-3-pyridinyl)methyl]-2-hydroxy-3-iodo-4-oxo-4H-pyrido[1,2-a]pyrimidinium inner salt N-iodosuccinimide (1.12 g, 5 mmol) was added to a solution of 1-[(6-chloro-3-pyridinyl)methyl]-2-hydroxy-4-oxo-4H-pyrido[1,2-a]pyrimidinium inner salt (i.e. the product of Step B) (1.4 g, 5 mmol) in N,N-dimethylformamide (10 mL) and stirred for 5 min. Water was added, and the mixture was extracted with dichloromethane. The combined organic phases were washed repeatedly with water, dried over Na$_2$SO$_4$, and concentrated under reduced pressure. The resulting crude product (1.8 g) was used in the next step without further purification.

$^1$H NMR (CDCl$_3$) δ 9.49 (d, 1H), 8.45 (d, 1H), 8.12 (dd, 1H), 7.40 (m, 2H), 7.32 (d, 1H), 5.50 (s, 2H).

Step D: Preparation of 1-[(6-chloro-3-pyridinyl)methyl]-3-[2-fluoro-5-(trifluoromethoxy)phenyl]-2-hydroxy-4-oxo-4H-pyrido[1,2-a]pyrimidinium inner salt 1-[(6-Chloro-3-pyridinyl)methyl]-2-hydroxy-3-iodo-4-oxo-4H-pyrido[1,2-a]pyrimidinium inner salt (i.e. the product of Step C) (206 mg, 0.5 mmol), 2-fluoro-5-(trifluoromethoxy)benzeneboronic acid (224 mg, 1 mmol) and dichlorobis(triphenyl-phosphine)palladium(II) (35 mg, 0.005 mmol) were dissolved in dioxane (2 mL). Aqueous sodium carbonate solution (2 N, 1 mL) was added, and the reaction mixture was heated in a microwave reactor for 10 min at 160° C. The cooled reaction mixture was poured directly onto a silica gel column and eluted successively with hexanes, 30% ethyl acetate in hexanes, 50% ethyl acetate in hexanes, and finally ethyl acetate to yield the title compound as a solid (20 mg).

$^1$H NMR (CDCl$_3$) δ 9.53 (d, 1H), 8.49 (s, 1H), 8.11 (dd, 1H), 7.69 (d, 1H), 7.50 (d, 1H), 7.41 (m, 2H), 7.34 (d, 1H), 7.16 (d, 2H), 7.58 (br s, 2H).

Synthesis Example 3

Preparation of 2-hydroxy-4-oxo-3-phenyl-1-(2,2,2-trifluoroethyl)-4H-pyrido[1,2-c]-pyrimidinium inner salt Step A: Preparation of N-(2,2,2-trifluoroethyl)-2-pyridinamine A mixture of 2-fluoropyridine (2.00 g, 20.6 mmol) and 2,2,2-trifluoroethylamine hydrogen chloride (5.00 g, 36.9 mmol) was heated to 220° C. for 30 min in a microwave reactor. The same reaction was repeated 5 times. The reaction mixtures from all 6 reactions were cooled, combined and diluted with ethyl acetate (150 mL). The organic mixture was neutralized by washing with saturated aqueous sodium bicarbonate, water (30 mL) and brine (30 mL). The organic phase was dried over Na$_2$SO$_4$ and concentrated, and the resulting residue was purified by chromatography on silica gel using 80% ethyl acetate/hexane as eluant to give the title compound as a white solid (17.0 g).

$^1$H NMR (CDCl$_3$) δ 8.15 (d, 1H), 7.45 (dd, 1H), 6.69 (dd, 1H), 6.49 (d, 1H), 4.58 (br s, 1H), 4.11 (q, 2H).

Step B: Preparation of 1,3-bis(2,4,6-trichlorophenyl) 2-phenylpropanedioate

To a slurry of phenylmalonic acid (5.00 g, 27.8 mmol) in dichloromethane (7 mL) at room temperature was added a drop of N,N-dimethylformamide, followed by the dropwise addition of oxalyl chloride (9.09 g, 71.6 mmol) at such a rate to keep gas evolution under control. The reaction mixture was stirred for an additional hour at room temperature, during which time the reaction mixture clarified. 2,4,6-Trichlorophenol (15 g, 76 mmol) was added, and the reaction mixture was stirred at room temperature for 18 h. The reaction mixture was concentrated under vacuum, and methanol (100 mL) was added to the residue, which resulted in precipitation of a large amount of solid. The solid was collected by filtration, rinsed with methanol (80 mL) and air dried to give the title product as a white solid (13 g).

$^1$H NMR (CDCl$_3$) δ 7.64-7.62 (m, 2H), 7.46-7.43 (m, 3H), 7.36 (s, 4H), 5.32 (s, 1H).

Step C: Preparation of 2-hydroxy-4-oxo-3-phenyl-1-(2,2,2-trifluoroethyl)-4H-pyrido[1,2-c]-pyrimidinium inner salt A solution of N-(2,2,2-trifluoroethyl)-2-pyridinamine (i.e. the product of Step A) (2.00 g, 11.4 mmol) and 1,3-bis(2,4,6-trichlorophenyl) 2-phenylpropanedioate (i.e. the product of Step B) (6.40 g, 11.9 mmol) in toluene (40 mL) was refluxed for 1 h. The reaction mixture was cooled in an ice-water bath with stirring for 2 h. The solid that precipitated was collected by filtration, rinsed with diethyl ether and air dried to give the title compound as a yellow solid (3.44 g).

$^1$H NMR (CD$_3$S(O)CD$_3$) δ 9.37 (d, 1H), 8.42 (m, 1H), 8.11 (d, 1H), 7.66 (d, 2H), 7.61 (m, 1H), 7.32 (t, 2H), 7.18 (t, 1H), 5.35 (q, 2H).

Synthesis Example 4

Preparation of 8-[(6-chloro-3-pyridinyl)methyl]-7-hydroxy-5-oxo-6-[3-(trifluoromethoxy)phenyl]-5H-thiazolo[3,2-a]pyrimidinium inner salt Step A: Preparation of N-[(6-chloro-3-pyridinyl)methylene]-2-thiazolamine 2-Aminothiazole (0.75 g, 7.5 mmol) was added to 2-chloropyridine-6-carboxaldehyde (1.0 g, 7.1 mmol) in dichloromethane (25 mL) at room temperature. The suspension was stirred an additional 10 min and then concentrated to dryness under vacuum. The resulting residue was heated to 90° C. on a rotary evaporator with a non-returning bump trap to facilitate water removal. After 30 min the resultant yellow solid was checked by NMR to verify reaction completion (by disappearance of the characteristic aldehyde peak at 10.10 ppm (s, 1H)). The title compound was obtained as a yellow solid (1.55 g) and used in the next step without further purification.

$^1$H NMR (CDCl$_3$) δ 9.10 (s, 1H), 8.84 (d, 1H), 8.35-8.32 (dd, 1H), 7.72-7.70 (d, 1H), 7.48-7.46 (d, 1H), 7.32-7.31 (d, 1H).

Step B: Preparation of 6-chloro-N-2-thiazolyl-3-pyridinemethanamine

N-[(6-chloro-3-pyridinyl)methylene]-2-thiazolamine (i.e. the product of Step A) (0.55 g, 2.46 mmol) was added portionwise to a stirred excess of sodium borohydride (0.45 g, 11.8 mmol) in methanol (30 mL). Additional portions of sodium borohydride (2×1 equivalent) were added during the addition of the imine to maintain an exothermic reaction. After addition was complete, the reaction mixture was allowed to stir for 5 min at ambient temperature. The excess reducing agent was quenched by adding glacial acetic acid until gas evolution ceased. The clear reaction mixture was concentrated, and the resulting residue was partitioned between saturated aqueous sodium carbonate and ethyl acetate. The aqueous phase was extracted with ethyl acetate (3×30 mL), and the combined organic phases were washed with brine, dried (MgSO$_4$) and concentrated to give the title compound as a tan powder (0.55 g).

$^1$H NMR (CDCl$_3$) δ 8.39 (d, 1H), 7.71-7.68 (dd, 1H), 7.30-7.28 (d, 1H), 6.98 (d, 1H), 6.48 (d, 1H), 4.48 (s, 2H).

Step C: Preparation of 2[3-(trifluoromethoxy)phenyl]propanedioic acid

Diethyl 3-trifluoromethoxyphenylmalonate (3.00 g, 9.38 mmol) was stirred in an aqueous sodium hydroxide solution (15 g, 20% by weight) at 65° C. for 10 min. The reaction mixture was then cooled in an ice bath, and ice (7 g) was added to the reaction mixture, followed by 6 N hydrochloric acid to adjust the pH to about 2. The aqueous mixture was saturated with sodium chloride and extracted with ethyl acetate three times. The combined organic phases were dried (MgSO$_4$) and concentrated to give a solid, which was triturated with a mixture of 33% diethyl ether/hexane to give the title compound as a white solid (2.24 g).

$^1$H NMR (CD$_3$C(O)CD$_3$) δ 11.51 (br s, 2H), 7.54-7.51 (m, 3H), 7.35-7.30 (m, 1H), 4.91 (s, 1H).

Step D: Preparation of 8-[(6-chloro-3-pyridinyl)methyl]-7-hydroxy-5-oxo-6-[3-(trifluoromethoxy)phenyl]-5H-thiazolo[3,2-a]pyrimidinium inner salt Oxalyl chloride (1.0 mL, 11 mmol) was added dropwise at ambient temperature to a slurry of 2-[3-(trifluoromethoxy)phenyl]propanedioic acid (i.e. the product of Step C) (0.17 g, 0.66 mmol) in dichloromethane (0.2 mL) containing a catalytic amount of N,N-dimethylformamide. The reaction mixture was stirred for an additional 10 min during which time gas evolution ceased. The reaction mixture was briefly concentrated under vacuum at ambient temperature. The resultant oil was taken up in dichloromethane (2 mL) and added to a solution of 6-chloro-N-2-thiazolyl-3-pyridinemethanamine (i.e. the product of Step B) (0.23 g, 1.02 mmol) and triethylamine (0.40 g, 3.37 mmol) in dichloromethane (4 mL) at 0° C. After stirring for 15 min, the reaction mixture was concentrated, and the resultant residue was purified by chromatography on silica gel using 50-100% ethyl acetate/hexane as eluant to give the title compound as a solid (0.19 g).

$^1$H NMR (CDCl$_3$) δ 8.50 (s, 1H), 8.25 (d, 1H), 7.87 (d, 1H), 7.75 (d, 1H), 7.70 (s, 1H), 7.41-7.35 (m, 2H), 7.08 (d, 1H), 7.03 (d, 1H), 5.29 (s, 2H).

Synthesis Example 5

Preparation of 1-[(6-chloro-3-pyridinyl)methyl]-2-hydroxy-4-oxo-3-phenyl-4H-pyrido[1,2-a]pyrimidinium inner salt Step A: Preparation of N-[(6-chloro-3-pyridinyl)methyl]-2-phenyl-N-(2-pyridinyl)malonamic acid ethyl ester 2-Phenylmalonic acid monoethyl ester was prepared following the procedure in *Journal of Organic Chemistry* 2000, 65, 5834-5836. 2-Phenylmalonic acid monoethyl ester (1.02 g, 5.0 mmol) was dissolved in anhydrous dichloromethane (10 mL), and oxalyl chloride (0.52 mL, 6.0 mmol) was added, followed by one drop of N,N-dimethylformamide. The reaction mixture was stirred for 30 min, then concentrated, redissolved in anhydrous dichloromethane (5 mL) and added to a solution of 6-chloro-N-2-pyridinyl-3-pyridinemethanamine (i.e. the product of Example 2, Step A) (1.1 g, 5.0 mmol) and triethyl amine (0.83 mL, 6.0 mmol) in anhydrous dichloromethane (5 mL) at 0° C. The stirred reaction mixture was allowed to warm to room temperature over 30 min. The reaction mixture was poured onto a silica gel cartridge (Bond Elute® manufactured by Varian) and purified using a gradient of 0-50% ethyl acetate/hexanes. A mixture of desired product and starting amine was isolated (1.3 g of 33 mol % recovered amine/67 mol % desired product). 2-Phenylmalonic acid monoethyl ester (0.54 g, 2.6 mmol) was dissolved in anhydrous dichloromethane (3 mL), and oxalyl chloride (0.26 mL, 3.0 mmol) was added, followed by one drop of N,N-dimethylformamide. The reaction mixture was stirred until gas evolution ceased and then concentrated, redissolved in anhydrous dichloromethane (3 mL) and added to the mixture of recovered amine and desired product isolated previously. The reaction mixture was stirred for 30 min and then concentrated, and the crude residue was chromatographed as already described to give the title compound as a solid (0.9 g).

$^1$H NMR (CDCl$_3$) δ 8.50 (m, 1H), 8.18 (s, 1H), 7.60-7.75 (m, 2H), 7.2-7.3 (m, 5H), 7.13 (m, 2H), 6.87 (s, 1H), 5.13-4.88 (dd, 2H), 4.86 (s, 1H), 4.16 (m, 2H), 1.22 (t, 3H).

Step B: Preparation of 1-[(6-chloro-3-pyridinyl)methyl]-2-hydroxy-4-oxo-3-phenyl-4H-pyrido[1,2-a]pyrimidinium inner salt N-[(6-chloro-3-pyridinyl)methyl]-2-phenyl-N-(2-pyridinyl)malonamic acid ethyl ester (i.e. the product of Step A) (200 mg, 0.49 mmol) was added to tetralin (0.5 mL) and heated at 200° C. for 30 min. The reaction mixture was cooled and concentrated, and the resulting residue was purified by chromatography on silica gel using 50-100% ethyl acetate/hexane as eluant to give the title compound as a solid (15 mg).

$^1$H NMR (CDCl$_3$) δ 9.55 (dd, 1H), 8.47 (d, 1H), 8.04 (m, 1H), 7.98 (d, 2H), 7.70 (dd, 1H), 7.2-7.4 (m, 6H), 5.58 (s, 2H).

Synthesis Example 6

Preparation of 1-[(2-chloro-5-thiazolyl)methyl]-3-[2'-chloro-4'-(trifluoromethyl)[1,1'-biphenyl]-3-yl]-2-hydroxy-4-oxo-4H-pyrido[1,2-a]pyrimidinium inner salt

Step A: Preparation of diethyl 2-(3-bromophenyl)propanedioate

Cesium carbonate (15 g), CuI (290 mg) and 2-picolinic acid (400 mg) were added to a dried flask under a nitrogen atmosphere, and the flask was again purged with nitrogen. 3-Bromoiodobenzene (8.46 g), diethyl malonate (9.6 mL) and dioxane (50 mL) were then added under a nitrogen atmosphere, and the reaction mixture was vigorously stirred at 50° C. overnight. The reaction mixture was then cooled to room temperature, and saturated aqueous ammonium chloride solution was added. The reaction mixture was extracted with ethyl acetate, and the organic phase was separated, washed with brine, dried over magnesium sulfate, and concentrated under vacuum to yield 10.5 g of the title compound containing approximately 25% diethyl malonate. $^1$H NMR (CDCl$_3$) δ 7.47 (s, 1H), 7.33 (d, 1H), 7.24 (d, 1H), 7.10 (t, 1H), 4.49 (s, 1H), 4.09 (q, 4H), 1.14 (t, 6H).

Step B: Preparation of 1,3-diethyl 2-[2'-chloro-4'-(trifluoromethyl) [1,1'-biphenyl]-3-yl]propanedioate Diethyl 2-(3-bromophenyl)propanedioate (3.75 g), 2-chloro-4-(trifluoromethyl)phenyl boronic acid (4.0 g), dioxane (10 mL), 2M aqueous sodium carbonate solution (5 mL) and dichlorobis(triphenylphosphine)palladium(II) (422 mg) were added to a vial, and the reaction mixture was heated at 80° C. for 30 minutes. The reaction mixture was then cooled, poured into water, extracted with ethyl acetate, and the organic phase was separated and concentrated under vacuum in the presence of Celite® (diatomaceous earth) to yield a crude solid. The crude solid was purified by medium pressure liquid chromatography on silica gel eluting with a gradient of ethyl acetate in hexanes to yield 3.2 g of the title compound. $^1$H NMR (CDCl$_3$) δ 7.74 (s, 1H), 7.57 (d, 1H), 7.37-7.50 (m, 5H), 4.57 (s, 1H), 4.23 (q, 4H), 1.27 (t, 6H).

Step C: Preparation of 1,3-bis(2,4,6-trichlorophenyl) 2-[2'-chloro-4'-(trifluoromethyl)[1,1'-biphenyl]-3-yl]propanedioate 1,3-Diethyl 2-[2'-chloro-4'-(trifluoromethyl)[1,1'-biphenyl]-3-yl]propanedioate (3.0 g) was added to 10% aqueous sodium hydroxide solution (20 mL) at 50° C., and the reaction mixture was stirred vigorously for 20 min. The reaction mixture was then cooled in an ice/acetone bath, and was acidified with concentrated aqueous hydrochloric acid while keeping the reaction temperature below 10° C. The reaction mixture was extracted with diethyl ether, and the separated ether phase was dried over magnesium sulfate and concentrated under vacuum to yield a crude product. $^1$H NMR (acetone-d$_6$) δ 7.89 (s, 1H), 7.79 (d, 1H), 7.67 (d, 2H), 7.60 (m, 1H), 7.45-7.55 (m, 2H), 4.88 (s, 1H).

The crude product obtained above was dissolved in anhydrous dichloromethane (50 mL), and N,N-dimethylformamide (3 drops) was added, followed by oxalyl chloride (2.54 mL). The reaction mixture was stirred under nitrogen for 90 min, and then concentrated under vacuum. The resulting oil was redissolved in anhydrous dichloromethane (6 mL), and 2,4,6-trichlorophenol (3.57 g) was added. The reaction mixture was stirred overnight, and then the solvent was removed under vacuum to yield a crude solid. The crude solid was triturated with two 40 mL portions of ice-cold methanol to yield a white solid which was dried under vacuum overnight to provide 2.9 g of the title compound as a white solid. $^1$H NMR (CDCl$_3$) δ 7.76 (s, 1H), 7.71 (d, 2H), 7.45-7.6 (m, 4H), 7.37 (s, 4H), 5.38 (s, 1H).

Step D: Preparation of 1-[(2-chloro-5-thiazolyl)methyl]-3-[2'-chloro-4'-(trifluoromethyl)[1,1'-biphenyl]-3-yl]-2-hydroxy-4-oxo-4H-pyrido[1,2-c]pyrimidinium inner salt bis-trichlorophenyl biphenyl malonate ester (0.72 g), N-[(2-chloro-5-thiazolyl)methyl]-2-pyridinamine (0.23 g, prepared by the method described in WO 09/099,929) and toluene (1 mL) were heated at 80° C. for 3 h, and then stirred at room temperature overnight. The reaction mixture was then poured into diethyl ether and filtered to isolate a solid. The solid was triturated with diethyl ether, and then heated in boiling diethyl ether for 1 h. The resulting suspension was filtered, and the isolated solid was dried to yield 0.50 g of the title compound, a compound of this invention, as a yellow solid. $^1$H NMR (CDCl$_3$) δ 9.56 (d, 1H), 8.15 (t, 1H), 7.90 (d, 2H), 7.73 (s, 1H), 7.66 (s, 1H), 7.60 (d, 1H), 7.56 (s, 2H), 7.50 (t, 1H), 7.41 (t, 1H), 7.39 (d, 1H), 5.60 (br s, 2H).

Alternative preparation of 1,3-diethyl 2-[2'-chloro-4'-(trifluoromethyl)[1,1'-biphenyl]-3-yl]propanedioate

Step A: Preparation of ethyl 2'-chloro-4'-(trifluoromethyl)[1,1'-biphenyl]-3-acetate Ethyl 3-iodophenylacetate (2.90 g), 2-chloro-4-(trifluoromethyl)phenyl boronic acid (3.3 g), 2M aqueous sodium carbonate solution (5 mL), dioxane (10 mL) and dichloro-bis(triphenylphosphine)palladium(II) (350 mg) were heated at 80° C. for 30 min with stirring. The reaction mixture was then cooled, poured into water, extracted with ethyl acetate, and the organic layer was separated and concentrated under vacuum in the presence of Celite® to a solid residue. This solid residue was purifed by medium pressure liquid chromatography on silica gel eluting with a gradient of ethyl acetate in hexanes to yield 1.7 g of the title compound. $^1$H NMR (CDCl$_3$) δ 7.14 (s, 1H), 7.56 (d, 1H) 7.30-7.45 (m, 5H), 4.77 (q, 2H), 3.67 (s, 2H), 1.26 (t, 3H).

Step B: Preparation of 1,3-diethyl 2-[2'-chloro-4'-(trifluoromethyl)[1,1'-biphenyl]-3-yl]propanedioate NaH (1.2 g, 60% dispersion in mineral oil) was added to the product of Step A dissolved in diethyl carbonate (10 mL). The reaction mixture was stirred overnight and then cautiously quenched by careful addition to saturated aqueous ammonium chloride solution. The quenched reaction mixture was extracted with ethyl acetate, and the separated orgranic phase was dried and concentrated under vacuum to yield 2.1 g of the title compound containing approximately 30% diethyl carbonate. $^1$H NMR (CDCl$_3$) δ 7.74 (s, 1H), 7.57 (d, 1H), 7.35-7.55 (m, 5H), 4.57 (s, 1H) 4.19 (q, 4H), 1.29 (t, 6H).

Synthesis Example 7

Preparation of 1-[(2-chloro-5-thiazolyl)methyl]-3-(3,5-dimethoxyphenyl)-2-hydroxy-4-oxo-4H-pyrido[1,2-a]pyrimidinium inner salt

Step A: Preparation of phenyl 3,5-dimethoxybenzeneacetate

To a slurry of 3,5-dimethoxybenzeneacetic acid (51.5 g) and N,N-dimethylformamide (0.5 mL) in dichloromethane (110 mL) cooled in an ice bath was added dropwise a solution of oxalyl chloride (41.0 g) in dichloromethane (30 mL). The resulting solution was stirred at room temperature for 5 h, and then the solvent was removed under vacuum. A solution of phenol (23.9 g) in dichloromethane (80 mL) was added, and the reaction mixture was stirred at room temperature for 22 h. A saturated aqueous solution of sodium bicarbonate was added, and the reaction mixture was stirred for 0.5 h. The organic layer was separated, dried over anhydrous potassium carbonate, and then eluted through a short column of silica gel (100 g) with dichloromethane. The first 400 mL of eluent was concentrated under vacuum to yield 65 g of the title compound. $^1$H NMR (CDCl$_3$) δ 7.35 (t, 2H), 7.20 (q, 1H), 7.05 (d, 2H), 6.53 (s, 2H), 6.40 (s, 1H), 3.79 (s, 6H), 3.78 (s, 2H).

Step B: Preparation of 1,3-diphenyl 2-(3,5-dimethoxyphenyl)propanedioate

To a solution of lithium bis(trimethylsilyl)amide (400 mL, 1M in tetrahydrofuran obtained commercially from Aldrich Chem. Co.) was added a solution of 3,5-dimethoxybenzeneacetic acid phenyl ester (53.1 g) in tetrahydrofuran (65 mL) dropwise over 20 min while cooling in a dry ice bath at –70° C. The resulting slurry was stirred at dry ice temperature for 45 min. Phenyl chloroformate (26 mL) was added all at once followed by 50 mL of tetrahydrofuran. The resulting thick slurry was stirred for 2.5 h at 0° C. while cooling in an ice bath before quenching with diluted aqueous HCl (50 mL of conc. HCl diluted to 150 mL with water). The bulk of tetrahydrofuran was removed under vacuum and diethyl ether (550 mL) and water (80 mL) were added. The aqueous layer was separated and extracted with diethyl ether (50 mL). The combined ether layers were dried over magnesium sulfate and concentrated under vacuum to yield a crude solid which was stirred with hexane (250 mL) for 24 h. The solid was then collected by filtration, washed with hexane (100 mL), and vacuum dried to yield 62 g of the title compound. $^1$H NMR (CDCl$_3$) δ 7.37 (t, 2H), 7.26 (q, 1H), 7.13 (d, 2H), 6.73 (s, 2H), 6.45 (s, 1H), 5.02 (s, 1H), 3.82 (s, 6H).

Step C: Preparation of 1-[(2-chloro-5-thiazolyl)methyl]-3-(3,5-dimethoxyphenyl)-2-hydroxy-4-oxo-4H-pyrido[1,2-a]pyrimidinium inner salt 1,3-diphenyl 2-(3,5-dimethoxyphenyl)propanedioate (77.7 g), N-[(2-chloro-5-thiazolyl)methyl]-2-pyridinamine (34.5 g, prepared by the method described in WO 09/099,929) and toluene (200 mL) were heated at 100° C. for 22 h, and then cooled and stirred at 0° C. for 3 h. The resulting solid was collected by vacuum filtration and washed with diethyl ether (500 mL). More solid precipitated upon mixing of the ether washes with the filtrate, and was collected by vacuum filtration and further washed with diethyl ether. The two batches of solid were combined and dried under vacuum to yield 64 g of the title compound, a compound of this invention, as a yellow solid. $^1$H NMR (DMSO-d$_6$) δ 9.30 (d, 1H), 8.35 (t, 1H), 8.15 (d, 2H), 8.00 (s, 1H), 7.53 (t, 1H), 6.93 (s, 2H), 6.37 (s, 1H), 5.62 (s, 2H), 3.74 (s, 6H).

By the procedures described herein together with methods known in the art, the following compounds of Tables 1 to 30 can be prepared. The following abbreviations are used in Tables 1 to 30 which follow: Me means methyl, Et means ethyl and Pr means propyl.

Tables 1-15 pertain to the structure of Formula T-1 shown below.

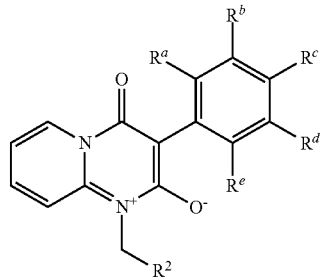

T-1

TABLE 1

| $R^b$, $R^c$, $R^d$ and $R^e$ are H; $R^2$ is 2-chloro-5-thiazolyl | | | |
|---|---|---|---|
| $R^a$ | $R^a$ | $R^a$ | $R^a$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |
| $R^a$, $R^c$, $R^d$ and $R^e$ are H; $R^2$ is 2-chloro-5-thiazolyl | | | |
| $R^b$ | $R^b$ | $R^b$ | $R^b$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |

TABLE 1-continued

| | | | |
|---|---|---|---|
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| $R^a$, $R^b$, $R^d$ and $R^e$ are H; $R^2$ is 2-chloro-5-thiazolyl | | | |
|---|---|---|---|
| $R^c$ | $R^c$ | $R^c$ | $R^c$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| $R^a$ is F; $R^c$, $R^d$ and $R^e$ are H; $R^2$ is 2-chloro-5-thiazolyl | | | |
|---|---|---|---|
| $R^b$ | $R^b$ | $R^b$ | $R^b$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| $R^a$ is F; $R^b$, $R^d$ and $R^e$ are H; $R^2$ is 2-chloro-5-thiazolyl | | | |
|---|---|---|---|
| $R^c$ | $R^c$ | $R^c$ | $R^c$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

TABLE 1-continued

| R$^a$ is F; R$^b$, R$^c$ and R$^e$ are H; R$^2$ is 2-chloro-5-thiazolyl | | | |
|---|---|---|---|
| R$^d$ | R$^d$ | R$^d$ | R$^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
|  |  |  | 2-chloro-5-(CF$_3$)phenyl |

| R$^a$ is F; R$^b$, R$^c$ and R$^d$ are H; R$^2$ is 2-chloro-5-thiazolyl | | | |
|---|---|---|---|
| R$^e$ | R$^e$ | R$^e$ | R$^e$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
|  |  |  | 2-chloro-5-(CF$_3$)phenyl |

| R$^a$ is Cl; R$^c$, R$^d$ and R$^e$ are H; R$^2$ is 2-chloro-5-thiazolyl | | | |
|---|---|---|---|
| R$^b$ | R$^b$ | R$^b$ | R$^b$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
|  |  |  | 2-chloro-5-(CF$_3$)phenyl |

| R$^a$ is Cl; R$^b$, R$^d$ and R$^e$ are H; R$^2$ is 2-chloro-5-thiazolyl | | | |
|---|---|---|---|
| R$^c$ | R$^c$ | R$^c$ | R$^c$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |

TABLE 1-continued

| | | | |
|---|---|---|---|
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| $R^a$ is Cl; $R^b$, $R^c$ and $R^e$ are H; $R^2$ is 2-chloro-5-thiazolyl | | | |
|---|---|---|---|
| $R^d$ | $R^d$ | $R^d$ | $R^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| $R^a$ is Cl; $R^b$, $R^c$ and $R^d$ are H; $R^2$ is 2-chloro-5-thiazolyl | | | |
|---|---|---|---|
| $R^e$ | $R^e$ | $R^e$ | $R^e$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| $R^a$ is OMe; $R^c$, $R^d$, $R^e$ are H; $R^2$ is 2-chloro-5-thiazolyl | | | |
|---|---|---|---|
| $R^b$ | $R^b$ | $R^b$ | $R^b$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| $R^a$ is OMe; $R^b$, $R^d$, $R^e$ are H; $R^2$ is 2-chloro-5-thiazolyl | | | |
|---|---|---|---|
| $R^c$ | $R^c$ | $R^c$ | $R^c$ |
| H | OMe | 4-chlorophenyl | 2-fluoro-4-cyanophenyl |
| F | OEt | 4-(CF$_3$)phenyl | 2-fluoro-4-chlorophenyl |

TABLE 1-continued

| | | | |
|---|---|---|---|
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^a$ is OMe; R$^b$, R$^c$ and R$^e$ are H; R$^2$ is 2-chloro-5-thiazolyl | | | |
|---|---|---|---|
| R$^d$ | R$^d$ | R$^d$ | R$^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^a$ is OMe; R$^b$, R$^c$ and R$^d$ are H; R$^2$ is 2-chloro-5-thiazolyl | | | |
|---|---|---|---|
| R$^e$ | R$^e$ | R$^e$ | R$^e$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^a$ is Me; R$^c$, R$^d$ and R$^e$ are H; R$^2$ is 2-chloro-5-thiazolyl | | | |
|---|---|---|---|
| R$^b$ | R$^b$ | R$^b$ | R$^b$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |

TABLE 1-continued

| | | | |
|---|---|---|---|
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is Me; R$^b$, R$^d$ and R$^e$ are H; R$^2$ is 2-chloro-5-thiazolyl

| R$^c$ | R$^c$ | R$^c$ | R$^c$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is Me; R$^b$, R$^c$ and R$^e$ are H; R$^2$ is 2-chloro-5-thiazolyl

| R$^d$ | R$^d$ | R$^d$ | R$^d$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is Me; R$^b$, R$^c$ and R$^d$ are H; R$^2$ is 2-chloro-5-thiazolyl

| R$^e$ | R$^e$ | R$^e$ | R$^e$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^d$ is Cl; R$^a$, R$^c$ and R$^e$ are H; R$^2$ is 2-chloro-5-thiazolyl

| R$^b$ | R$^b$ | R$^b$ | R$^b$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |

TABLE 1-continued

| | | | |
|---|---|---|---|
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^d$ is CF$_3$; R$^a$, R$^c$ and R$^e$ are H; R$^2$ is 2-chloro-5-thiazolyl | | | |
|---|---|---|---|
| R$^b$ | R$^b$ | R$^b$ | R$^b$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^b$ is Br; R$^a$, R$^c$ and R$^e$ are H; R$^2$ is 2-chloro-5-thiazolyl | | | |
|---|---|---|---|
| R$^d$ | R$^d$ | R$^d$ | R$^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^b$ is OCF$_3$; R$^a$, R$^c$ and R$^e$ are H; R$^2$ is 2-chloro-5-thiazolyl | | | |
|---|---|---|---|
| R$^d$ | R$^d$ | R$^d$ | R$^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

TABLE 1-continued

| | | | |
|---|---|---|---|
| $R^b$ is $OCH_3$; $R^a$, $R^c$ and $R^e$ are H; $R^2$ is 2-chloro-5-thiazolyl | | | |
| $R^d$ | $R^d$ | $R^d$ | $R^d$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |
| 3-chlorophenyl | 3-($OCF_3$)phenyl | 2,4-dichlorophenyl | 2,5-dichlorophenyl |
| 3-($CF_3$)phenyl | 4-fluorophenyl | 2,4-difluorophenyl | 2-fluoro-5-($OCF_3$)phenyl |
| | | | 2-chloro-5-($CF_3$)phenyl |

| | | | |
|---|---|---|---|
| $R^b$ is F; $R^a$, $R^c$ and $R^e$ are H; $R^2$ is 2-chloro-5-thiazolyl | | | |
| $R^d$ | $R^d$ | $R^d$ | $R^d$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |
| 3-chlorophenyl | 3-($OCF_3$)phenyl | 2,4-dichlorophenyl | 2,5-dichlorophenyl |
| 3-($CF_3$)phenyl | 4-fluorophenyl | 2,4-difluorophenyl | 2-fluoro-5-($OCF_3$)phenyl |
| | | | 2-chloro-5-($CF_3$)phenyl |

| | | | |
|---|---|---|---|
| $R^b$ is I; $R^a$, $R^c$ and $R^e$ are H; $R^2$ is 2-chloro-5-thiazolyl | | | |
| $R^d$ | $R^d$ | $R^d$ | $R^d$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |
| 3-chlorophenyl | 3-($OCF_3$)phenyl | 2,4-dichlorophenyl | 2,5-dichlorophenyl |
| 3-($CF_3$)phenyl | 4-fluorophenyl | 2,4-difluorophenyl | 2-fluoro-5-($OCF_3$)phenyl |
| | | | 2-chloro-5-($CF_3$)phenyl |

| | | | |
|---|---|---|---|
| $R^b$ is $CH_3$; $R^a$, $R^c$ and $R^e$ are H; $R^2$ is 2-chloro-5-thiazolyl | | | |
| $R^d$ | $R^d$ | $R^d$ | $R^d$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |

TABLE 1-continued

| | | | |
|---|---|---|---|
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^b$ is cyano; R$^a$, R$^c$ and R$^e$ are H; R$^2$ is 2-chloro-5-thiazolyl

| R$^d$ | R$^d$ | R$^d$ | R$^d$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^c$ is F; R$^a$, R$^b$ and R$^e$ are H; R$^2$ is 2-chloro-5-thiazolyl

| R$^d$ | R$^d$ | R$^d$ | R$^d$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^c$ is Cl; R$^a$, R$^b$ and R$^e$ are H; R$^2$ is 2-chloro-5-thiazolyl

| R$^d$ | R$^d$ | R$^d$ | R$^d$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^c$ is CH$_3$; R$^a$, R$^b$ and R$^e$ are H; R$^2$ is 2-chloro-5-thiazolyl

| R$^d$ | R$^d$ | R$^d$ | R$^d$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |

TABLE 1-continued

| | | | |
|---|---|---|---|
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |
| 3-chlorophenyl | 3-($OCF_3$)phenyl | 2,4-dichlorophenyl | 2,5-dichlorophenyl |
| 3-($CF_3$)phenyl | 4-fluorophenyl | 2,4-difluorophenyl | 2-fluoro-5-($OCF_3$)phenyl |
| | | | 2-chloro-5-($CF_3$)phenyl |

| $R^c$ is $OCH_3$; $R^a$, $R^b$ and $R^e$ are H; $R^2$ is 2-chloro-5-thiazolyl | | | |
|---|---|---|---|
| $R^d$ | $R^d$ | $R^d$ | $R^d$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |
| 3-chlorophenyl | 3-($OCF_3$)phenyl | 2,4-dichlorophenyl | 2,5-dichlorophenyl |
| 3-($CF_3$)phenyl | 4-fluorophenyl | 2,4-difluorophenyl | 2-fluoro-5-($OCF_3$)phenyl |
| | | | 2-chloro-5-($CF_3$)phenyl |

| $R^a$ and $R^b$ are F; $R^c$ and $R^e$ are H; $R^2$ is 2-chloro-5-thiazolyl | | | |
|---|---|---|---|
| $R^d$ | $R^d$ | $R^d$ | $R^d$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |
| 3-chlorophenyl | 3-($OCF_3$)phenyl | 2,4-dichlorophenyl | 2,5-dichlorophenyl |
| 3-($CF_3$)phenyl | 4-fluorophenyl | 2,4-difluorophenyl | 2-fluoro-5-($OCF_3$)phenyl |
| | | | 2-chloro-5-($CF_3$)phenyl |

| $R^a$ is F; $R^b$ is Cl; $R^c$ and $R^e$ are H; $R^2$ is 2-chloro-5-thiazolyl | | | |
|---|---|---|---|
| $R^d$ | $R^d$ | $R^d$ | $R^d$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |

TABLE 1-continued

| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^a$ and R$^e$ are F; R$^c$ and R$^d$ are H; R$^2$ is 2-chloro-5-thiazolyl | | | |
|---|---|---|---|
| R$^b$ | R$^b$ | R$^b$ | R$^b$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fruoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

Table 2

Table 2 is identical to Table 1, except that R$^2$ is 6-chloro-3-pyridinyl. For example, the first compound in Table 2 is the compound of Formula T-1 wherein R$^a$, R$^b$, R$^c$, R$^d$ and R$^e$ are H; and R$^2$ is 6-chloro-3-pyridinyl.

Table 3

Table 3 is identical to Table 1, except that R$^2$ is 6-bromo-3-pyridinyl. For example, the first compound in Table 3 is the compound of Formula T-1 wherein R$^a$, R$^b$, R$^c$, R$^d$ and R$^e$ are H; and R$^2$ is 6-bromo-3-pyridinyl.

Table 4

Table 4 is identical to Table 1, except that R$^2$ is 6-methyl-3-pyridinyl. For example, the first compound in Table 4 is the compound of Formula T-1 wherein R$^a$, R$^b$, R$^c$, R$^d$ and R$^e$ are H; and R$^2$ is 6-methyl-3-pyridinyl.

Table 5

Table 5 is identical to Table 1, except that R$^2$ is 3-pyridinyl. For example, the first compound in Table 5 is the compound of Formula T-1 wherein R$^a$, R$^b$, R$^c$, R$^d$ and R$^e$ are H; and R$^2$ is 3-pyridinyl.

Table 6

Table 6 is identical to Table 1, except that R$^2$ is 5-thiazolyl. For example, the first compound in Table 6 is the compound of Formula T-1 wherein R$^a$, R$^b$, R$^c$, R$^d$ and R$^e$ are H; and R$^2$ is 5-thiazolyl.

Table 7

Table 7 is identical to Table 1, except that R$^2$ is 2-methyl-5-thiazolyl. For example, the first compound in Table 7 is the compound of Formula T-1 wherein R$^a$, R$^b$, R$^c$, R$^d$ and R$^e$ are H; and R$^2$ is 2-methyl-5-thiazolyl.

Table 8

Table 8 is identical to Table 1, except that R$^2$ is 6-fluoro-3-pyridinyl. For example, the first compound in Table 8 is the compound of Formula T-1 wherein R$^a$, R$^b$, R$^c$, R$^d$ and R$^e$ are H; and R$^2$ is 6-fluoro-3-pyridinyl.

Table 9

Table 9 is identical to Table 1, except that R$^2$ is 2-bromo-5-thiazolyl. For example, the first compound in Table 9 is the compound of Formula T-1 wherein R$^a$, R$^b$, R$^c$, R$^d$ and R$^e$ are H; and R$^2$ is 2-bromo-5-thiazolyl.

Table 10

Table 10 is identical to Table 1, except that R$^2$ is 2-fluoro-5-thiazolyl. For example, the first compound in Table 10 is the compound of Formula T-1 wherein R$^a$, R$^b$, R$^c$, R$^d$ and R$^e$ are H; and R$^2$ is 2-fluoro-5-thiazolyl.

Table 11

Table 11 is identical to Table 1, except that R$^2$ is 5-pyrimidinyl. For example, the first compound in Table 11 is the compound of Formula T-1 wherein R$^a$, R$^b$, R$^c$, R$^d$ and R$^e$ are H; and R$^2$ is 5-pyrimidinyl.

Table 12

Table 12 is identical to Table 1, except that R$^2$ is 2-methyl-5-pyrimidinyl. For example, the first compound in Table 12 is the compound of Formula T-1 wherein R$^a$, R$^b$, R$^c$, R$^d$ and R$^e$ are H; and R$^2$ is 2-methyl-5-pyrimidinyl.

Table 13

Table 13 is identical to Table 1, except that R$^2$ is CF$_3$. For example, the first compound in Table 13 is the compound of Formula T-1 wherein R$^a$, R$^b$, R$^c$, R$^d$ and R$^e$ are H; and R$^2$ is CF$_3$.

Table 14

Table 14 is identical to Table 1, except that $R^2$ is $CH_2CF_3$. For example, the first compound in Table 14 is the compound of Formula T-1 wherein $R^a$, $R^b$, $R^c$, $R^d$ and $R^e$ are H; and $R^2$ is $CH_2CF_3$.

Table 15

Table 15 is identical to Table 1, except that $R^2$ is $CH_2CFClF_2H$. For example, the first compound in Table 15 is the compound of Formula T-1 wherein $R^a$, $R^b$, $R^c$, $R^d$ and $R^e$ are H; and $R^2$ is $CH_2CFClF_2H$.

Tables 16-30 pertain to the structure of Formula T-2 shown below.

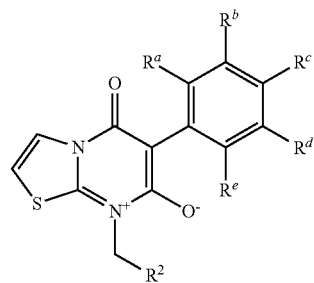

T-2

TABLE 16

| $R^b$, $R^c$, $R^d$ and $R^e$ are H; $R^2$ is 2-chloro-5-thiazolyl | | | |
|---|---|---|---|
| $R^a$ | $R^a$ | $R^a$ | $R^a$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |
| 3-chlorophenyl | 3-($OCF_3$)phenyl | 2,4-dichlorophenyl | 2,5-dichlorophenyl |
| 3-($CF_3$)phenyl | 4-fluorophenyl | 2,4-difluorophenyl | 2-fluoro-5-($OCF_3$)phenyl |
| | | | 2-chloro-5-($CF_3$)phenyl |

| $R^a$, $R^c$, $R^d$ and $R^e$ are H; $R^2$ is 2-chloro-5-thiazolyl | | | |
|---|---|---|---|
| $R^b$ | $R^b$ | $R^b$ | $R^b$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |
| 3-chlorophenyl | 3-($OCF_3$)phenyl | 2,4-dichlorophenyl | 2,5-dichlorophenyl |
| 3-($CF_3$)phenyl | 4-fluorophenyl | 2,4-difluorophenyl | 2-fluoro-5-($OCF_3$)phenyl |
| | | | 2-chloro-5-($CF_3$)phenyl |

| $R^a$, $R^b$, $R^d$ and $R^e$ are H; $R^2$ is 2-chloro-5-thiazolyl | | | |
|---|---|---|---|
| $R^c$ | $R^c$ | $R^c$ | $R^c$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |

TABLE 16-continued

| | | | |
|---|---|---|---|
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is F; R$^c$, R$^d$ and R$^e$ are H; R$^2$ is 2-chloro-5-thiazolyl

| R$^b$ | R$^b$ | R$^b$ | R$^b$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is F; R$^b$, R$^d$ and R$^e$ are H; R$^2$ is 2-chloro-5-thiazolyl

| R$^c$ | R$^c$ | R$^c$ | R$^c$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is F; R$^b$, R$^c$ and R$^e$ are H; R$^2$ is 2-chloro-5-thiazolyl

| R$^d$ | R$^d$ | R$^d$ | R$^d$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is F; R$^b$, R$^c$ and R$^d$ are H; R$^2$ is 2-chloro-5-thiazolyl

| R$^e$ | R$^e$ | R$^e$ | R$^e$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |

TABLE 16-continued

| | | | |
|---|---|---|---|
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^a$ is Cl; R$^c$, R$^d$ and R$^e$ are H; R$^2$ is 2-chloro-5-thiazolyl | | | |
|---|---|---|---|
| R$^b$ | R$^b$ | R$^b$ | R$^b$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^a$ is Cl; R$^b$, R$^d$ and R$^e$ are H; R$^2$ is 2-chloro-5-thiazolyl | | | |
|---|---|---|---|
| R$^c$ | R$^c$ | R$^c$ | R$^c$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^a$ is Cl; R$^b$, R$^c$ and R$^e$ are H; R$^2$ is 2-chloro-5-thiazolyl | | | |
|---|---|---|---|
| R$^d$ | R$^d$ | R$^d$ | R$^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

TABLE 16-continued

| $R^a$ is Cl; $R^b$, $R^c$ and $R^d$ are H; $R^2$ is 2-chloro-5-thiazolyl | | | |
|---|---|---|---|
| $R^e$ | $R^e$ | $R^e$ | $R^e$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
|  |  |  | 2-chloro-5-(CF$_3$)phenyl |

| $R^a$ is OMe; $R^c$, $R^d$, $R^e$ are H; $R^2$ is 2-chloro-5-thiazolyl | | | |
|---|---|---|---|
| $R^b$ | $R^b$ | $R^b$ | $R^b$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
|  |  |  | 2-chloro-5-(CF$_3$)phenyl |

| $R^a$ is OMe; $R^b$, $R^d$, $R^e$ are H; $R^2$ is 2-chloro-5-thiazolyl | | | |
|---|---|---|---|
| $R^c$ | $R^c$ | $R^c$ | $R^c$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
|  |  |  | 2-chloro-5-(CF$_3$)phenyl |

| $R^a$ is OMe; $R^b$, $R^c$ and $R^e$ are H; $R^2$ is 2-chloro-5-thiazolyl | | | |
|---|---|---|---|
| $R^d$ | $R^d$ | $R^d$ | $R^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |

TABLE 16-continued

| | | | |
|---|---|---|---|
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is OMe; R$^b$, R$^c$ and R$^d$ are H; R$^2$ is 2-chloro-5-thiazolyl

| R$^e$ | R$^e$ | R$^e$ | R$^e$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is Me; R$^c$, R$^d$ and R$^e$ are H; R$^2$ is 2-chloro-5-thiazolyl

| R$^b$ | R$^b$ | R$^b$ | R$^b$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is Me; R$^b$, R$^d$ and R$^e$ are H; R$^2$ is 2-chloro-5-thiazolyl

| R$^c$ | R$^c$ | R$^c$ | R$^c$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is Me; R$^b$, R$^c$ and R$^e$ are H; R$^2$ is 2-chloro-5-thiazolyl

| R$^d$ | R$^d$ | R$^d$ | R$^d$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |

TABLE 16-continued

| | | | |
|---|---|---|---|
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^a$ is Me; R$^b$, R$^c$ and R$^d$ are H; R$^2$ is 2-chloro-5-thiazolyl

| R$^e$ | R$^e$ | R$^e$ | R$^e$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^d$ is Cl; R$^a$, R$^c$ and R$^e$ are H; R$^2$ is 2-chloro-5-thiazolyl

| R$^b$ | R$^b$ | R$^b$ | R$^b$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

R$^d$ is CF$_3$; R$^a$, R$^c$ and R$^e$ are H; R$^2$ is 2-chloro-5-thiazolyl

| R$^b$ | R$^b$ | R$^b$ | R$^b$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |

TABLE 16-continued

| | | | |
|---|---|---|---|
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

$R^b$ is Br; $R^a$, $R^c$ and $R^e$ are H; $R^2$ is 2-chloro-5-thiazolyl

| $R^d$ | $R^d$ | $R^d$ | $R^d$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

$R^b$ is OCF$_3$; $R^a$, $R^c$ and $R^e$ are H; $R^2$ is 2-chloro-5-thiazolyl

| $R^d$ | $R^d$ | $R^d$ | $R^d$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

$R^b$ is OCH$_3$; $R^a$, $R^c$ and $R^e$ are H; $R^2$ is 2-chloro-5-thiazolyl

| $R^d$ | $R^d$ | $R^d$ | $R^d$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

$R^b$ is F; $R^a$, $R^c$ and $R^e$ are H; $R^2$ is 2-chloro-5-thiazolyl

| $R^d$ | $R^d$ | $R^d$ | $R^d$ |
|---|---|---|---|
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |

TABLE 16-continued

| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
|  |  |  | 2-chloro-5-(CF$_3$)phenyl |

| R$^b$ is I; R$^a$, R$^c$ and R$^e$ are H; R$^2$ is 2-chloro-5-thiazolyl | | | |
|---|---|---|---|
| R$^d$ | R$^d$ | R$^d$ | R$^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
|  |  |  | 2-chloro-5-(CF$_3$)phenyl |

| R$^b$ is CH$_3$; R$^a$, R$^c$ and R$^e$ are H; R$^2$ is 2-chloro-5-thiazolyl | | | |
|---|---|---|---|
| R$^d$ | R$^d$ | R$^d$ | R$^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
|  |  |  | 2-chloro-5-(CF$_3$)phenyl |

| R$^b$ is cyano; R$^a$, R$^c$ and R$^e$ are H; R$^2$ is 2-chloro-5-thiazolyl | | | |
|---|---|---|---|
| R$^d$ | R$^d$ | R$^d$ | R$^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
|  |  |  | 2-chloro-5-(CF$_3$)phenyl |

TABLE 16-continued

| | | | |
|---|---|---|---|
| $R^c$ is F; $R^a$, $R^b$ and $R^e$ are H; $R^2$ is 2-chloro-5-thiazolyl | | | |
| $R^d$ | $R^d$ | $R^d$ | $R^d$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |
| 3-chlorophenyl | 3-($OCF_3$)phenyl | 2,4-dichlorophenyl | 2,5-dichlorophenyl |
| 3-($CF_3$)phenyl | 4-fluorophenyl | 2,4-difluorophenyl | 2-fluoro-5-($OCF_3$)phenyl |
| | | | 2-chloro-5-($CF_3$)phenyl |

| | | | |
|---|---|---|---|
| $R^c$ is Cl; $R^a$, $R^b$ and $R^e$ are H; $R^2$ is 2-chloro-5-thiazolyl | | | |
| $R^d$ | $R^d$ | $R^d$ | $R^d$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |
| 3-chlorophenyl | 3-($OCF_3$)phenyl | 2,4-dichlorophenyl | 2,5-dichlorophenyl |
| 3-($CF_3$)phenyl | 4-fluorophenyl | 2,4-difluorophenyl | 2-fluoro-5-($OCF_3$)phenyl |
| | | | 2-chloro-5-($CF_3$)phenyl |

| | | | |
|---|---|---|---|
| $R^c$ is $CH_3$; $R^a$, $R^b$ and $R^e$ are H; $R^2$ is 2-chloro-5-thiazolyl | | | |
| $R^d$ | $R^d$ | $R^d$ | $R^d$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |
| Pr | $CH_2F$ | 2-fluoro-6-chloro-3-pyridinyl | 2-methyl-4-($CF_3$)phenyl |
| i-Pr | $CHF_2$ | 2,6-dichloro-3-pyridinyl | 2-chloro-4-($CF_3$)phenyl |
| c-Pr | C(=NOMe)Me | 2-bromo-5-chloro-4-pyridinyl | 2-($CF_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-($CF_3$)phenyl |
| 2-fluorophenyl | 3-cyanophenyl | 3-fluoro-4-chlorophenyl | 2-fluoro-5-chlorophenyl |
| 3-chlorophenyl | 3-($OCF_3$)phenyl | 2,4-dichlorophenyl | 2,5-dichlorophenyl |
| 3-($CF_3$)phenyl | 4-fluorophenyl | 2,4-difluorophenyl | 2-fluoro-5-($OCF_3$)phenyl |
| | | | 2-chloro-5-($CF_3$)phenyl |

| | | | |
|---|---|---|---|
| $R^c$ is $OCH_3$; $R^a$, $R^b$ and $R^e$ are H; $R^2$ is 2-chloro-5-thiazolyl | | | |
| $R^d$ | $R^d$ | $R^d$ | $R^d$ |
| H | OMe | 4-chlorophenyl | 2-fluoro-4-cyanophenyl |
| F | OEt | 4-($CF_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-($CF_3$)phenyl |
| I | $OCF_3$ | 6-chloro-3-pyridinyl | 2,4-bis($CF_3$)phenyl |
| cyano | $OCHF_2$ | 6-fluoro-3-pyridinyl | 2-fluoro-4-bromophenyl |
| Me | $OCH_2CF_3$ | 6-($CF_3$)-3-pyridinyl | 2-chloro-4-fluorophenyl |
| Et | $CF_3$ | 4,6-dichloro-3-pyridinyl | 2-($CF_3$)-4-fluorophenyl |

TABLE 16-continued

| | | | |
|---|---|---|---|
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^a$ and R$^b$ are F; R$^c$ and R$^e$ are H; R$^2$ is 2-chloro-5-thiazolyl | | | |
|---|---|---|---|
| R$^d$ | R$^d$ | R$^d$ | R$^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

| R$^a$ is F; R$^b$ is Cl; R$^c$ and R$^e$ are H; R$^2$ is 2-chloro-5-thiazolyl | | | |
|---|---|---|---|
| R$^d$ | R$^d$ | R$^d$ | R$^d$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fluoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF3)phenyl |

| R$^a$ and R$^e$ are F; R$^c$ and R$^d$ are H; R$^2$ is 2-chloro-5-thiazolyl | | | |
|---|---|---|---|
| R$^b$ | R$^b$ | R$^b$ | R$^b$ |
| H | OMe | 4-chlorophenyl | 2-fluoro-4-cyanophenyl |
| F | OEt | 4-(CF$_3$)phenyl | 2-fluoro-4-chlorophenyl |
| Cl | O—n-Pr | 4-cyanophenyl | 2-methyl-4-chlorophenyl |
| Br | O—i-Pr | 4-bromophenyl | 2-fruoro-4-(CF$_3$)phenyl |
| I | OCF$_3$ | 6-chloro-3-pyridinyl | 2,4-bis(CF$_3$)phenyl |
| cyano | OCHF$_2$ | 6-fluoro-3-pyridinyl | 2-fluoro-4-bromophenyl |
| Me | OCH$_2$CF$_3$ | 6-(CF$_3$)-3-pyridinyl | 2-chloro-4-fluorophenyl |
| Et | CF$_3$ | 4,6-dichloro-3-pyridinyl | 2-(CF$_3$)-4-fluorophenyl |
| Pr | CH$_2$F | 2-fluoro-6-chloro-3-pyridinyl | 2-methyl-4-(CF$_3$)phenyl |
| i-Pr | CHF$_2$ | 2,6-dichloro-3-pyridinyl | 2-chloro-4-(CF$_3$)phenyl |
| c-Pr | C(=NOMe)Me | 2-bromo-5-chloro-4-pyridinyl | 2-(CF$_3$)-4-chlorophenyl |
| t-Bu | C(=NOEt)Me | 3-bromo-5-fluorophenyl | 2,5-difluorophenyl |
| phenyl | 3-fluorophenyl | 3-chloro-5-fluorophenyl | 2-fluoro-5-(CF$_3$)phenyl |
| 2-fluorophenyl | 3-cyanophenyl | 3-fluoro-4-chlorophenyl | 2-fluoro-5-chlorophenyl |
| 3-chlorophenyl | 3-(OCF$_3$)phenyl | 2,4-dichlorophenyl | 2,5-dichlorophenyl |
| 3-(CF$_3$)phenyl | 4-fluorophenyl | 2,4-difluorophenyl | 2-fluoro-5-(OCF$_3$)phenyl |
| | | | 2-chloro-5-(CF$_3$)phenyl |

Table 17

Table 17 is identical to Table 16, except that $R^2$ is 6-chloro-3-pyridinyl. For example, the first compound in Table 17 is the compound of Formula T-2 wherein $R^a$, $R^b$, $R^c$, $R^d$ and $R^e$ are H; and $R^2$ is 6-chloro-3-pyridinyl.

Table 18

Table 18 is identical to Table 16, except that $R^2$ is 6-bromo-3-pyridinyl. For example, the first compound in Table 18 is the compound of Formula T-2 wherein $R^a$, $R^b$, $R^c$, $R^d$ and $R^e$ are H; and $R^2$ is 6-bromo-3-pyridinyl.

Table 19

Table 19 is identical to Table 16, except that $R^2$ is 6-methyl-3-pyridinyl. For example, the first compound in Table 19 is the compound of Formula T-2 wherein $R^a$, $R^b$, $R^c$, $R^d$ and $R^e$ are H; and $R^2$ is 6-methyl-3-pyridinyl.

Table 20

Table 20 is identical to Table 16, except that $R^2$ is 3-pyridinyl. For example, the first compound in Table 20 is the compound of Formula T-2 wherein $R^a$, $R^b$, $R^c$, $R^d$ and $R^e$ are H; and $R^2$ is 3-pyridinyl.

Table 21

Table 21 is identical to Table 16, except that $R^2$ is 5-thiazolyl. For example, the first compound in Table 21 is the compound of Formula T-2 wherein $R^a$, $R^b$, $R^c$, $R^d$ and $R^e$ are H; and $R^2$ is 5-thiazolyl.

Table 22

Table 22 is identical to Table 16, except that $R^2$ is 2-methyl-5-thiazolyl. For example, the first compound in Table 22 is the compound of Formula T-2 wherein $R^a$, $R^b$, $R^c$, $R^d$ and $R^e$ are H; and $R^2$ is 2-methyl-5-thiazolyl.

Table 23

Table 23 is identical to Table 16, except that $R^2$ is 6-fluoro-3-pyridinyl. For example, the first compound in Table 23 is the compound of Formula T-2 wherein $R^a$, $R^b$, $R^c$, $R^d$ and $R^e$ are H; and $R^2$ is 6-fluoro-3-pyridinyl.

Table 24

Table 24 is identical to Table 16, except that $R^2$ is 2-bromo-5-thiazolyl. For example, the first compound in Table 24 is the compound of Formula T-2 wherein $R^a$, $R^b$, $R^c$, $R^d$ and $R^e$ are H; and $R^2$ is 2-bromo-5-thiazolyl.

Table 25

Table 25 is identical to Table 16, except that $R^2$ is 2-fluoro-5-thiazolyl. For example, the first compound in Table 25 is the compound of Formula T-2 wherein $R^a$, $R^b$, $R^c$, $R^d$ and $R^e$ are H; and $R^2$ is 2-fluoro-5-thiazolyl.

Table 26

Table 26 is identical to Table 16, except that $R^2$ is 5-pyrimidinyl. For example, the first compound in Table 26 is the compound of Formula T-2 wherein $R^a$, $R^b$, $R^c$, $R^d$ and $R^e$ are H; and $R^2$ is 5-pyrimidinyl.

Table 27

Table 27 is identical to Table 16, except that $R^2$ is 2-methyl-5-pyrimidinyl. For example, the first compound in Table 27 is the compound of Formula T-2 wherein $R^a$, $R^b$, $R^c$, $R^d$ and $R^e$ are H; and $R^2$ is 2-methyl-5-pyrimidinyl.

Table 28

Table 28 is identical to Table 16, except that $R^2$ is $CF_3$. For example, the first compound in Table 28 is the compound of Formula T-2 wherein $R^a$, $R^b$, $R^c$, $R^d$ and $R^e$ are H; and $R^2$ is $CF_3$.

Table 29

Table 29 is identical to Table 16, except that $R^2$ is $CH_2CF_3$. For example, the first compound in Table 29 is the compound of Formula T-1 wherein $R^a$, $R^b$, $R^c$, $R^d$ and $R^e$ are H; and $R^2$ is $CH_2CF_3$.

Table 30

Table 30 is identical to Table 16, except that $R^2$ is $CH_2CFClF_2H$. For example, the first compound in Table 30 is the compound of Formula T-1 wherein $R^a$, $R^b$, $R^c$, $R^d$ and $R^e$ are H; and $R^2$ is $CH_2CFClF_2H$.

TABLE 31

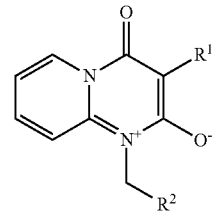

| $R^1$ |
|---|
| $R_2$ is 2-chloro-5-thiazolyl |
| 4-(trifluoromethyl)-2-pyridinyl |
| 6-(trifluoromethyl)-2-pyridinyl |
| 4-(trifluoromethoxy)-2-pyridinyl |
| 4-methyl-2-pyridinyl |
| 2-fluoro-4-pyridinyl |
| 2-chloro-4-pyridinyl |
| 2-bromo-4-pyridinyl |
| 2-cyano-4-pyridinyl |
| 2-(trifluoromethyl)-4-pyridinyl |
| 2-(trifluoromethoxy)-4-pyridinyl |
| 2-methoxy-4-pyridinyl |
| $R^2$ is 6-chloro-3-pyridinyl |
| 4-(trifluoromethyl)-2-pyridinyl |
| 6-(trifluoromethyl)-2-pyridinyl |
| 4-(trifluoromethoxy)-2-pyridinyl |
| 4-methyl-2-pyridinyl |
| 2-fluoro-4-pyridinyl |
| 2-chloro-4-pyridinyl |
| 2-bromo-4-pyridinyl |
| 2-cyano-4-pyridinyl |
| 2-(trifluoromethyl)-4-pyridinyl |

TABLE 31-continued

[Structure: pyrido-pyrimidine with O, R¹, N⁺, O⁻, R² substituents]

R¹

2-(trifluoromethoxy)-4-pyridinyl
2-methoxy-4-pyridinyl
R² is CF₃

4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 6-methyl-3-pyridinyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 6-fluoro-3-pyridinyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 3-pyridinyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 5-thiazolyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl

TABLE 31-continued

[Structure: pyrido-pyrimidine with O, R¹, N⁺, O⁻, R² substituents]

R¹

2-cyano-4-pyridinyl
2-(trifluoromethyl)-4-pyridinyl
2-(trifluoromethoxy)-4-pyridinyl
2-methoxy-4-pyridinyl
R² is 2-methyl-5-thiazolyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 2-fluoro-5-thiazolyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 2-bromo-5-thiazolyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 5-pyrimidinyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 2-methyl-5-pyrimidinyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl

TABLE 31-continued

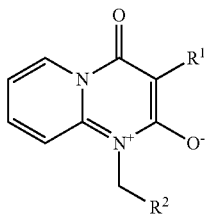

R¹

2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl

TABLE 32

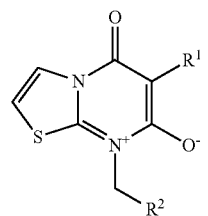

R¹

R² is 2-chloro-5-thiazolyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 6-chloro-3-pyridinyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is CF₃

4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl

TABLE 32-continued

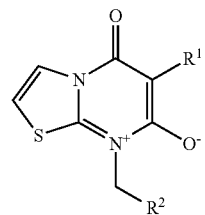

R¹

R² is 6-methyl-3-pyridinyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 6-fluoro-3-pyridinyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 3-pyridinyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 5-thiazolyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl
R² is 2-methyl-5-thiazolyl 4-(trifluoromethyl)-2-pyridinyl
6-(trifluoromethyl)-2-pyridinyl
4-(trifluoromethoxy)-2-pyridinyl
4-methyl-2-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl

TABLE 32-continued

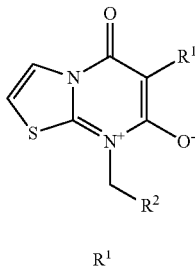

R¹

R² is 2-fluoro-5-thiazolyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl R² is 2-bromo-5-thiazolyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl R² is 5-pyrimidinyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl R² is 2-methyl-5-pyrimidinyl 4-(trifluoromethyl)-2-pyridinyl
6-(trifluoromethyl)-2-pyridinyl
4-(trifluoromethoxy)-2-pyridinyl
4-methyl-2-pyridinyl
2-fluoro-4-pyridinyl
2-chloro-4-pyridinyl
2-bromo-4-pyridinyl
2-cyano-4-pyridinyl
2-(trifluoromethyl)-4-pyridinyl
2-(trifluoromethoxy)-4-pyridinyl
2-methoxy-4-pyridinyl

TABLE 33

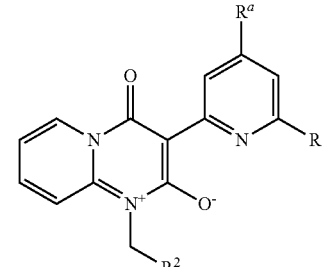

| $R^a$ | R |
|---|---|
| R² is 2-chloro-5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| R² is 6-chloro-3-pyridinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| R² is CF₃ | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |

TABLE 33-continued

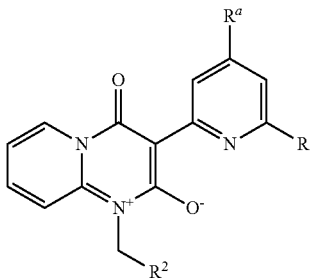

| $R^a$ | R |
|---|---|
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| $R^2$ is 6-methyl-3-pyridinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| $R^2$ is 6-fluoro-3-pyridinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |

TABLE 33-continued

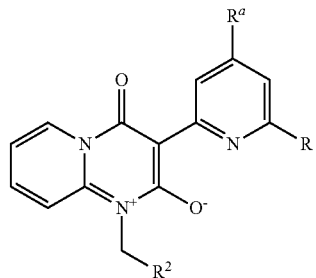

| $R^a$ | R |
|---|---|
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| $R^2$ is 3-pyridinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| $R^2$ is 5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

TABLE 33-continued

| $R^a$ | R |
|---|---|
| $R^2$ is 2-methyl-5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 2-fluoro-5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 2-bromo-5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 5-pyrimidinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 2-methyl-5-pyrimidinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |

TABLE 33-continued

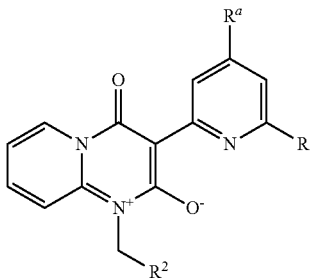

| $R^a$ | R |
|---|---|
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

TABLE 33a

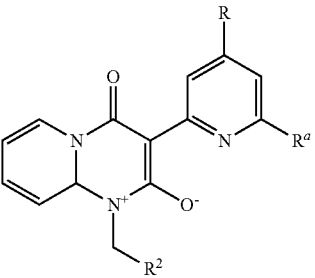

| $R^a$ | R |
|---|---|
| \multicolumn{2}{c}{$R^2$ is 2-chloro-5-thiazolyl} | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| \multicolumn{2}{c}{$R^2$ is 6-chloro-3-pyridinyl} | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |

TABLE 33a-continued

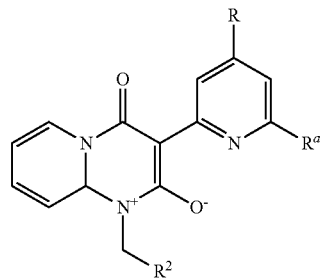

| $R^a$ | R |
|---|---|
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| \multicolumn{2}{c}{$R^2$ is CF₃} | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethyl)phenyl |
| \multicolumn{2}{c}{$R^2$ is 6-methyl-3-pyridinyl} | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |

TABLE 33a-continued

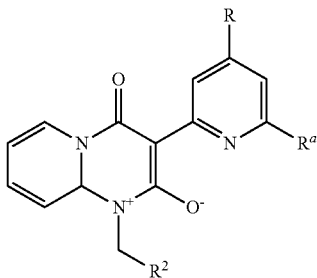

| $R^a$ | R |
|---|---|
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| \multicolumn{2}{c}{$R^2$ is 6-fluoro-3-pyridinyl} | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| \multicolumn{2}{c}{$R^2$ is 3-pyridinyl} | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

TABLE 33a-continued

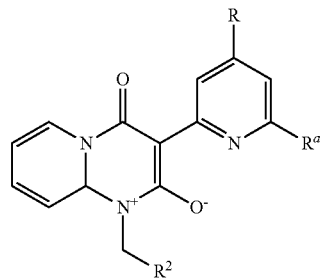

| $R^a$ | R |
|---|---|
| \multicolumn{2}{c}{$R^2$ is 5-thiazolyl} | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| \multicolumn{2}{c}{$R^2$ is 2-methyl-5-thiazolyl} | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| \multicolumn{2}{c}{$R^2$ is 2-fluoro-5-thiazolyl} | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |

TABLE 33a-continued

[Structure: pyrido-pyrimidinone with R, R^a on pyridine, R^2 on N-CH2]

| R^a | R |
|---|---|
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| R² is 2-bromo-5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| R² is 5-pyrimidinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |

TABLE 33a-continued

[Structure: pyrido-pyrimidinone with R, R^a on pyridine, R^2 on N-CH2]

| R^a | R |
|---|---|
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| R² is 2-methyl-5-pyrimidinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

TABLE 34

[Structure: thiazolo-pyrimidinone with R, R^a on pyridine, R^2 on N-CH2]

| R^a | R |
|---|---|
| R² is 2-chloro-5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |

TABLE 34-continued

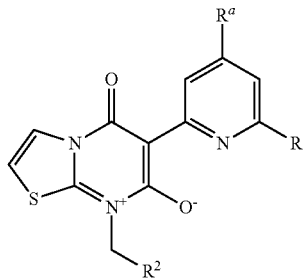

| $R^a$ | R |
|---|---|
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| $R^2$ is 6-chloro-3-pyridinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| $R^2$ is CF$_3$ | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |

TABLE 34-continued

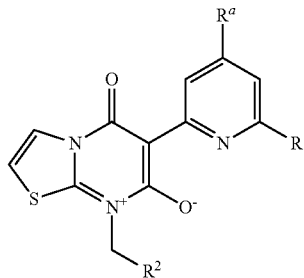

| $R^a$ | R |
|---|---|
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| $R^2$ is 6-methyl-3-pyridinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| $R^2$ is 6-fluoro-3-pyridinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

TABLE 34-continued

| $R^a$ | R |
|---|---|
| \multicolumn{2}{c}{$R^2$ is 3-pyridinyl} | 
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| \multicolumn{2}{c}{$R^2$ is 5-thiazolyl} |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| \multicolumn{2}{c}{$R^2$ is 2-methyl-5-thiazolyl} |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| \multicolumn{2}{c}{$R^2$ is 2-fluoro-5-thiazolyl} |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| \multicolumn{2}{c}{$R^2$ is 2-bromo-5-thiazolyl} |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |

TABLE 34-continued

| $R^a$ | R |
|---|---|
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| $R^2$ is 5-pyrimidinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| $R^2$ is 2-methyl-5-pyrimidinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

TABLE 34a

| $R^a$ | R |
|---|---|
| $R^2$ is 2-chloro-5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| $R^2$ is 6-chloro-3-pyridinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| $R^2$ is $CF_3$ | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |

TABLE 34a-continued

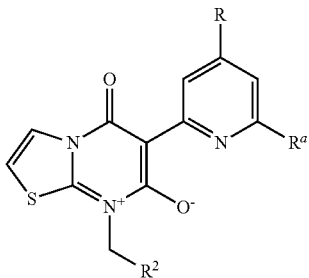

| $R^a$ | R |
|---|---|
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 6-methyl-3-pyridinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 6-fluoro-3-pyridinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |

TABLE 34a-continued

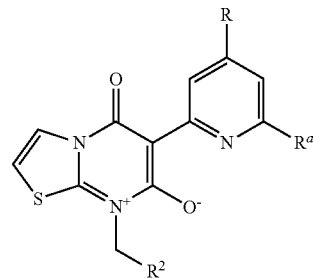

| $R^a$ | R |
|---|---|
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 3-pyridinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |

TABLE 34a-continued

[Structure: thiazolo-pyrimidinone fused ring with pendant pyridyl group bearing R and R^a substituents, N+ bearing CH2-R2, O-]

| R^a | R |
|---|---|
| R² is 2-methyl-5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| R² is 2-fluoro-5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| R² is 2-bromo-5-thiazolyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| R² is 5-pyrimidinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| R² is 2-methyl-5-pyrimidinyl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |

TABLE 34a-continued

Structure: thiazolo-pyrimidinone with R pyridine and R² substituent

| R$^a$ | R |
|---|---|
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

TABLE 35

| R |
|---|
| R$^2$ is 2-chloro-5-thiazolyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| R$^2$ is 6-chloro-3-pyridinyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| R$^2$ is CF$_3$ |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| R$^2$ is 6-methyl-3-pyridinyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |

TABLE 35-continued

| R |
|---|
| 2-fluoro-5-(trifluoromethoxy)phenyl |
| 4-chloro-2-methylphenyl |
| R$^2$ is 6-fluoro-3-pyridinyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| R$^2$ is 3-pyridinyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| R$^2$ is 5-thiazolyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| R$^2$ is 2-methyl-5-thiazolyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| R$^2$ is 2-fluoro-5-thiazolyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| R$^2$ is 2-bromo-5-thiazolyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| R$^2$ is 5-pyrimidinyl |
| 4-chloro-2-fluorophenyl |
| 2-fluoro-4-(trifluoromethyl)phenyl |

TABLE 35-continued

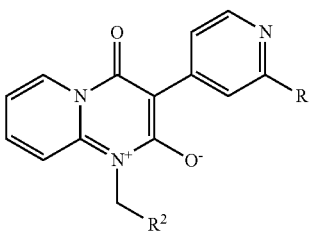

| R |
|---|
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| $R^2$ is 2-methyl-5-pyrimidinyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |

TABLE 36

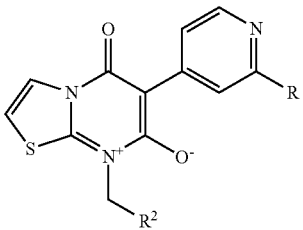

| R |
|---|
| $R^2$ is 2-chloro-5-thiazolyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| $R^2$ is 6-chloro-3-pyridinyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| $R^2$ is $CF_3$ |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |

TABLE 36-continued

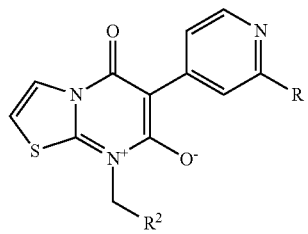

| R |
|---|
| $R^2$ is 6-methyl-3-pyridinyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| $R^2$ is 6-fluoro-3-pyridinyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| $R^2$ is 3-pyridinyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| $R^2$ is 5-thiazolyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| $R^2$ is 2-methyl-5-thiazolyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| $R^2$ is 2-fluoro-5-thiazolyl |
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| $R^2$ is 2-bromo-5-thiazolyl |
| 4-chloro-2-fluorophenyl |
| 2-fluoro-4-(trifluoromethyl)phenyl |
| 4-cyano-2-fluorophenyl |
| 2-chloro-4-cyanophenyl |

TABLE 36-continued

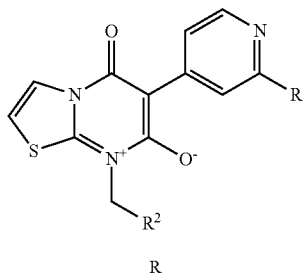

| R |
|---|
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| $R^2$ is 5-pyrimidinyl |

| |
|---|
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |
| $R^2$ is 2-methyl-5-pyrimidinyl |

| |
|---|
| 4-chloro-2-fluorophenyl |
| 2-fluoro-4-(trifluoromethyl)phenyl |
| 4-cyano-2-fluorophenyl |
| 2-chloro-4-cyanophenyl |
| 2-chloro-4-(trifluoromethyl)phenyl |
| 2-fluoro-5-(trifluoromethyl)phenyl |
| 2-fluoro-5-(trifluoromethoxy)phenyl |
| 4-chloro-2-methylphenyl |

A composition of this invention will generally be used as a formulation with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g, oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids can be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which are branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention can also contain formulation auxiliaries and additives, known to those skilled in the art as formulation aids (some of which can be considered to also function as solid diluents, liquid diluents or surfactants). Such formulation auxiliaries and additives can control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all formulations are prepared in conventional ways. "Active ingredients" refers to the aggregate of biologically active compounds or agents consisting of invertebrate pest control agents selected from the group (b) and fungicides in combination with the compound of Formula 1. For example, "active ingredients" can include a compound of Formula 1 and a further second invertebrate pest control agent selected from the group (b), or a compound of Formula 1, a further second invertebrate pest control agent selected from the group (b), and a fungicide. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

EXAMPLE A

| High Strength Concentrate | |
|---|---|
| active ingredients | 98.5% |
| silica aerogel | 0.5% |
| synthetic amorphous fine silica | 1.0% |

EXAMPLE B

| Wettable Powder | |
|---|---|
| active ingredients | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE C

| Granule | |
|---|---|
| active ingredients | 10.0% |
| attapulgite granules (low volatile matter, 0.71/0.30 mm; U.S.S. No. 25-50 sieves) | 90.0% |

EXAMPLE D

| Extruded Pellet | |
|---|---|
| active ingredients | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE E

| Emulsifiable Concentrate | |
|---|---|
| active ingredients | 10.0% |
| polyoxyethylene sorbitol hexoleate | 20.0% |
| $C_6$-$C_{10}$ fatty acid methyl ester | 70.0% |

EXAMPLE F

| Microemulsion | |
|---|---|
| active ingredients | 5.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE G

| Seed Treatment | |
|---|---|
| active ingredients | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

EXAMPLE H

| Fertilizer Stick | |
|---|---|
| active ingredients | 2.50% |
| pyrrolidone-styrene copolymer | 4.80% |
| tristyrylphenyl 16-ethoxylate | 2.30% |
| talc | 0.80% |
| corn starch | 5.00% |
| slow-release fertilizer | 36.00% |
| kaolin | 38.00% |
| water | 10.60% |

EXAMPLE I

| Suspension Concentrate | |
|---|---|
| active ingredients | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

EXAMPLE J

| Emulsion in Water | |
|---|---|
| active ingredients | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

EXAMPLE K

| Oil Dispersion | |
|---|---|
| active ingredients | 25% |
| polyoxyethylene sorbitol hexaoleate | 15% |
| organically modified bentonite clay | 2.5% |
| fatty acid methyl ester | 57.5% |

EXAMPLE L

| Suspoemulsion | |
|---|---|
| active ingredients | 10.0% |
| flusilazole | 5.0% |
| butyl polyoxyethylene/polypropylene block copolymer | 4.0% |
| stearic acid/polyethylene glycol copolymer | 1.0% |
| styrene acrylic polymer | 1.0% |

-continued

| Suspoemulsion | |
|---|---|
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Compositions of this invention exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

These present compositions are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compositions may interact synergistically with traits introduced by genetic engineering or modified by mutagenesis, thus enhancing phenotypic expression or effectiveness of the traits or increasing the invertebrate pest control effectiveness of the present compositions. In particular, the present compositions may interact synergistically with the phenotypic expression of proteins or other natural products toxic to invertebrate pests to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera frugiperda* J. E. Smith), beet armyworm (*Spodoptera exigua* Hübner), cotton leafworm (*Spodoptera littoralis* Boisduval), yellowstriped armyworm (*Spodoptera ornithogalli* Guenée), black cutworm (*Agrotis ipsilon* Hufnagel), velvetbean caterpillar (*Anticarsia gemmatalis* Hübner), green fruitworm (*Lithophane antennata* Walker), cabbage armyworm (*Barathra brassicae* Linnaeus), soybean looper (*Pseudoplusia includens* Walker), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: *Crambinae*) such as sod worm (*Herpetogramma licarsisalis* Walker), sugarcane stem borer (*Chilo infuscatellus* Snellen), tomato small borer (*Neoleucinodes elegantalis* Guenée), green leafroller (*Cnaphalocerus medinalis*), grape leaffolder (*Desmia funeralis* Hübner), melon worm (*Diaphania nitidalis* Stoll), cabbage center grub (*Helluala hydralis* Guenée), yellow stem borer (*Scirpophaga incertulas* Walker), early shoot borer (*Scirpophaga infuscatellus* Snellen), white stem borer (*Scirpophaga innotata* Walker), top shoot borer (*Scirpophaga nivella* Fabricius), dark-headed rice borer (*Chilo polychrysus* Meyrick), cabbage cluster caterpillar (*Crocidolomia binotalis* English)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), citrus false codling moth (*Cryptophlebia leucotreta* Meyrick), citrus borer (*Ecdytolopha aurantiana* Lima), redbanded leafroller (*Argyrotaenia velutinana* Walker), obliquebanded leafroller (*Choristoneura rosaceana* Harris), light brown apple moth (*Epiphyas postvittana* Walker), European grape berry moth (*Eupoecilia ambiguella* Hübner), apple bud moth (*Pandemis pyrusana* Kearfott), omnivorous leafroller (*Platynota stultana* Walsingham), barred fruit-tree tortrix (*Pandemis cerasana* Hübner), apple brown tortrix (*Pandemis heparana* Denis & Schiffermüller)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus), peach fruit borer (*Carposina niponensis* Walsingham), peach twig borer (*Anarsia lineatella* Zeller), potato tuberworm (*Phthorimaea operculella* Zeller), spotted tentiform leafminer (*Lithocolletis blancardella* Fabricius), Asiatic apple leafminer (*Lithocolletis ringoniella* Matsumura), rice leaffolder (Lerodea eufala Edwards), apple leafminer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Service), Australian Cockroach (*Periplaneta australasiae* Fabr.), lobster cockroach (*Nauphoeta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus* vestitus), Denver billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman), oriental beetle (*Anomala orientalis* Waterhouse, *Exomala orientalis* (Waterhouse) Baraud), northern masked chafer (*Cyclocephala borealis* Arrow), southern masked chafer (*Cyclocephala immaculata* Olivier or *C. lurida* Bland), dung beetle and white grub (*Aphodius* spp.), black turfgrass ataenius (Ataenius spretulus Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae.

In addition, agronomic and nonagronomic pests include: eggs, adults and larvae of the order Dermaptera including earwigs from the family Forficulidae (e.g., European earwig (*Forficula auricularia* Linnaeus), black earwig (*Chelisoches morio* Fabricius)); eggs, immatures, adults and nymphs of the orders Hemiptera and Homoptera such as, plant bugs from the family Miridae, cicadas from the family Cicadidae, leafhoppers (e.g. *Empoasca* spp.) from the family Cicadellidae, bed bugs (e.g., *Cimex lectularius* Linnaeus) from the family Cimicidae, planthoppers from the families Fulgoroidae and *Delphacidae*, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae.

Agronomic and nonagronomic pests also include: eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (Tetranychus mcdanieli McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae; ticks in the family Ixodidae, commonly known as hard ticks (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and ticks in the family Argasidae, commonly known as soft ticks (e.g., relapsing fever tick (*Ornithodoros turicata*), common fowl tick (*Argas radiatus*)); scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion thrips (*Thrips tabaci* Lindeman), flower thrips (*Frankliniella* spp.), and other foliar feeding thrips; insect pests of the order Hymenoptera including ants of the Family Formicidae including the Florida carpenter ant (*Camponotus floridanus* Buckley), red carpenter ant (*Camponotus ferrugineus* Fabricius), black carpenter ant (*Camponotus pennsylvanicus* De Geer), white-footed ant (*Technomyrmex albipes* fr. Smith), big headed ants (*Pheidole* sp.), ghost ant (*Tapinoma melanocephalum* Fabricius); Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster) and odorous house ant (*Tapinoma sessile* Say); bees (including carpenter bees), hornets, yellow jackets, wasps, and sawflies (*Neodiprion* spp.; *Cephus* spp.); insect pests of the order Isoptera including termites in the *Termitidae* (e.g., *Macrotermes* sp., *Odontotermes obesus* Rambur), Kalotermitidae (e.g., *Cryptotermes* sp.), and *Rhinotermitidae* (e.g., *Reticulitermes* sp., *Coptotermes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus* Linnaeus), chicken body louse (*Menacanthus stramineus* Nitzsch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds; spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus).

Examples of invertebrate pests of stored grain include larger grain borer (*Prostephanus truncatus*), lesser grain borer (*Rhyzopertha dominica*), rice weevil (*Stiophilus oryzae*), maize weevil (*Stiophilus zeamais*), cowpea weevil (*Callosobruchus maculatus*), red flour beetle (*Tribolium castaneum*), granary weevil (*Stiophilus granarius*), Indian meal moth (*Plodia interpunctella*), Mediterranean flour beetle (*Ephestia kuhniella*) and flat or rusty grain beetle (*Cryptolestis ferrugineus*).

Compositions of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenée (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Compositions of the invention also have significant activity on members from the order Homoptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compositions of this invention may also have activity on members from the order Hemiptera including: *Acrosternum hilare* Say (green stink bug), *Anasa tristis* De Geer (squash bug), *Blissus leucopterus leucopterus* Say (chinch bug), *Cimex lectularius* Linnaeus (bed bug) *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrips), *Scirthothrips citri* Moulton (citrus thrips), *Sericothrips variabilis* Beach (soybean thrips), and *Thrips tabaci* Lindeman (onion thrips); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compositions of this invention may also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Note that some contemporary classification systems place Homoptera as a suborder within the order Hemiptera.

Of note is use of compositions of this invention for controlling potato leafhopper (*Empoasca fabae*). Of note is use of compositions of this invention for controlling corn planthopper (*Peregrinus maidis*). Of note is use of compositions of this invention for controlling cotton melon aphid (*Aphis gossypii*). Of note is use of compositions of this invention for controlling green peach aphid (*Myzus persicae*). Of note is use of compositions of this invention for controlling diamondback moth (*Plutella xylostella*). Of note is use of compositions of this invention for controlling fall armyworm (*Spodoptera frugiperda*).

Of note is use of compositions of this invention for controlling southern green stink bug (*Nezara viridula*), western tarnished plant bug (*Lygus hesperus*), rice water weevil (*Lissorhoptrus oryzophilus*), rice brown planthopper (*Nilaparvata lugens*), rice green leafhopper (*Nephotettix virescens*) and striped rice borer (*Chilo suppressalis*).

Compositions of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1, an N-oxide or salt thereof, at least one additional component selected from the group consisting of surfactants, solid diluents and liquid diluents, and at least one additional biologically active compound or agent. For compositions of the present invention, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, amidoflumet, amitraz, avermectin, azadirachtin, azinphos-methyl, bensultap, bifenthrin, bifenazate, bistrifluoron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, meperfluthrin, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, sulfoxaflor, tebufenozide, tebufenpyrad, teflubenzuron, tefluthrin, terbufos, tetrachlorvinphos, tetramethrin, tetramethylfluthrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, amitraz, avermectin, azadirachtin, bensultap, bifenthrin, buprofezin, cadusafos, carbaryl, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of nucleo polyhedrosis viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than the compound of Formula 1. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but belonging to a different chemical class or having a different site of action. These additional biologically active compounds or agents include, but are not limited to, sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-gated chloride channel antagonists such as avermectin or blockers such as ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; molting inhibitors and ecdysone agonists such as azadirachtin, methoxyfenozide and tebufenozide; ryanodine receptor ligands such as ryanodine, anthranilic diamides such as chlorantraniliprole, cyantraniliprole and flubendiamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin or endosulfan; pyrethroids; carbamates; insecticidal ureas; and biological agents including nucleopolyhedro viruses (NPV), members of *Bacillus thuringiensis*, encapsulated delta-endotoxins of *Bacillus thuringiensis*, and other naturally occurring or genetically modified insecticidal viruses.

Further examples of biologically active compounds or agents with which compounds of this invention can be formulated are: fungicides such as 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, fluxapyroxad, folpet, fosetyl-aluminum, fthalide, fuberidazole, furalaxyl, furametpyr, hexaconazole, hymexazole, guazatine, imazalil, imibenconazole, iminoctadine, iodicarb, ipconazole, iprobenfos, iprodione, iprovalicarb, isoconazole, isoprothiolane, isotianil, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penflufen, penthiopyrad, perfurazoate, phosphonic acid, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pyrametostrobin, pyraoxystrobin, pryazophos, pyrifenox, pyrimethanil, pyrifenox, pyrifenone, pyrolnitrine, pyroquilon, quinconazole, quinoxyfen, quintozene, silthiofam, simeconazole, spiroxamine, streptomycin, sulfur, tebuconazole, tebufloquin, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimorphamide, tricyclazole, trifloxystrobin, triforine, triticonazole, uniconazole, validamycin, valifenalate, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

Of note are fungicides and compositions comprising fungicides such as 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, azoxystrobin, copper hydroxide, cymoxanil, cyproconazole, difenoconazole, famoxadone, fenoxanil, ferimzone, flusilazole, flutolanil, fthalide, furametpyr, hexaconazole, isoprothiolane, isotianil, kasugamycin, mancozeb, metominostrobin, orysastrobin, pencycuron, penthiopyrad, picoxystrobin, probenazole, propiconazole, proquinazid, pyroquilon, simeconazole, tiadinil, tricyclazole, trifloxystrobin and validamycin.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Compositions of this invention can be applied to plants genetically transformed to express proteins toxic to invertebrate pests (such as Bacillus thuringiensis delta-endotoxins). Such an application may provide a broader spectrum of plant protection and be advantageous for resistance management. The effect of the exogenously applied invertebrate pest control compositions of this invention may be synergistic with the expressed toxin proteins.

General references for these agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U.K., 2003 and *The BioPesticide Manual*, 2$^{nd}$ Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1, an N-oxide or salt thereof, is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of invertebrate pests controlled beyond the spectrum controlled by the compound of Formula 1 alone.

Table A lists specific combinations of a compound of Formula 1 with other invertebrate pest control agents illustrative of the mixtures, compositions and methods of the present invention. The first column of Table A lists the specific invertebrate pest control agents (e.g., "Abamectin" in the first line). The second column of Table A lists the mode of action (if known) or chemical class of the invertebrate pest control agents. The third column of Table A lists embodiment(s) of ranges of weight ratios for rates at which a compound of Formula 1 can be applied relative to an invertebrate pest control agent (e.g., "50:1 to 1:50" of a compound of Formula 1 relative to abamectin by weight). Thus, for example, the first line of Table A specifically discloses the combination of a compound of Formula 1 with abamectin can be applied in a weight ratio between 50:1 to 1:50. The remaining lines of Table A are to be construed similarly. Of further note Table A lists specific combinations of a compound of Formula 1 with other invertebrate pest control agents illustrative of the mixtures, compositions and methods of the present invention and includes additional embodiments of weight ratio ranges for application rates.

TABLE A

| Invertebrate Pest Control Agent | Mode of Action or Chemical Class | Typical Weight Ratio |
|---|---|---|
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyantraniliprole | ryanodine receptor ligands | 100:1 to 1:120 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |

TABLE A-continued

| Invertebrate Pest Control Agent | Mode of Action or Chemical Class | Typical Weight Ratio |
|---|---|---|
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

Of note is the composition of the present invention wherein the at least one additional biologically active compound or agent is selected from the Invertebrate Pest Control Agents listed in Table A above.

The weight ratios of a compound, including a compound of Formula 1, an N-oxide or salt thereof, to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Tables B1 to B77 are embodiments of specific compositions comprising a compound of Formula 1 (compound numbers (Cmpd. No.) refer to compounds in Index Tables A-C) and an additional invertebrate pest control agent.

TABLE B1

| Mixture No. | Cmpd. No. | and | Invertebrate Pest Control Agent |
|---|---|---|---|
| B1-1 | 6 | and | Abamectin |
| B1-2 | 6 | and | Acetamiprid |
| B1-3 | 6 | and | Amitraz |
| B1-4 | 6 | and | Avermectin |
| B1-5 | 6 | and | Azadirachtin |
| B1-5a | 6 | and | Bensultap |
| B1-6 | 6 | and | Beta-cyfluthrin |
| B1-7 | 6 | and | Bifenthrin |
| B1-8 | 6 | and | Buprofezin |
| B1-9 | 6 | and | Cartap |
| B1-10 | 6 | and | Chlorantraniliprole |
| B1-11 | 6 | and | Chlorfenapyr |
| B1-12 | 6 | and | Chlorpyrifos |
| B1-13 | 6 | and | Clothianidin |
| B1-14 | 6 | and | Cyantraniliprole |
| B1-15 | 6 | and | Cyfluthrin |
| B1-16 | 6 | and | Cyhalothrin |
| B1-17 | 6 | and | Cypermethrin |
| B1-18 | 6 | and | Cyromazine |
| B1-19 | 6 | and | Deltamethrin |
| B1-20 | 6 | and | Dieldrin |
| B1-21 | 6 | and | Dinotefuran |
| B1-22 | 6 | and | Diofenolan |
| B1-23 | 6 | and | Emamectin |
| B1-24 | 6 | and | Endosulfan |
| B1-25 | 6 | and | Esfenvalerate |
| B1-26 | 6 | and | Ethiprole |
| B1-27 | 6 | and | Fenothiocarb |
| B1-28 | 6 | and | Fenoxycarb |
| B1-29 | 6 | and | Fenvalerate |
| B1-30 | 6 | and | Fipronil |
| B1-31 | 6 | and | Flonicamid |
| B1-32 | 6 | and | Flubendiamide |
| B1-33 | 6 | and | Flufenoxuron |
| B1-34 | 6 | and | Hexaflumuron |
| B1-35 | 6 | and | Hydramethylnon |
| B1-36 | 6 | and | Imidacloprid |
| B1-37 | 6 | and | Indoxacarb |
| B1-38 | 6 | and | Lambda-cyhalothrin |
| B1-39 | 6 | and | Lufenuron |
| B1-40 | 6 | and | Metaflumizone |
| B1-41 | 6 | and | Methomyl |
| B1-42 | 6 | and | Methoprene |
| B1-43 | 6 | and | Methoxyfenozide |
| B1-44 | 6 | and | Nitenpyram |
| B1-45 | 6 | and | Nithiazine |
| B1-46 | 6 | and | Novaluron |
| B1-47 | 6 | and | Oxamyl |
| B1-48 | 6 | and | Phosmet |
| B1-49 | 6 | and | Pymetrozine |
| B1-50 | 6 | and | Pyrethrin |
| B1-51 | 6 | and | Pyridaben |
| B1-52 | 6 | and | Pyridalyl |
| B1-53 | 6 | and | Pyriproxyfen |
| B1-54 | 6 | and | Ryanodine |
| B1-55 | 6 | and | Spinetoram |
| B1-56 | 6 | and | Spinosad |
| B1-57 | 6 | and | Spirodiclofen |
| B1-58 | 6 | and | Spiromesifen |
| B1-59 | 6 | and | Spirotetramat |
| B1-60 | 6 | and | Tebufenozide |
| B1-61 | 6 | and | Thiacloprid |
| B1-62 | 6 | and | Thiamethoxam |
| B1-63 | 6 | and | Thiodicarb |
| B1-64 | 6 | and | Thiosultap-sodium |
| B1-65 | 6 | and | Tolfenpyrad |
| B1-66 | 6 | and | Tralomethrin |
| B1-67 | 6 | and | Triazamate |
| B1-68 | 6 | and | Triflumuron |
| B1-69 | 6 | and | *Bacillus thuringiensis* |
| B1-70 | 6 | and | *Bacillus thuringiensis* delta-endotoxin |
| B1-71 | 6 | and | NPV (e.g., Gemstar) |

Table B2

Table B2 is identical to Table B 1, except that each reference to compound 6 in the column headed "Cmpd. No." is replaced by a reference to compound 7. For example, the first mixture in Table B2 is designated B2-1 and is a mixture of compound 7 and the additional invertebrate pest control agent abamectin.

Table B3

Table B3 is identical to Table B 1, except that each reference to compound 6 in the column headed "Cmpd. No." is replaced by a reference to compound 8. For example, the first mixture in Table B3 is designated B3-1 and is a mixture of compound 8 and the additional invertebrate pest control agent abamectin.

Table B4

Table B4 is identical to Table B 1, except that each reference to compound 6 in the column headed "Cmpd. No." is replaced by a reference to compound 9. For example, the first mixture in Table B4 is designated B4-1 and is a mixture of compound 9 and the additional invertebrate pest control agent abamectin.

Table B5

Table B5 is identical to Table B 1, except that each reference to compound 6 in the column headed "Cmpd. No." is replaced by a reference to compound 10. For example, the first mixture in Table B5 is designated B5-1 and is a mixture of compound 10 and the additional invertebrate pest control agent abamectin.

Table B6

Table B6 is identical to Table B 1, except that each reference to compound 6 in the column headed "Cmpd. No." is replaced by a reference to compound 19. For example, the first mixture in Table B6 is designated B6-1 and is a mixture of compound 19 and the additional invertebrate pest control agent abamectin.

Table B7

Table B7 is identical to Table B 1, except that each reference to compound 6 in the column headed "Cmpd. No." is replaced by a reference to compound 20. For example, the first mixture in Table B7 is designated B7-1 and is a mixture of compound 20 and the additional invertebrate pest control agent abamectin.

Table B8

Table B8 is identical to Table B1, except that each reference to compound 6 in the column headed "Cmpd. No." is replaced by a reference to compound 29. For example, the first mixture in Table B8 is designated B8-1 and is a mixture of compound 29 and the additional invertebrate pest control agent abamectin.

Table B9

Table B9 is identical to Table B 1, except that each reference to compound 6 in the column headed "Cmpd. No." is replaced by a reference to compound 31. For example, the first mixture in Table B9 is designated B9-1 and is a mixture of compound 31 and the additional invertebrate pest control agent abamectin.

Table B10

Table B10 is identical to Table B1, except that each reference to compound 6 in the column headed "Cmpd. No." is replaced by a reference to compound 34. For example, the first mixture in Table B 10 is designated B 10-1 and is a mixture of compound 34 and the additional invertebrate pest control agent abamectin.

Table B11

Table B11 is identical to Table B1, except that each reference to compound 6 in the column headed "Cmpd. No." is replaced by a reference to compound 39. For example, the first mixture in Table B11 is designated B11-1 and is a mixture of compound 39 and the additional invertebrate pest control agent abamectin.

Table B12

Table B 12 is identical to Table B1, except that each reference to compound 6 in the column headed "Cmpd. No." is replaced by a reference to compound 48. For example, the first mixture in Table B12 is designated B12-1 and is a mixture of compound 48 and the additional invertebrate pest control agent abamectin.

Table B13

Table B 13 is identical to Table B1, except that each reference to compound 6 in the column headed "Cmpd. No." is replaced by a reference to compound 54. For example, the first mixture in Table B13 is designated B13-1 and is a mixture of compound 54 and the additional invertebrate pest control agent abamectin.

Table B14

Table B 14 is identical to Table B1, except that each reference to compound 6 in the column headed "Cmpd. No." is replaced by a reference to compound 55. For example, the first mixture in Table B14 is designated B14-1 and is a mixture of compound 55 and the additional invertebrate pest control agent abamectin.

Table B15

Table B 15 is identical to Table B1, except that each reference to compound 6 in the column headed "Cmpd. No." is replaced by a reference to compound 58. For example, the first mixture in Table B15 is designated B15-1 and is a mixture of compound 58 and the additional invertebrate pest control agent abamectin.

Table B16

Table B 16 is identical to Table B1, except that each reference to compound 6 in the column headed "Cmpd. No." is replaced by a reference to compound 105. For example, the first mixture in Table B16 is designated B16-1 and is a mixture of compound 105 and the additional invertebrate pest control agent abamectin.

Table B17

Table B 17 is identical to Table B1, except that each reference to compound 6 in the column headed "Cmpd. No." is replaced by a reference to compound 106. For example, the first mixture in Table B17 is designated B17-1 and is a mixture of compound 106 and the additional invertebrate pest control agent abamectin.

Table B18

Table B 18 is identical to Table B1, except that each reference to compound 6 in the column headed "Cmpd. No." is replaced by a reference to compound 107. For example, the first mixture in Table B18 is designated B18-1 and is a mixture of compound 107 and the additional invertebrate pest control agent abamectin.

Table B19

Table B19 is identical to Table B1, except that each reference to compound 6 in the column headed "Cmpd. No." is replaced by a reference to compound 108. For example, the first mixture in Table B19 is designated B19-1 and is a mixture of compound 108 and the additional invertebrate pest control agent abamectin.

Table B20

Table B20 is identical to Table B1, except that each reference to compound 6 in the column headed "Cmpd. No." is replaced by a reference to compound 109. For example, the first mixture in Table B20 is designated B20-1 and is a mixture of compound 109 and the additional invertebrate pest control agent abamectin.

Table B21

Table B21 is identical to Table B1, except that each reference to compound 6 in the column headed "Cmpd. No." is replaced by a reference to compound 110. For example, the first mixture in Table B21 is designated B21-1 and is a mixture of compound 110 and the additional invertebrate pest control agent abamectin.

Table B22

Table B22 is identical to Table B1, except that each reference to compound 6 in the column headed "Cmpd. No." is replaced by a reference to compound 111. For example, the first mixture in Table B22 is designated B22-1 and is a mixture of compound 111 and the additional invertebrate pest control agent abamectin.

Table B23

Table B23 is identical to Table B1, except that each reference to compound 6 in the column headed "Cmpd. No." is replaced by a reference to compound 112. For example, the first mixture in Table B23 is designated B23-1 and is a mixture of compound 112 and the additional invertebrate pest control agent abamectin.

Table B24

Table B24 is identical to Table B1, except that each reference to compound 6 in the column headed "Cmpd. No." is replaced by a reference to compound 113. For example, the first mixture in Table B24 is designated B24-1 and is a mixture of compound 113 and the additional invertebrate pest control agent abamectin.

Table B25

Table B25 is identical to Table B1, except that each reference to compound 6 in the column headed "Cmpd. No." is replaced by a reference to compound 114. For example, the first mixture in Table B25 is designated B25-1 and is a mixture of compound 114 and the additional invertebrate pest control agent abamectin.

Table B26

Table B26 is identical to Table B1, except that each reference to compound 6 in the column headed "Cmpd. No." is replaced by a reference to compound 115. For example, the first mixture in Table B26 is designated B26-1 and is a mixture of compound 115 and the additional invertebrate pest control agent abamectin.

Table B27

Table B27 is identical to Table B1, except that each reference to compound 6 in the column headed "Cmpd. No." is replaced by a reference to compound 116. For example, the first mixture in Table B27 is designated B27-1 and is a mixture of compound 116 and the additional invertebrate pest control agent abamectin.

Table B28

Table B28 is identical to Table B1, except that each reference to compound 6 in the column headed "Cmpd. No." is replaced by a reference to compound 117. For example, the first mixture in Table B28 is designated B28-1 and is a mixture of compound 117 and the additional invertebrate pest control agent abamectin.

Table B29

Table B29 is identical to Table B1, except that each reference to compound 6 in the column headed "Cmpd. No." is replaced by a reference to compound 118. For example, the first mixture in Table B29 is designated B29-1 and is a mixture of compound 118 and the additional invertebrate pest control agent abamectin.

Table B30

Table B30 is identical to Table B1, except that each reference to compound 6 in the column headed "Cmpd. No." is replaced by a reference to compound 119. For example, the first mixture in Table B30 is designated B30-1 and is a mixture of compound 119 and the additional invertebrate pest control agent abamectin.

Table B31

Table B31 is identical to Table B1, except that each reference to compound 6 in the column headed "Cmpd. No." is replaced by a reference to compound 120. For example, the first mixture in Table B31 is designated B31-1 and is a mixture of compound 120 and the additional invertebrate pest control agent abamectin.

Table B32

Table B32 is identical to Table B1, except that each reference to compound 6 in the column headed "Cmpd. No." is replaced by a reference to compound 121. For example, the first mixture in Table B32 is designated B32-1 and is a mixture of compound 121 and the additional invertebrate pest control agent abamectin.

Table B33

Table B33 is identical to Table B1, except that each reference to compound 6 in the column headed "Cmpd. No." is replaced by a reference to compound 122. For example, the first mixture in Table B33 is designated B33-1 and is a mixture of compound 122 and the additional invertebrate pest control agent abamectin.

Table B34

Table B34 is identical to Table B1, except that each reference to compound 6 in the column headed "Cmpd. No." is replaced by a reference to compound 123. For example, the first mixture in Table B34 is designated B34-1 and is a mixture of compound 123 and the additional invertebrate pest control agent abamectin.

Table B35

Table B35 is identical to Table B1, except that each reference to compound 6 in the column headed "Cmpd. No." is replaced by a reference to compound 124. For example, the first mixture in Table B35 is designated B35-1 and is a mixture of compound 124 and the additional invertebrate pest control agent abamectin.

Table B36

Table B36 is identical to Table B1, except that each reference to compound 6 in the column headed "Cmpd. No." is replaced by a reference to compound 125. For example, the first mixture in Table B36 is designated B36-1 and is a mixture of compound 125 and the additional invertebrate pest control agent abamectin.

Table B37

Table B37 is identical to Table B1, except that each reference to compound 6 in the column headed "Cmpd. No." is replaced by a reference to compound 126. For example, the first mixture in Table B37 is designated B37-1 and is a mixture of compound 126 and the additional invertebrate pest control agent abamectin.

Table B38

Table B38 is identical to Table B1, except that each reference to compound 6 in the column headed "Cmpd. No." is replaced by a reference to compound 127. For example, the first mixture in Table B38 is designated B38-1 and is a mixture of compound 127 and the additional invertebrate pest control agent abamectin.

Table B39

Table B39 is identical to Table B1, except that each reference to compound 6 in the column headed "Cmpd. No." is replaced by a reference to compound 128. For example, the first mixture in Table B39 is designated B39-1 and is a mixture of compound 128 and the additional invertebrate pest control agent abamectin.

Table B40

Table B40 is identical to Table B1, except that each reference to compound 6 in the column headed "Cmpd. No." is replaced by a reference to compound 129. For example, the first mixture in Table B40 is designated B40-1 and is a mixture of compound 129 and the additional invertebrate pest control agent abamectin.

Table B41

Table B41 is identical to Table B1, except that each reference to compound 6 in the column headed "Cmpd. No." is replaced by a reference to compound 130. For example, the first mixture in Table B41 is designated B41-1 and is a mixture of compound 130 and the additional invertebrate pest control agent abamectin.

Table B42

Table B42 is identical to Table B1, except that each reference to compound 6 in the column headed "Cmpd. No." is replaced by a reference to compound 131. For example, the first mixture in Table B42 is designated B42-1 and is a mixture of compound 131 and the additional invertebrate pest control agent abamectin.

Table B43

Table B43 is identical to Table B1, except that each reference to compound 6 in the column headed "Cmpd. No." is replaced by a reference to compound 132. For example, the first mixture in Table B43 is designated B43-1 and is a mixture of compound 132 and the additional invertebrate pest control agent abamectin.

Table B44

Table B44 is identical to Table B1, except that each reference to compound 6 in the column headed "Cmpd. No." is replaced by a reference to compound 133. For example, the first mixture in Table B44 is designated B44-1 and is a mixture of compound 133 and the additional invertebrate pest control agent abamectin.

Table B45

Table B45 is identical to Table B1, except that each reference to compound 6 in the column headed "Cmpd. No." is replaced by a reference to compound 134. For example, the first mixture in Table B45 is designated B45-1 and is a mixture of compound 134 and the additional invertebrate pest control agent abamectin.

Table B46

Table B46 is identical to Table B1, except that each reference to compound 6 in the column headed "Cmpd. No." is replaced by a reference to compound 135. For example, the first mixture in Table B46 is designated B46-1 and is a mixture of compound 135 and the additional invertebrate pest control agent abamectin.

Table B47

Table B47 is identical to Table B1, except that each reference to compound 6 in the column headed "Cmpd. No." is replaced by a reference to compound 136. For example, the first mixture in Table B47 is designated B47-1 and is a mixture of compound 136 and the additional invertebrate pest control agent abamectin.

Table B48

Table B48 is identical to Table B1, except that each reference to compound 6 in the column headed "Cmpd. No." is replaced by a reference to compound 137. For example, the first mixture in Table B48 is designated B48-1 and is a mixture of compound 137 and the additional invertebrate pest control agent abamectin.

Table B49

Table B49 is identical to Table B1, except that each reference to compound 6 in the column headed "Cmpd. No." is replaced by a reference to compound 138. For example, the first mixture in Table B49 is designated B49-1 and is a mixture of compound 138 and the additional invertebrate pest control agent abamectin.

Table B50

Table B50 is identical to Table B1, except that each reference to compound 6 in the column headed "Cmpd. No." is replaced by a reference to compound 139. For example, the first mixture in Table B50 is designated B50-1 and is a mixture of compound 139 and the additional invertebrate pest control agent abamectin.

Table B51

Table B51 is identical to Table B1, except that each reference to compound 6 in the column headed "Cmpd. No." is replaced by a reference to compound 140. For example, the first mixture in Table B51 is designated B51-1 and is a mixture of compound 140 and the additional invertebrate pest control agent abamectin.

Table B51a

Table B51a is identical to Table B1, except that each reference to compound 6 in the column headed "Cmpd. No." is replaced by a reference to compound 541. For example, the first mixture in Table B51a is designated B51a-1 and is a mixture of compound 541 and the additional invertebrate pest control agent abamectin.

Table B52

Table B52 is identical to Table B1, except that each reference to compound 6 in the column headed "Cmpd. No." is replaced by a reference to compound 542. For example, the first mixture in Table B52 is designated B52-1 and is a mixture of compound 542 and the additional invertebrate pest control agent abamectin.

Table B53

Table B53 is identical to Table B1, except that each reference to compound 6 in the column headed "Cmpd. No." is replaced by a reference to compound 576. For example, the first mixture in Table B53 is designated B53-1 and is a mixture of compound 576 and the additional invertebrate pest control agent abamectin.

Table B54

Table B54 is identical to Table B1, except that each reference to compound 6 in the column headed "Cmpd. No." is replaced by a reference to compound 583. For example, the first mixture in Table B54 is designated B54-1 and is a mixture of compound 583 and the additional invertebrate pest control agent abamectin.

Table B55

Table B55 is identical to Table B1, except that each reference to compound 6 in the column headed "Cmpd. No." is replaced by a reference to compound 594. For example, the first mixture in Table B55 is designated B55-1 and is a mixture of compound 594 and the additional invertebrate pest control agent abamectin.

Table B56

Table B56 is identical to Table B1, except that each reference to compound 6 in the column headed "Cmpd. No." is replaced by a reference to compound 654. For example, the first mixture in Table B56 is designated B56-1 and is a mixture of compound 654 and the additional invertebrate pest control agent abamectin.

Table B57

Table B57 is identical to Table B1, except that each reference to compound 6 in the column headed "Cmpd. No." is replaced by a reference to compound 657. For example, the first mixture in Table B57 is designated B57-1 and is a mixture of compound 657 and the additional invertebrate pest control agent abamectin.

Table B58

Table B58 is identical to Table B1, except that each reference to compound 6 in the column headed "Cmpd. No." is replaced by a reference to compound 669. For example, the first mixture in Table B58 is designated B58-1 and is a mixture of compound 669 and the additional invertebrate pest control agent abamectin.

Table B59

Table B59 is identical to Table B1, except that each reference to compound 6 in the column headed "Cmpd. No." is replaced by a reference to compound 670. For example, the first mixture in Table B59 is designated B59-1 and is a mixture of compound 670 and the additional invertebrate pest control agent abamectin.

Table B60

Table B60 is identical to Table B1, except that each reference to compound 6 in the column headed "Cmpd. No." is replaced by a reference to compound 682. For example, the first mixture in Table B60 is designated B60-1 and is a mixture of compound 682 and the additional invertebrate pest control agent abamectin.

Table B61

Table B61 is identical to Table B1, except that each reference to compound 6 in the column headed "Cmpd. No." is replaced by a reference to compound 683. For example, the first mixture in Table B61 is designated B61-1 and is a mixture of compound 683 and the additional invertebrate pest control agent abamectin.

Table B62

Table B62 is identical to Table B1, except that each reference to compound 6 in the column headed "Cmpd. No." is replaced by a reference to compound 687. For example, the first mixture in Table B62 is designated B62-1 and is a mixture of compound 687 and the additional invertebrate pest control agent abamectin.

Table B63

Table B63 is identical to Table B1, except that each reference to compound 6 in the column headed "Cmpd. No." is replaced by a reference to compound 718. For example, the first mixture in Table B63 is designated B63-1 and is a mixture of compound 718 and the additional invertebrate pest control agent abamectin.

Table B64

Table B64 is identical to Table B1, except that each reference to compound 6 in the column headed "Cmpd. No." is replaced by a reference to compound 725. For example, the first mixture in Table B64 is designated B64-1 and is a mixture of compound 725 and the additional invertebrate pest control agent abamectin.

Table B65

Table B65 is identical to Table B1, except that each reference to compound 6 in the column headed "Cmpd. No." is replaced by a reference to compound 726. For example, the first mixture in Table B65 is designated B65-1 and is a mixture of compound 726 and the additional invertebrate pest control agent abamectin.

Table B66

Table B66 is identical to Table B1, except that each reference to compound 6 in the column headed "Cmpd. No." is replaced by a reference to compound 727. For example, the first mixture in Table B66 is designated B66-1 and is a mixture of compound 727 and the additional invertebrate pest control agent abamectin.

Table B67

Table B67 is identical to Table B1, except that each reference to compound 6 in the column headed "Cmpd. No." is replaced by a reference to compound 734. For example, the first mixture in Table B67 is designated B67-1 and is a mixture of compound 734 and the additional invertebrate pest control agent abamectin.

Table B68

Table B68 is identical to Table B1, except that each reference to compound 6 in the column headed "Cmpd. No." is replaced by a reference to compound 735. For example, the first mixture in Table B68 is designated B68-1 and is a mixture of compound 735 and the additional invertebrate pest control agent abamectin.

Table B69

Table B69 is identical to Table B1, except that each reference to compound 6 in the column headed "Cmpd. No." is replaced by a reference to compound 737. For example, the first mixture in Table B69 is designated B69-1 and is a mixture of compound 737 and the additional invertebrate pest control agent abamectin.

Table B70

Table B70 is identical to Table B1, except that each reference to compound 6 in the column headed "Cmpd. No." is replaced by a reference to compound 744. For example, the first mixture in Table B70 is designated B70-1 and is a mixture of compound 744 and the additional invertebrate pest control agent abamectin.

Table B71

Table B71 is identical to Table B1, except that each reference to compound 6 in the column headed "Cmpd. No." is replaced by a reference to compound 745. For example, the first mixture in Table B71 is designated B71-1 and is a mixture of compound 745 and the additional invertebrate pest control agent abamectin.

Table B72

Table B72 is identical to Table B1, except that each reference to compound 6 in the column headed "Cmpd. No." is replaced by a reference to compound 746. For example, the first mixture in Table B72 is designated B72-1 and is a mixture of compound 746 and the additional invertebrate pest control agent abamectin.

Table B73

Table B73 is identical to Table B1, except that each reference to compound 6 in the column headed "Cmpd. No." is replaced by a reference to compound 748. For example, the first mixture in Table B73 is designated B73-1 and is a mixture of compound 748 and the additional invertebrate pest control agent abamectin.

Table B74

Table B74 is identical to Table B1, except that each reference to compound 6 in the column headed "Cmpd. No." is replaced by a reference to compound 749. For example, the first mixture in Table B74 is designated B74-1 and is a mixture of compound 749 and the additional invertebrate pest control agent abamectin.

Table B75

Table B75 is identical to Table B1, except that each reference to compound 6 in the column headed "Cmpd. No." is replaced by a reference to compound 750. For example, the first mixture in Table B75 is designated B75-1 and is a mixture of compound 750 and the additional invertebrate pest control agent abamectin.

Table B76

Table B76 is identical to Table B1, except that each reference to compound 6 in the column headed "Cmpd. No." is replaced by a reference to compound 926. For example, the first mixture in Table B76 is designated B76-1 and is a mixture of compound 926 and the additional invertebrate pest control agent abamectin.

Table B77

Table B77 is identical to Table B1, except that each reference to compound 6 in the column headed "Cmpd. No." is replaced by a reference to compound 930. For example, the first mixture in Table B77 is designated B77-1 and is a mixture of compound 930 and the additional invertebrate pest control agent abamectin.

The specific mixtures listed in Tables B1 to B77 typically combine a compound of Formula 1 with the other invertebrate pest agent in the ratios specified in Table A.

Listed below in Tables C1 to C77 are embodiments of specific compositions comprising a compound of Formula 1 (compound numbers (Cmpd. No.) refer to compounds in Index Tables A-C) and an additional fungicide.

TABLE C1

| Mixture No. | Cmpd. No. | and | Fungicide |
|---|---|---|---|
| C1-1 | 6 | and | Probenazole |
| C1-2 | 6 | and | Tiadinil |
| C1-3 | 6 | and | Isotianil |
| C1-4 | 6 | and | Pyroquilon |
| C1-5 | 6 | and | Metominostrobin |
| C1-6 | 6 | and | Flutolanil |
| C1-7 | 6 | and | Validamycin |
| C1-8 | 6 | and | Furametpyr |
| C1-9 | 6 | and | Pencycuron |
| C1-10 | 6 | and | Simeconazole |
| C1-11 | 6 | and | Orysastrobin |
| C1-12 | 6 | and | Trifloxystrobin |
| C1-13 | 6 | and | Isoprothiolane |
| C1-14 | 6 | and | Azoxystrobin |
| C1-15 | 6 | and | Tricyclazole |
| C1-16 | 6 | and | Hexaconazole |
| C1-17 | 6 | and | Difenoconazole |
| C1-18 | 6 | and | Cyproconazole |
| C1-19 | 6 | and | Propiconazole |
| C1-20 | 6 | and | Fenoxanil |
| C1-21 | 6 | and | Ferimzone |
| C1-22 | 6 | and | Fthalide |
| C1-23 | 6 | and | Kasugamycin |
| C1-24 | 6 | and | Picoxystrobin |
| C1-25 | 6 | and | Penthiopyrad |
| C1-26 | 6 | and | Famoxadone |
| C1-27 | 6 | and | Cymoxanil |
| C1-28 | 6 | and | Proquinazid |
| C1-29 | 6 | and | Flusilazole |
| C1-30 | 6 | and | Mancozeb |
| C1-31 | 6 | and | Copper hydroxide |
| C1-32 | 6 | and | (a) |

(a) 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone

Table C2

Table C2 is identical to Table C1, except that each reference to compound 6 in the column headed "Cmpd. No." is replaced by a reference to compound 7. For example, the first mixture in Table C2 is designated C2-1 and is a mixture of compound 7 and the additional fungicide probenazole.

Table C3

Table C3 is identical to Table C1, except that each reference to compound 6 in the column headed "Cmpd. No." is replaced by a reference to compound 8. For example, the first mixture in Table C3 is designated C3-1 and is a mixture of compound 8 and the additional fungicide probenazole.

Table C4

Table C4 is identical to Table C1, except that each reference to compound 6 in the column headed "Cmpd. No." is replaced by a reference to compound 9. For example, the first mixture in Table C4 is designated C4-1 and is a mixture of compound 9 and the additional fungicide probenazole.

Table C5

Table C5 is identical to Table C1, except that each reference to compound 6 in the column headed "Cmpd. No." is replaced by a reference to compound 10. For example, the first mixture in Table C5 is designated C5-1 and is a mixture of compound 10 and the additional fungicide probenazole.

Table C6

Table C6 is identical to Table C1, except that each reference to compound 6 in the column headed "Cmpd. No." is replaced by a reference to compound 19. For example, the first mixture in Table C6 is designated C6-1 and is a mixture of compound 19 and the additional fungicide probenazole.

Table C7

Table C7 is identical to Table C1, except that each reference to compound 6 in the column headed "Cmpd. No." is replaced by a reference to compound 20. For example, the first mixture in Table C7 is designated C7-1 and is a mixture of compound 20 and the additional fungicide probenazole.

Table C8

Table C8 is identical to Table C1, except that each reference to compound 6 in the column headed "Cmpd. No." is replaced by a reference to compound 29. For example, the first mixture in Table C8 is designated C8-1 and is a mixture of compound 29 and the additional fungicide probenazole.

Table C9

Table C9 is identical to Table C1, except that each reference to compound 6 in the column headed "Cmpd. No." is replaced by a reference to compound 31. For example, the first mixture in Table C9 is designated C9-1 and is a mixture of compound 31 and the additional fungicide probenazole.

Table C10

Table C 10 is identical to Table C 1, except that each reference to compound 6 in the column headed "Cmpd. No." is replaced by a reference to compound 34. For example, the first mixture in Table C10 is designated C10-1 and is a mixture of compound 34 and the additional fungicide probenazole.

Table C11

Table C11 is identical to Table C 1, except that each reference to compound 6 in the column headed "Cmpd. No." is replaced by a reference to compound 39. For example, the first mixture in Table C11 is designated C11-1 and is a mixture of compound 39 and the additional fungicide probenazole.

Table C12

Table C12 is identical to Table C 1, except that each reference to compound 6 in the column headed "Cmpd. No." is replaced by a reference to compound 48. For example, the first mixture in Table C12 is designated C12-1 and is a mixture of compound 48 and the additional fungicide probenazole.

Table C13

Table C13 is identical to Table C 1, except that each reference to compound 6 in the column headed "Cmpd. No." is replaced by a reference to compound 54. For example, the first mixture in Table C13 is designated C13-1 and is a mixture of compound 54 and the additional fungicide probenazole.

Table C14

Table C 14 is identical to Table C 1, except that each reference to compound 6 in the column headed "Cmpd. No." is replaced by a reference to compound 55. For example, the first mixture in Table C14 is designated C14-1 and is a mixture of compound 55 and the additional fungicide probenazole.

Table C15

Table C 15 is identical to Table C 1, except that each reference to compound 6 in the column headed "Cmpd. No." is replaced by a reference to compound 58. For example, the first mixture in Table C15 is designated C15-1 and is a mixture of compound 58 and the additional fungicide probenazole.

Table C16

Table C 16 is identical to Table C 1, except that each reference to compound 6 in the column headed "Cmpd. No." is replaced by a reference to compound 105. For example, the first mixture in Table C16 is designated C16-1 and is a mixture of compound 105 and the additional fungicide probenazole.

Table C17

Table C 17 is identical to Table C 1, except that each reference to compound 6 in the column headed "Cmpd. No." is replaced by a reference to compound 106. For example, the first mixture in Table C17 is designated C17-1 and is a mixture of compound 106 and the additional fungicide probenazole.

Table C18

Table C18 is identical to Table C 1, except that each reference to compound 6 in the column headed "Cmpd. No." is replaced by a reference to compound 107. For example, the first mixture in Table C18 is designated C18-1 and is a mixture of compound 107 and the additional fungicide probenazole.

Table C19

Table C19 is identical to Table C 1, except that each reference to compound 6 in the column headed "Cmpd. No." is replaced by a reference to compound 108. For example, the first mixture in Table C19 is designated C19-1 and is a mixture of compound 108 and the additional fungicide probenazole.

Table C20

Table C20 is identical to Table C1, except that each reference to compound 6 in the column headed "Cmpd. No." is replaced by a reference to compound 109. For example, the first mixture in Table C20 is designated C20-1 and is a mixture of compound 109 and the additional fungicide probenazole.

Table C21

Table C21 is identical to Table C1, except that each reference to compound 6 in the column headed "Cmpd. No." is replaced by a reference to compound 110. For example, the first mixture in Table C21 is designated C21-1 and is a mixture of compound 110 and the additional fungicide probenazole.

Table C22

Table C22 is identical to Table C1, except that each reference to compound 6 in the column headed "Cmpd. No." is replaced by a reference to compound 111. For example, the first mixture in Table C22 is designated C22-1 and is a mixture of compound 111 and the additional fungicide probenazole.

Table C23

Table C23 is identical to Table C1, except that each reference to compound 6 in the column headed "Cmpd. No." is replaced by a reference to compound 112. For example, the first mixture in Table C23 is designated C23-1 and is a mixture of compound 112 and the additional fungicide probenazole.

Table C24

Table C24 is identical to Table C1, except that each reference to compound 6 in the column headed "Cmpd. No." is replaced by a reference to compound 113. For example, the first mixture in Table C24 is designated C24-1 and is a mixture of compound 113 and the additional fungicide probenazole.

Table C25

Table C25 is identical to Table C1, except that each reference to compound 6 in the column headed "Cmpd. No." is replaced by a reference to compound 114. For example, the first mixture in Table C25 is designated C25-1 and is a mixture of compound 114 and the additional fungicide probenazole.

Table C26

Table C26 is identical to Table C1, except that each reference to compound 6 in the column headed "Cmpd. No." is replaced by a reference to compound 115. For example, the first mixture in Table C26 is designated C26-1 and is a mixture of compound 115 and the additional fungicide probenazole.

Table C27

Table C27 is identical to Table C1, except that each reference to compound 6 in the column headed "Cmpd. No." is replaced by a reference to compound 116. For example, the first mixture in Table C27 is designated C27-1 and is a mixture of compound 116 and the additional fungicide probenazole.

Table C28

Table C28 is identical to Table C1, except that each reference to compound 6 in the column headed "Cmpd. No." is replaced by a reference to compound 117. For example, the first mixture in Table C28 is designated C28-1 and is a mixture of compound 117 and the additional fungicide probenazole.

Table C29

Table C29 is identical to Table C1, except that each reference to compound 6 in the column headed "Cmpd. No." is replaced by a reference to compound 118. For example, the first mixture in Table C29 is designated C29-1 and is a mixture of compound 118 and the additional fungicide probenazole.

Table C30

Table C30 is identical to Table C1, except that each reference to compound 6 in the column headed "Cmpd. No." is replaced by a reference to compound 119. For example, the first mixture in Table C30 is designated C30-1 and is a mixture of compound 119 and the additional fungicide probenazole.

Table C31

Table C31 is identical to Table C1, except that each reference to compound 6 in the column headed "Cmpd. No." is replaced by a reference to compound 120. For example, the first mixture in Table C31 is designated C31-1 and is a mixture of compound 120 and the additional fungicide probenazole.

Table C32

Table C32 is identical to Table C1, except that each reference to compound 6 in the column headed "Cmpd. No." is replaced by a reference to compound 121. For example, the first mixture in Table C32 is designated C32-1 and is a mixture of compound 121 and the additional fungicide probenazole.

Table C33

Table C33 is identical to Table C1, except that each reference to compound 6 in the column headed "Cmpd. No." is replaced by a reference to compound 122. For example, the first mixture in Table C33 is designated C33-1 and is a mixture of compound 122 and the additional fungicide probenazole.

Table C34

Table C34 is identical to Table C1, except that each reference to compound 6 in the column headed "Cmpd. No." is replaced by a reference to compound 123. For example, the first mixture in Table C34 is designated C34-1 and is a mixture of compound 123 and the additional fungicide probenazole.

Table C35

Table C35 is identical to Table C1, except that each reference to compound 6 in the column headed "Cmpd. No." is replaced by a reference to compound 124. For example, the first mixture in Table C35 is designated C35-1 and is a mixture of compound 124 and the additional fungicide probenazole.

Table C36

Table C36 is identical to Table C1, except that each reference to compound 6 in the column headed "Cmpd. No." is replaced by a reference to compound 125. For example, the first mixture in Table C36 is designated C36-1 and is a mixture of compound 125 and the additional fungicide probenazole.

Table C37

Table C37 is identical to Table C1, except that each reference to compound 6 in the column headed "Cmpd. No." is replaced by a reference to compound 126. For example, the first mixture in Table C37 is designated C37-1 and is a mixture of compound 126 and the additional fungicide probenazole.

Table C38

Table C38 is identical to Table C1, except that each reference to compound 6 in the column headed "Cmpd. No." is replaced by a reference to compound 127. For example, the first mixture in Table C38 is designated C38-1 and is a mixture of compound 127 and the additional fungicide probenazole.

Table C39

Table C39 is identical to Table C1, except that each reference to compound 6 in the column headed "Cmpd. No." is replaced by a reference to compound 128. For example, the first mixture in Table C39 is designated C39-1 and is a mixture of compound 128 and the additional fungicide probenazole.

Table C40

Table C40 is identical to Table C1, except that each reference to compound 6 in the column headed "Cmpd. No." is replaced by a reference to compound 129. For example, the first mixture in Table C40 is designated C40-1 and is a mixture of compound 129 and the additional fungicide probenazole.

Table C41

Table C41 is identical to Table C1, except that each reference to compound 6 in the column headed "Cmpd. No." is replaced by a reference to compound 130. For example, the first mixture in Table C41 is designated C41-1 and is a mixture of compound 130 and the additional fungicide probenazole.

Table C42

Table C42 is identical to Table C1, except that each reference to compound 6 in the column headed "Cmpd. No." is replaced by a reference to compound 131. For example, the first mixture in Table C42 is designated C42-1 and is a mixture of compound 131 and the additional fungicide probenazole.

Table C43

Table C43 is identical to Table C1, except that each reference to compound 6 in the column headed "Cmpd. No." is replaced by a reference to compound 132. For example, the first mixture in Table C43 is designated C43-1 and is a mixture of compound 132 and the additional fungicide probenazole.

Table C44

Table C44 is identical to Table C1, except that each reference to compound 6 in the column headed "Cmpd. No." is replaced by a reference to compound 133. For example, the first mixture in Table C44 is designated C44-1 and is a mixture of compound 133 and the additional fungicide probenazole.

Table C45

Table C45 is identical to Table C1, except that each reference to compound 6 in the column headed "Cmpd. No." is replaced by a reference to compound 134. For example, the first mixture in Table C45 is designated C45-1 and is a mixture of compound 134 and the additional fungicide probenazole.

Table C46

Table C46 is identical to Table C1, except that each reference to compound 6 in the column headed "Cmpd. No." is replaced by a reference to compound 135. For example, the first mixture in Table C46 is designated C46-1 and is a mixture of compound 135 and the additional fungicide probenazole.

Table C47

Table C47 is identical to Table C1, except that each reference to compound 6 in the column headed "Cmpd. No." is replaced by a reference to compound 136. For example, the first mixture in Table C47 is designated C47-1 and is a mixture of compound 136 and the additional fungicide probenazole.

Table C48

Table C48 is identical to Table C1, except that each reference to compound 6 in the column headed "Cmpd. No." is replaced by a reference to compound 137. For example, the first mixture in Table C48 is designated C48-1 and is a mixture of compound 137 and the additional fungicide probenazole.

Table C49

Table C49 is identical to Table C1, except that each reference to compound 6 in the column headed "Cmpd. No." is replaced by a reference to compound 138. For example, the first mixture in Table C49 is designated C49-1 and is a mixture of compound 138 and the additional fungicide probenazole.

Table C50

Table C50 is identical to Table C1, except that each reference to compound 6 in the column headed "Cmpd. No." is replaced by a reference to compound 139. For example, the first mixture in Table C50 is designated C50-1 and is a mixture of compound 139 and the additional fungicide probenazole.

Table C51

Table C51 is identical to Table C1, except that each reference to compound 6 in the column headed "Cmpd. No." is replaced by a reference to compound 140. For example, the first mixture in Table C51 is designated C51-1 and is a mixture of compound 140 and the additional fungicide probenazole.

Table C51a

Table C51a is identical to Table C1, except that each reference to compound 6 in the column headed "Cmpd. No." is replaced by a reference to compound 541. For example, the first mixture in Table C51a is designated C51a-1 and is a mixture of compound 541 and the additional invertebrate pest control agent abamectin.

Table C52

Table C52 is identical to Table C1, except that each reference to compound 6 in the column headed "Cmpd. No." is replaced by a reference to compound 542. For example, the first mixture in Table C52 is designated C52-1 and is a mixture of compound 542 and the additional invertebrate pest control agent abamectin.

Table C53

Table C53 is identical to Table C1, except that each reference to compound 6 in the column headed "Cmpd. No." is replaced by a reference to compound 576. For example, the first mixture in Table C53 is designated C53-1 and is a mixture of compound 576 and the additional invertebrate pest control agent abamectin.

Table C54

Table C54 is identical to Table C1, except that each reference to compound 6 in the column headed "Cmpd. No." is replaced by a reference to compound 583. For example, the first mixture in Table C54 is designated C54-1 and is a mixture of compound 583 and the additional invertebrate pest control agent abamectin.

Table C55

Table C55 is identical to Table C1, except that each reference to compound 6 in the column headed "Cmpd. No." is replaced by a reference to compound 594. For example, the first mixture in Table C55 is designated C55-1 and is a mixture of compound 594 and the additional invertebrate pest control agent abamectin.

Table C56

Table C56 is identical to Table C1, except that each reference to compound 6 in the column headed "Cmpd. No." is replaced by a reference to compound 654. For example, the first mixture in Table C56 is designated C56-1 and is a mixture of compound 654 and the additional invertebrate pest control agent abamectin.

Table C57

Table C57 is identical to Table C1, except that each reference to compound 6 in the column headed "Cmpd. No." is replaced by a reference to compound 657. For example, the first mixture in Table C57 is designated C57-1 and is a mixture of compound 657 and the additional invertebrate pest control agent abamectin.

Table C58

Table C58 is identical to Table C1, except that each reference to compound 6 in the column headed "Cmpd. No." is replaced by a reference to compound 669. For example, the first mixture in Table C58 is designated C58-1 and is a mixture of compound 669 and the additional invertebrate pest control agent abamectin.

Table C59

Table C59 is identical to Table C1, except that each reference to compound 6 in the column headed "Cmpd. No." is replaced by a reference to compound 670. For example, the first mixture in Table C59 is designated C59-1 and is a mixture of compound 670 and the additional invertebrate pest control agent abamectin.

Table C60

Table C60 is identical to Table C1, except that each reference to compound 6 in the column headed "Cmpd. No." is replaced by a reference to compound 682. For example, the first mixture in Table C60 is designated C60-1 and is a mixture of compound 682 and the additional invertebrate pest control agent abamectin.

Table C61

Table C61 is identical to Table C1, except that each reference to compound 6 in the column headed "Cmpd. No." is replaced by a reference to compound 683. For example, the first mixture in Table C61 is designated C61-1 and is a mixture of compound 683 and the additional invertebrate pest control agent abamectin.

Table C62

Table C62 is identical to Table C1, except that each reference to compound 6 in the column headed "Cmpd. No." is replaced by a reference to compound 687. For example, the first mixture in Table C62 is designated C62-1 and is a mixture of compound 687 and the additional invertebrate pest control agent abamectin.

Table C63

Table C63 is identical to Table C1, except that each reference to compound 6 in the column headed "Cmpd. No." is replaced by a reference to compound 718. For example, the first mixture in Table C63 is designated C63-1 and is a mixture of compound 718 and the additional invertebrate pest control agent abamectin.

Table C64

Table C64 is identical to Table C1, except that each reference to compound 6 in the column headed "Cmpd. No." is replaced by a reference to compound 725. For example, the first mixture in Table C64 is designated C64-1 and is a mixture of compound 725 and the additional invertebrate pest control agent abamectin.

Table C65

Table C65 is identical to Table C1, except that each reference to compound 6 in the column headed "Cmpd. No." is replaced by a reference to compound 726. For example, the first mixture in Table C65 is designated C65-1 and is a mixture of compound 726 and the additional invertebrate pest control agent abamectin.

Table C66

Table C66 is identical to Table C1, except that each reference to compound 6 in the column headed "Cmpd. No." is replaced by a reference to compound 727. For example, the first mixture in Table C66 is designated C66-1 and is a mixture of compound 727 and the additional invertebrate pest control agent abamectin.

Table C67

Table C67 is identical to Table C1, except that each reference to compound 6 in the column headed "Cmpd. No." is replaced by a reference to compound 734. For example, the first mixture in Table C67 is designated C67-1 and is a mixture of compound 734 and the additional invertebrate pest control agent abamectin.

Table C68

Table C68 is identical to Table C1, except that each reference to compound 6 in the column headed "Cmpd. No." is replaced by a reference to compound 735. For example, the first mixture in Table C68 is designated C68-1 and is a mixture of compound 735 and the additional invertebrate pest control agent abamectin.

Table C69

Table C69 is identical to Table C1, except that each reference to compound 6 in the column headed "Cmpd. No." is replaced by a reference to compound 737. For example, the first mixture in Table C69 is designated C69-1 and is a mixture of compound 737 and the additional invertebrate pest control agent abamectin.

Table C70

Table C70 is identical to Table C1, except that each reference to compound 6 in the column headed "Cmpd. No." is replaced by a reference to compound 744. For example, the first mixture in Table C70 is designated C70-1 and is a mixture of compound 744 and the additional invertebrate pest control agent abamectin.

Table C71

Table C71 is identical to Table C1, except that each reference to compound 6 in the column headed "Cmpd. No." is replaced by a reference to compound 745. For example, the first mixture in Table C71 is designated C71-1 and is a mixture of compound 745 and the additional invertebrate pest control agent abamectin.

Table C72

Table C72 is identical to Table C1, except that each reference to compound 6 in the column headed "Cmpd. No." is replaced by a reference to compound 746. For example, the first mixture in Table C72 is designated C72-1 and is a mixture of compound 746 and the additional invertebrate pest control agent abamectin.

Table C73

Table C73 is identical to Table C1, except that each reference to compound 6 in the column headed "Cmpd. No." is replaced by a reference to compound 748. For example, the first mixture in Table C73 is designated C73-1 and is a mixture of compound 748 and the additional invertebrate pest control agent abamectin.

Table C74

Table C74 is identical to Table C1, except that each reference to compound 6 in the column headed "Cmpd. No." is replaced by a reference to compound 749. For example, the first mixture in Table C74 is designated C74-1 and is a mixture of compound 749 and the additional invertebrate pest control agent abamectin.

Table C75

Table C75 is identical to Table C1, except that each reference to compound 6 in the column headed "Cmpd. No." is replaced by a reference to compound 750. For example, the first mixture in Table C75 is designated C75-1 and is a mixture of compound 750 and the additional invertebrate pest control agent abamectin.

Table C76

Table C76 is identical to Table C1, except that each reference to compound 6 in the column headed "Cmpd. No." is replaced by a reference to compound 926. For example, the first mixture in Table C76 is designated C76-1 and is a mixture of compound 926 and the additional invertebrate pest control agent abamectin.

Table C77

Table C77 is identical to Table C1, except that each reference to compound 6 in the column headed "Cmpd. No." is replaced by a reference to compound 930. For example, the first mixture in Table C77 is designated C77-1 and is a mixture of compound 930 and the additional invertebrate pest control agent abamectin.

Invertebrate pests are controlled in agronomic and nonagronomic applications by applying one or more compositions of this invention, in a biologically effective amount, to the environment of the pests, including the agronomic and/or nonagronomic locus of infestation, to the area to be protected, or directly on the pests to be controlled.

Thus the present invention comprises a method for controlling an invertebrate pest in agronomic and/or nonagronomic applications, comprising contacting the invertebrate pest or its environment with a biologically effective amount of one or more of the compositions of the invention, or with a composition of the invention further comprising at least one additional biologically active compound or agent. Examples of suitable compositions comprising a composition of the invention and a biologically effective amount of at least one additional biologically active compound or agent include granular compositions wherein the additional active compound is present on the same granule as the composition of the invention or on granules separate from those of the composition of the invention.

Embodiments of the method of this invention include contacting the environment. Of note is the method wherein the environment is a plant. Also of note is the method wherein the environment is an animal. Also of note is the method wherein the environment is a seed.

To achieve contact with a composition of the invention to protect a field crop from invertebrate pests, the composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a composition of the invention can be applied to the plant foliage or the soil. Compositions of this invention can also be effectively delivered through plant uptake by contacting the plant with a composition comprising a composition of this invention applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the invertebrate pest or its environment with a composition comprising a biologically effective amount of a composition of the present invention. Of further note is this method wherein the environment is soil and the composition is applied to the soil as a soil drench formulation. Of further note is that compositions of this invention are also effective by localized application to the locus of infestation. Other methods of contact include application of a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compositions of this invention can also be impregnated into materials for fabricating invertebrate control devices (e.g., insect netting).

Compositions of this invention are also useful in seed treatments for protecting seeds from invertebrate pests. In the context of the present disclosure and claims, treating a seed means contacting the seed with a biologically effective amount of a composition of this invention. This seed treatment protects the seed from invertebrate soil pests and generally can also protect roots and other plant parts in contact with the soil of the seedling developing from the germinating seed. The seed treatment may also provide protection of foliage by translocation of the compound of Formula 1 or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate.

One method of seed treatment is by spraying or dusting the seed with a composition of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1, an N-oxide or salt thereof, and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment Progress and Prospects*, 1994 BCPC Mongraph No. 57, and references listed therein.

The treated seed typically comprises a composition of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compositions of this invention can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1 an N-oxide or salt thereof; (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches.

A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The composition of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a composition of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as needed for application. Of note is a spray composition comprising a biologically effective amount of a compound or a composition of the present invention and a carrier. One embodiment of such a spray composition comprises a biologically effective amount of a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

Nonagronomic uses refer to invertebrate pest control in the areas other than fields of crop plants. Nonagronomic uses of the present compositions include control of invertebrate pests in stored grains, beans and other foodstuffs, and in textiles such as clothing and carpets. Nonagronomic uses of the present compositions also include invertebrate pest control in ornamental plants, forests, in yards, along roadsides and railroad rights of way, and on turf such as lawns, golf courses and pastures. Nonagronomic uses of the present compositions also include invertebrate pest control in houses and other buildings which may be occupied by humans and/or companion, farm, ranch, zoo or other animals. Nonagronomic uses of the present compositions also include the control of pests such as termites that can damage wood or other structural materials used in buildings.

Nonagronomic uses of the present compositions also include protecting human and animal health by controlling invertebrate pests that are parasitic or transmit infectious diseases. The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. Compositions of the present invention are particularly suitable for combating external parasitic or disease transmitting pests. Compositions of the present invention are suitable for systemic and/or non-systemic control of infestation or infection by parasites on animals.

Compositions of the present invention are suitable for combating parasites that infest animal subjects including those in the wild, livestock and agricultural working animals such as cattle, sheep, goats, horses, pigs, donkeys, camels, bison, buffalos, rabbits, hens, turkeys, ducks, geese and bees (e.g., raised for meat, milk, butter, eggs, fur, leather, feathers and/or wool). By combating parasites, fatalities and performance reduction (in terms of meat, milk, wool, skins, eggs, honey, etc.) are reduced, so that applying a composition comprising a compound of the present invention allows more economic and simple husbandry of animals.

Compositions of the present invention are especially suitable for combating parasites that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, bison, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the inventive compositions can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws, and parrots raised for the pet or collector market, among others.

For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of invertebrate parasitic pests controlled by administering a parasiticidally effective amount of a composition of this invention to an animal to be protected include ectoparasites (arthropods, acarines, etc) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the Helminths, the group of worms described as nematodes causes widespread and at times serious infection in various species of animals. Nematodes that are contemplated to be treated by the compositions of this invention and by the inventive methods include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the compositions of this invention and by the inventive methods include, without limitation, the following genera: *Alaria, Fasciola, Nanophyetus, Opisthorchis, Paragonimus* and *Schistosoma*.

Cestodes that are contemplated to be treated by the compositions of this invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongyloides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other Helminth genera and species are known to the art, and are also contemplated to be treated by the compositions of the invention. These are enumerated in great detail in *Textbook of Veterinary Clinical Parasitology*, Volume 1, Helminths, E. J. L. Soulsby, F. A. Davis Co., Philadelphia, Pa.; *Helminths, Arthropods and Protozoa*, (6th Edition of Monnig's Veterinary Helminthology and Entomology), E. J. L. Soulsby, The Williams and Wilkins Co., Baltimore, Md.

It is also contemplated that the inventive compositions are effective against a number of ectoparasites of animals, e.g., arthropod ectoparasites of mammals and birds although it is also recognized that some arthropods can be endoparasites as well.

Thus, insect and acarine pests include, e.g., biting insects, such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp., and *Aedes* spp.

Mites include *Mesostigmata* spp. e.g., mesostigmatids such as the chicken mite, *Dermanyssus gallinae*; itch or scab mites such as Sarcoptidae spp. for example, *Sarcoptes scabiei*; mange mites such as Psoroptidae spp. including *Chorioptes bovis* and *Psoroptes ovis*; chiggers e.g., Trombiculidae spp. for example the North American chigger, *Trombicula alfreddugesi*.

Ticks include, e.g., soft-bodied ticks including Argasidae spp. for example *Argas* spp. and *Ornithodoros* spp.; hard-bodied ticks including Ixodidae spp., for example *Rhipicephalus sanguineus, Dermacentor variabilis, Dermacentor andersoni, Amblyomma americanum, Ixodes scapularis* and *Boophilus* spp.

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides fells*); *Xenopsylla* spp. such as oriental rat flea (*Xenopsylla cheopis*); and *Pulex* spp. such as human flea (*Pulex irritans*).

True bugs include, e.g., Cimicidae or e.g., the common bed bug (*Cimex lectularius*); Triatominae spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other arthropod pests and ectoparasites are known to the art, and are also contemplated to be treated by the compositions of the invention. These are enumerated in great detail in *Medical and Veterinary Entomology*, D. S. Kettle, John Wiley & Sons, New York and Toronto; *Control of Arthropod Pests of Livestock: A Review of Technology*, R. O. Drummand, J. E. George, and S. E. Kunz, CRC Press, Boca Raton, Fla.

The compositions of this invention may also be effective against a number of protozoa endoparasites of animals, such as those summarized by Table 1, as follows.

TABLE 1

Exemplary Parasitic Protozoa and Associated Human Diseases

| Phylum | Subphylum | Representative Genera | Human Disease or Disorder |
|---|---|---|---|
| Sarcomastigophora (with flagella, pseudopodia, or both) | Mastigophora (Flagella) | Leishmania | Visceral, cutaneous and mucocutaneous Infection |

TABLE 1-continued

Exemplary Parasitic Protozoa and Associated Human Diseases

| Phylum | Subphylum | Representative Genera | Human Disease or Disorder |
|---|---|---|---|
| | | Trypansoma | Sleeping sickness Chagas' disease |
| | Sarcodina (pseudopodia) | Giardia | Diarrhea |
| | | Trichomonas | Vaginitis |
| | | Entamoeba | Dysentery, liver Abscess |
| | | Dientamoeba | Colitis |
| | | Naegleria and Acanthamoeba | Central nervous system and corneal ulcers |
| | | Babesia | Babesiesis |
| Apicomplexa (apical complex) | | Plasmodium | Malaria |
| | | Isospora | Diarrhea |
| | | Sarcocystis | Diarrhea |
| | | Cryptosporidum | Diarrhea |
| | | Toxoplasma | Toxoplasmosis |
| | | Eimeria | Chicken coccidiosis |
| Microspora | | Enterocytozoon | Diarrhea |
| Ciliaphora (with cilia) | | Balantidium | Dysentery |
| Unclassified | | Pneumocystis | Pneumonia |

In particular, the compositions of this invention are effective against ectoparasites including fleas such as *Ctenocephalides felis* (cat flea) and *Ctenocephalides canis* (dog flea).

The compositions of this invention may also be effective against other ectoparasites including flies such as *Haematobia (Lyperosia) irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus instestinalis, Gastrophilus haemorrhoidalis* and *Gastrophilus naslis*; lice such as *Bovicola (Damalinia) bovis, Bovicola equi, Haematopinus asini, Felicola subrostratus, Heterodoxus spiniger, Lignonathus setosus* and *Trichodectes canis*; keds such as *Melophagus ovinus*; mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites); and ticks such as *Ixodes* spp., *Boophilus* spp., *Rhipicephalus* spp., *Amblyomma* spp., *Dermacentor* spp., *Hyalomma* spp. and *Haemaphysalis* spp.

Biologically active compounds or agents useful in the compositions of the present invention include the organophosphate pesticides. This class of pesticides has very broad activity as insecticides and, in certain instances, anthelminitic activity. Organophosphate pesticides include, e.g., dicrotophos, terbufos, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion and phosalone. It is also contemplated to include combinations of the inventive methods and compounds with carbamate type pesticides, including, e.g., carbaryl, carbofuran, aldicarb, molinate, methomyl, carbofuran, etc., as well as combinations with the organochlorine type pesticides. It is further contemplated to include combinations with biological pesticides, including repellents, the pyrethrins (as well as synthetic variations thereof, e.g., allethrin, resmethrin, permethrin, tralomethrin), and nicotine, that is often employed as an acaricide. Other contemplated combinations are with miscellaneous pesticides including: *bacillus thuringensis*, chlorobenzilate, formamidines (e.g., amitraz), copper compounds (e.g., copper hydroxide and cupric oxychloride sulfate), cyfluthrin, cypermethrin, dicofol, endosulfan, esenfenvalerate, fenvalerate, lambda-cyhalothrin, methoxychlor and sulfur.

Of note are additional biologically active compounds or agents selected from art-known anthelmintics, such as, for example, avermectins (e.g., ivermectin, moxidectin, milbemycin), benzimidazoles (e.g., albendazole, triclabendazole), salicylanilides (e.g., closantel, oxyclozanide), substituted phenols (e.g., nitroxynil), pyrimidines (e.g., pyrantel), imidazothiazoles (e.g., levamisole) and praziquantel.

Other biologically active compounds or agents useful in the compositions of the present invention can be selected from Insect Growth Regulators (IGRs) and Juvenile Hormone Analogues (JHAs) such as diflubenzuron, triflumuron, fluazuron, cyromazine, methoprene, etc., thereby providing both initial and sustained control of parasites (at all stages of insect development, including eggs) on the animal subject, as well as within the environment of the animal subject.

Of note are biologically active compounds or agents useful in the compositions of the present invention selected from the antiparasitic class of avermectin compounds. As stated above, the avermectin family of compounds is a series of very potent antiparasitic agents known to be useful against a broad spectrum of endoparasites and ectoparasites in mammals.

A notable compound for use within the scope of the present invention is ivermectin. Ivermectin is a semi-synthetic derivative of avermectin and is generally produced as a mixture of at least 80% 22,23-dihydroavermectin $B_{1a}$ and less than 20% 22,23-dihydroavermectin $B_{1b}$. Ivermectin is disclosed in U.S. Pat. No. 4,199,569.

Abamectin is an avermectin that is disclosed as Avermectin $B_{1a}/B_{1b}$ in U.S. Pat. No. 4,310,519. Abamectin contains at least 80% of avermectin $B_{1a}$ and not more than 20% of avermectin $B_{1b}$.

Another notable avermectin is Doramectin, also known as 25-cyclohexyl-avermectin $B_1$. The structure and preparation of Doramectin is disclosed in U.S. Pat. No. 5,089,480.

Another notable avermectin is Moxidectin. Moxidectin, also known as LL-F28249 alpha, is known from U.S. Pat. No. 4,916,154.

Another notable avermectin is Selamectin. Selamectin is 25-cyclohexyl-25-de(1-methylpropyl)-5-deoxy-22,23-dihydro-5-(hydroxyimino)-avermectin $B_1$ monosaccharide.

Milbemycin, or B41, is a substance which is isolated from the fermentation broth of a Milbemycin producing strain of *Streptomyces*. The microorganism, the fermentation conditions and the isolation procedures are more fully described in U.S. Pat. No. 3,950,360 and U.S. Pat. No. 3,984,564.

Emamectin (4"-deoxy-4"-epi-methylaminoavermectin $B_1$), which can be prepared as described in U.S. Pat. No. 5,288,710 or U.S. Pat. No. 5,399,717, is a mixture of two homologues, 4"-deoxy-4"-epi-methylaminoavermectin $B_{1a}$ and 4"-deoxy-4"-epi-methylaminoavermectin $B_{1b}$. Preferably, a salt of Emamectin is used. Non-limiting examples of salts of Emamectin which can be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the Emamectin salt used in the present invention is Emamectin benzoate.

Eprinomectin is chemically known as 4"-epi-acetylamino-4"-deoxy-avermectin $B_1$. Eprinomectin was specifically developed to be used in all cattle classes and age groups. It was the first avermectin to show broad-spectrum activity against both endo- and ectoparasites while also leaving minimal residues in meat and milk. It has the additional advantage of being highly potent when delivered topically.

The composition of the present invention optionally comprises combinations of one or more of the following antiparasite compounds: imidazo[1,2-b]pyridazine compounds as described by U.S. application Ser. No. 11/019,597, filed on Dec. 22, 2004; 1-(4-mono and di-halomethylsulphonylphenyl)-2-acylamino-3-fluoropropanol compounds, as described by U.S. application Ser. No. 11/018,156, filed on Dec. 21, 2004; trifluoromethanesulfonanilide oxime ether derivatives, as described by U.S. application Ser. No. 11/231,423, filed on Sep. 21, 2005; and n-[(phenyloxy)phenyl]-1,1,1-trifluoromethanesulfonamide and n-[(phenylsulfanyl)phenyl]-1,1,1-trifluoromethanesulfonamide derivatives, as described by U.S. Provisional Application Ser. No. 60/688,898, filed on Jun. 9, 2005.

The compositions of the present invention can also further comprise a flukicide. Suitable flukicides include, for example, triclabendazole, fenbendazole, albendazole, Clorsulon and oxibendazole. It will be appreciated that the above combinations can further include combinations of antibiotic, antiparasitic and anti-fluke active compounds.

In addition to the above combinations, it is also contemplated to provide combinations of the inventive methods and compositions, as described herein, with other animal health remedies such as trace elements, anti-inflammatories, anti-infectives, hormones, dermatological preparations, including antiseptics and disinfectants, and immunobiologicals such as vaccines and antisera for the prevention of disease.

For example, such antinfectives include one or more antibiotics that are optionally co-administered during treatment using the inventive compositions or methods, e.g., in a combined composition and/or in separate dosage forms. Art-known antibiotics suitable for this purpose include, for example, those listed herein below.

One useful antibiotic is Florfenicol, also known as D-(threo)-1-(4-methylsulfonylphenyl)-2-dichloroacetamido-3-fluoro-1-propanol. Another notable antibiotic compound is D-(threo)-1-(4-methylsulfonyphenyl)-2-difluoroacetamido-3-fluoro-1-propanol. Another useful antibiotic is Thiamphenicol. Processes for the manufacture of these antibiotic compounds, and intermediates useful in such processes, are described in U.S. Pat. No. 4,311,857; U.S. Pat. No. 4,582,918; U.S. Pat. No. 4,973,750; U.S. Pat. No. 4,876,352; U.S. Pat. No. 5,227,494; U.S. Pat. No. 4,743,700; U.S. Pat. No. 5,567,844; U.S. Pat. No. 5,105,009; U.S. Pat. No. 5,382,673; U.S. Pat. No. 5,352,832; and U.S. Pat. No. 5,663,361. Other florfenicol analogs and/or prodrugs have been disclosed and such analogs also can be used in the compositions and methods of the present invention (see e.g., U.S. Patent Application Publication No: 2004/0082553, and U.S. patent application Ser. No. 11/016,794).

Another useful antibiotic compound is Tilmicosin. Tilmicosin is a macrolide antibiotic that is chemically defined as 20-dihydro-20-deoxy-20-(cis-3,5-dimethylpiperidin-1-yl)-desmycosin and which is reportedly disclosed in U.S. Pat. No. 4,820,695.

Another useful antibiotic for use in the present invention is tulathromycin. Tulathromycin is also identified as (2R,3S,4R, 5R,8R,10R,11R,12S,13S,14R) 13-[(2,6-dideoxy-3-C-methyl-3-O-methyl-4-C-[(propylamino)methyl]-alpha-L-ribo-hexopyranosyl]-oxy]-2-ethyl-3,4,10-trihydroxy-3,5,8,10,12, 14-hexamethyl-11-[[3,4,6-trideoxy-3-(dimethyl-amino)-beta-D-xylo-hexopyranosyl]oxy]-1-oxa-6-azacyclopentadecan-15-one. Tulathromycin can be prepared in accordance with the procedures set forth in U.S. Patent Publication No. 2003/0064939 A1.

Further antibiotics for use in the present invention include the cephalosporins such as, for example, ceftiofur, cefquinome, etc. The concentration of the cephalosporin in the formulation of the present invention optionally varies between about 1 mg/mL to 500 mg/mL.

Another useful antibiotic includes the fluoroquinolones, such as, for example, enrofloxacin, danofloxacin, difloxacin, orbifloxacin and marbofloxacin. Enrofloxacin is typically administered in a concentration of about 100 mg/mL. Danofloxacin is typically administered at a concentration of about 180 mg/mL.

Other useful macrolide antibiotics include compounds from the class of ketolides, or, more specifically, the azalides. Such compounds are described in, for example, U.S. Pat. No. 6,514,945, U.S. Pat. No. 6,472,371, U.S. Pat. No. 6,270,768, U.S. Pat. No. 6,437,151, U.S. Pat. No. 6,271,255, U.S. Pat. No. 6,239,112, U.S. Pat. No. 5,958,888, U.S. Pat. No. 6,339,063 and U.S. Pat. No. 6,054,434.

Other useful antibiotics include the tetracyclines, particularly chlortetracycline and oxytetracycline. Other antibiotics may include β-lactams such as penicillins, e.g., penicillin, ampicillin, amoxicillin, or a combination of amoxicillin with clavulanic acid or other beta lactamase inhibitors.

Nonagronomic applications in the veterinary sector are by conventional means such as by enteral administration in the form of, for example, tablets, capsules, drinks, drenching preparations, granulates, pastes, boli, feed-through procedures, or suppositories; or by parenteral administration, such as by injection (including intramuscular, subcutaneous, intravenous, intraperitoneal) or implants; by nasal administration; by topical administration, for example, in the form of immersion or dipping, spraying, washing, coating with powder, or application to a small area of the animal, and through articles such as neck collars, ear tags, tail bands, limb bands or halters which comprise compositions of the present invention.

Any of the compositions of the present invention, or a suitable combination of such compositions, may be administered directly to the animal subject and/or indirectly by applying it to the local environment in which the animal dwells (such as bedding, enclosures, or the like). Direct administration includes contacting the skin, fur or feathers of a subject animal with the compositions, or by feeding or injecting the compositions into the animal.

The compositions of the present invention may be administered in a controlled release form, e.g., in a subcutaneous slow release formulation, or in the form of a controlled release device affixed to an animal such as a fleacollar. Collars for the controlled release of an insecticide agent for long term protection against flea infestation in a companion animal are art-known, and are described, for example, by U.S. Pat. No. 3,852,416, U.S. Pat. No. 4,224,901, U.S. Pat. No. 5,555,848 and U.S. Pat. No. 5,184,573.

Typically a parasiticidal composition according to the present invention comprises a mixture of a compound of Formula 1, an N-oxide or salt thereof, with one or more pharmaceutically or veterinarily acceptable carriers comprising excipients and auxiliaries selected with regard to the intended route of administration (e.g., oral, topical or parenteral administration such as injection) and in accordance with standard practice. In addition, a suitable carrier is selected on the basis of compatibility with the one or more active ingredients in the composition, including such considerations as stability relative to pH and moisture content. Therefore of note is a composition for protecting an animal from an invertebrate parasitic pest comprising a parasitically effective amount of a compound of the invention and at least one carrier.

For parenteral administration including intravenous, intramuscular and subcutaneous injection, a composition of the present invention can be formulated in suspension, solution or emulsion in oily or aqueous vehicles, and may contain adjuncts such as suspending, stabilizing and/or dispersing agents. The compositions of the present invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compositions of the present invention may also be formulated as a depot preparation. Such long acting formulations may be administered by implantation (for example, subcutaneously or intramuscularly) or by intramuscular or subcutaneous injection. The compositions of the present invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compositions of the present invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the composition and a suitable powder base such as lactose or starch.

Compositions of the present invention have been discovered to have favorable pharmacokinetic and pharmacodynamic properties providing systemic availability from oral administration and ingestion. Therefore after ingestion by the animal to be protected, parasiticidally effective concentrations of compounds of the invention in the bloodstream protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, a composition of the present invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The compounds of Formula 1 may also be formulated in rectal compositions such as suppositories or retention enemas, using, e.g., conventional suppository bases such as cocoa butter or other glycerides.

Formulations for topical administration are typically in the form of a powder, cream, suspension, spray, emulsion, foam, paste, aerosol, ointment, salve or gel. More typically a topical formulation is a water-soluble solution, which can be in the form of a concentrate that is diluted before use. Parasiticidal compositions suitable for topical administration typically comprise a compound of the present invention and one or more topically suitable carriers. In applications of a parasiticidal composition topically to the exterior of an animal as a line or spot (i.e. "spot-on" treatment), the active ingredient migrates over the surface of the animal to cover most or all of its external surface area. As a result, the treated animal is particularly protected from invertebrate pests that feed off the epidermis of the animal such as ticks, fleas and lice. Therefore formulations for topical localized administration often comprise at least one organic solvent to facilitate transport of the active ingredient over the skin and/or penetration into the epidermis of the animal. Carriers in such formulations include propylene glycol, paraffins, aromatics, esters such as isopropyl myristate, glycol ethers, alcohols such as ethanol, n-propanol, 2-octyl dodecanol or oleyl alcohol; solutions in esters of monocarboxylic acids, such as isopropyl myristate, isopropyl palmitate, lauric acid oxalic ester, oleic acid oleyl ester, oleic acid decyl ester, hexyl laurate, oleyl oleate, decyl oleate, caproic acid esters of saturated fatty alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or solutions of esters of aliphatic acids, e.g., glycols. It may be advantageous for a crystallization inhibitor or a dispersant known from the pharmaceutical or cosmetic industry also to be present.

A pour-on formulation may also be prepared for control of parasites in an animal of agricultural worth. The pour-on formulations of this invention can be in the form of a liquid, powder, emulsion, foam, paste, aerosol, ointment, salve or gel. Typically, the pour-on formulation is liquid. These pour-on formulations can be effectively applied to sheep, cattle, goats, other ruminants, camelids, pigs and horses. The pour-on formulation is typically applied by pouring in one or several lines or in a spot-on the dorsal midline (back) or shoulder of an animal. More typically, the formulation is applied by pouring it along the back of the animal, following the spine. The formulation can also be applied to the animal by other conventional methods, including wiping an impregnated material over at least a small area of the animal, or applying it using a commercially available applicator, by means of a syringe, by spraying or by using a spray race. The pour-on formulations include a carrier and can also include one or more additional ingredients. Examples of suitable additional ingredients are stabilizers such as antioxidants, spreading agents, preservatives, adhesion promoters, active solubilisers such as oleic acid, viscosity modifiers, UV blockers or absorbers, and colourants. Surface active agents, including anionic, cationic, non-ionic and ampholytic surface active agents, can also be included in these formulations.

The formulations of this invention typically include an antioxidant, such as BHT (butylated hydroxytoluene). The antioxidant is generally present in amounts of at 0.1-5% (wt/vol). Some of the formulations require a solubilizer, such as oleic acid, to dissolve the active agent, particularly if spinosad is used. Common spreading agents used in these pour-on formulations are: IPM, IPP, caprylic/capric acid esters of saturated $C_{12}$-$C_{18}$ fatty alcohols, oleic acid, oleyl ester, ethyl oleate, triglycerides, silicone oils and DPM. The pour-on formulations of this invention are prepared according to known techniques. Where the pour-on is a solution, the parasiticide/insecticide is mixed with the carrier or vehicle, using heat and stirring where required. Auxiliary or additional ingredients can be added to the mixture of active agent and carrier, or they can be mixed with the active agent prior to the addition of the carrier. If the pour-on is an emulsion or suspension, these formulations are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

For agronomic applications, the rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

In general for veterinary use, a composition of this invention is administered in a parasiticidally effective amount to an animal to be protected from invertebrate parasite pests. A parasiticidally effective amount is the amount of active ingredient needed to achieve an observable effect diminishing the occurrence or activity of the target invertebrate parasite pest. One skilled in the art will appreciate that the parasitically effective dose can vary for the various compounds and compositions of the present invention, the desired parasitical effect and duration, the target invertebrate pest species, the animal to be protected, the mode of application and the like, and the amount needed to achieve a particular result can be determined through simple experimentation.

For oral administration to homeothermic animals, the daily dosage of a composition of the present invention typically ranges from about 0.01 mg/kg to about 100 mg/kg, more typically from about 0.5 mg/kg to about 100 mg/kg, of animal body weight. For topical (e.g., dermal) administration, dips and sprays typically contain from about 0.5 ppm to about 5000 ppm, more typically from about 1 ppm to about 3000 ppm, of a compound of the present invention.

Representative compounds of Formula 1 useful in the compositions of this invention are shown in Index Tables A-C. See Index Table D for $^1$H NMR data. For mass spectral data (AP$^+$ (M+1)), the numerical value reported is the molecular weight of the parent molecular ion (M) formed by addition of H$^+$ (molecular weight of 1) to the molecule to give a M+1 peak observed by mass spectrometry using atmospheric pressure chemical ionization (AP$^+$). The alternate molecular ion peaks (e.g., M+2 or M+4) that occur with compounds containing multiple halogens are not reported. The variable "RA" in Index Table A represents one or a combination of substituents as listed in Index Table A.

The following additional abbreviations are used in the Index Tables which follow: Cmpd means Compound, CN is cyano. A "-" entry in Table A indicates no substitution.

Fragments X-1 through X-27 shown below are referred to in the Index Tables. The wavy line denotes the attachment point of the fragment to the remainder of the molecule.

X-1

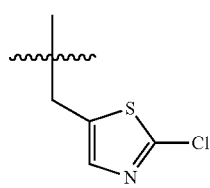

X-2

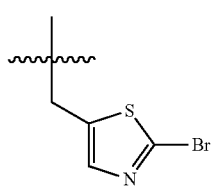

-continued

X-3

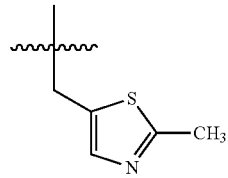

X-4

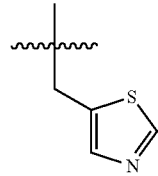

X-5

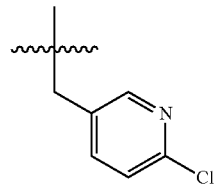

X-6

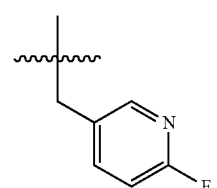

X-7

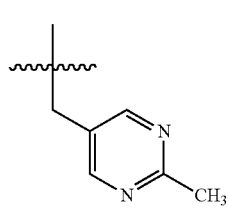

X-8

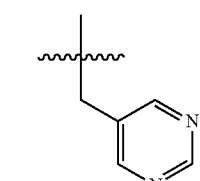

X-9

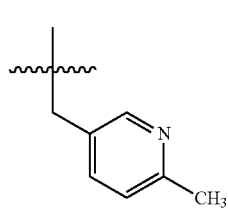

X-10

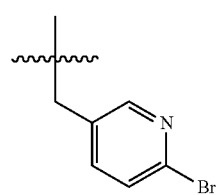

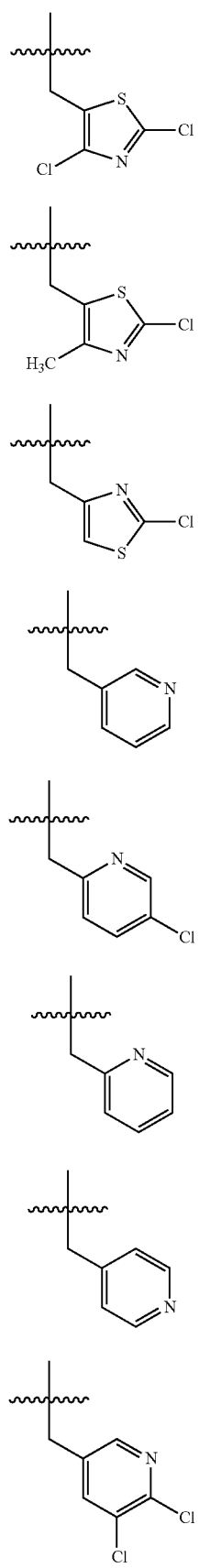
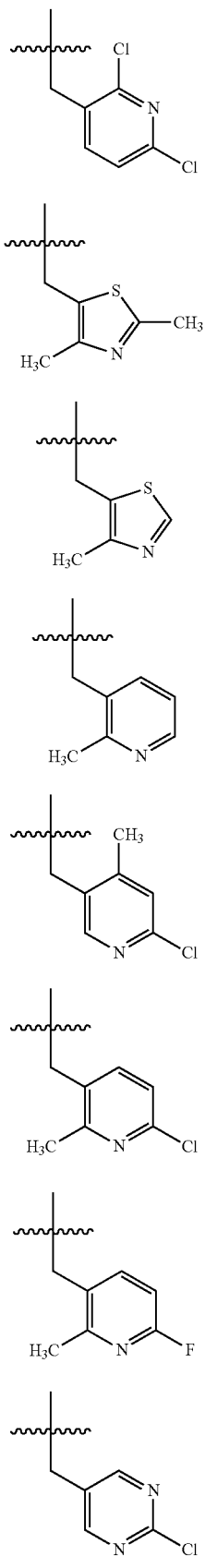

INDEX TABLE A

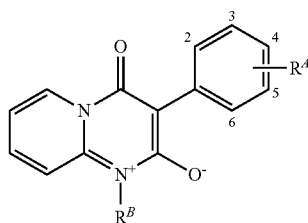

| Cmpd | $R^A$ | $R^B$ | m.p. (° C.) | AP+ (M + 1) |
|---|---|---|---|---|
| 1 | 2-F, 3-Cl, 5-CF$_3$ | X-6 | | 468 |
| 2 | 2-F, 3-Cl, 5-CF$_3$ | X-2 | | 534 |
| 3 | 2-OCH$_3$, 5-(6-CF$_3$-3-pyridinyl) | X-1 | | 545 |
| 4 | 2-OCH$_3$, 5-(6-CF$_3$-3-pyridinyl) | X-2 | | 589 |
| 5 | 2-F, 3-F | X-1 | | 406 |
| 6 | 2-OCH$_3$, 5-Cl | X-6 | | 412 |
| 7 | 2-OCH$_3$, 5-Cl | X-1 | | 434 |
| 8 | 2-OCH$_3$, 5-CF$_3$ | X-6 | | 446 |
| 9 | 2-OCH$_3$, 5-CF$_3$ | X-1 | | 468 |
| 10 | 2-F, 4-F | X-4 | | 372 |
| 11 | 2-F, 4-F | X-3 | | 386 |
| 12 | 3-I | X-2 | | 540 |
| 13 | 3-Br, 5-Br | X-1 | | 526 |
| 14 | 3-Br, 5-(6-CF$_3$-3-pyridinyl) | X-1 | | 593 |
| 15 | — | X-8 | | * |
| 16 | 3-OCH$_3$ | X-4 | | 366 |
| 17 | 3-OCH$_3$ | X-3 | | 380 |
| 18 | 2-F | X-4 | | 354 |
| 19 | 2-F | X-3 | | 368 |
| 20 | 2-OCH$_3$ | X-4 | | 366 |
| 21 | 2-OCH$_3$ | X-3 | | 380 |
| 22 | 3-CF$_3$ | X-4 | | 404 |
| 23 | 3-CF$_3$ | X-3 | | 418 |
| 24 | 3-OCF$_3$ | X-4 | | 420 |
| 25 | 3-OCF$_3$ | X-3 | | 434 |
| 26 | 2-Cl, 6-F | X-5 | | 416 |
| 27 | 2-Cl, 6-F | X-6 | | 400 |
| 28 | 2-Cl, 6-F | X-1 | | 422 |
| 29 | 2-OCH$_2$CH$_3$ | X-1 | | 414 |
| 30 | 2-OCH$_3$, 5-OCF$_3$ | X-1 | | 484 |
| 31 | 2-F, 5-OCF$_3$ | X-6 | | 450 |
| 32 | 3-(6-CF$_3$-3-pyridinyl) | X-3 | | 495 |
| 33 | 2-CH$_3$ | X-1 | | 384 |
| 34 | 3-CH$_3$ | X-1 | | 384 |
| 35 | 2-OCH$_2$CH$_2$CH$_3$ | X-1 | | 428 |
| 36 | 2-OCH(CH$_3$)$_2$ | X-1 | | 428 |
| 37 | 2-CH$_2$CH$_3$ | X-1 | | 398 |
| 38 | 4-F | X-8 | | * |
| 39 | 3-CF$_3$ | X-8 | | 399 |
| 40 | 2-OCH$_3$ | X-8 | | * |
| 41 | 3-OCH$_3$ | X-8 | | 361 |
| 42 | 2-F, 4-F | X-8 | | * |
| 43 | 3-OCF$_3$ | X-8 | | * |
| 44 | 3-Br | X-8 | | * |
| 45 | 3-(2-chlorophenyl) | X-1 | | 480 |
| 46 | 3-(3-chlorophenyl) | X-1 | | 480 |
| 47 | 2-F, 3-Cl | X-1 | | 422 |
| 48 | 2-F, 3-Cl | X-5 | | 416 |
| 49 | 2-F, 3-(6-CF$_3$-3-pyridinyl) | X-1 | | 533 |
| 50 | 2-F, 3-Br | X-1 | | 466 |
| 51 | 2-F, 3-CF$_3$ | X-1 | | 456 |
| 52 | 3-OCH$_3$, 4-F | X-1 | | 418 |
| 53 | 3-(4-chlorophenyl) | X-1 | | 480 |
| 54 | 3-(4-fluorophenyl) | X-1 | | 464 |
| 55 | 3-(4-(trifluoromethyl)phenyl) | X-1 | | 514 |
| 56 | 2-F, 6-F | X-1 | | 406 |
| 57 | 2-OCH$_3$, 5-Br | X-6 | | 458 |
| 58 | 2-F, 5-Cl | X-6 | | 400 |
| 59 | 3-CH$_2$CH$_3$ | X-1 | | 398 |
| 60 | 3-OCH$_2$CF$_3$ | X-1 | | 468 |
| 61 | 3-(3,4-dichlorophenyl) | X-1 | | 514 |
| 62 | 3-(3,5-dichlorophenyl) | X-1 | | 514 |
| 63 | 3-Cl, 5-OCF$_3$ | X-2 | | 534 |
| 64 | 3-Cl, 5-OCF$_3$ | X-4 | | 454 |
| 65 | 2-F, 5-F | X-1 | | 482 |

INDEX TABLE A-continued

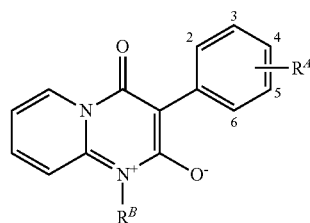

| Cmpd | $R^A$ | $R^B$ | m.p. (° C.) | AP+ (M + 1) |
|---|---|---|---|---|
| 66 | 3-(2,3-dichlorophenyl) | X-1 | | 514 |
| 67 | 3-(2,4-dichlorophenyl) | X-1 | | 514 |
| 68 | 3-(3-(trifluoromethyl)phenyl) | X-1 | | 514 |
| 69 | 3-(2-fluoro-5-(trifluoromethyl)phenyl) | X-1 | | 532 |
| 70 | 2-F | X-8 | | 349 |
| 71 | 2-F, 6-F | $CH_2CF_3$ | | 357 |
| 72 | 3-(2-fluorophenyl) | X-1 | | 464 |
| 73 | 2-$OCH_3$, 5-$OCH_3$ | X-1 | | 430 |
| 74 | 2-F, 5-$CF_3$ | X-8 | | 417 |
| 75 | 2-F, 6-$OCH_3$ | X-1 | | 418 |
| 76 | 2-$OCH_3$, 5-$OCH_3$ | X-6 | | 408 |
| 77 | 2-$OCH_3$, 5-$OCH_3$ | X-5 | | 424 |
| 78 | 2-$OCH_3$, 5-$OCF_3$ | X-6 | | 462 |
| 79 | 2-$OCH_3$, 5-$OCF_3$ | X-1 | | 484 |
| 80 | 2-$OCH_3$, 5-$OCF_3$ | X-5 | | 478 |
| 81 | 2-$OCH_3$, 5-F | X-6 | | 396 |
| 82 | 2-$OCH_3$, 5-F | X-1 | | 418 |
| 83 | 2-$OCH_3$, 5-F | X-5 | | 412 |
| 84 | 3-Cl, 5-Br | X-1 | | 482 |
| 85 | 3-$CF_3$ | X-7 | | 413 |
| 86 | 3-$CH_3$, 5-$CH_3$ | X-5 | | 392 |
| 87 | — | X-7 | | 345 |
| 88 | 2-F | X-7 | | 429 |
| 89 | 3-$OCF_3$ | X-7 | | * |
| 90 | 2-F, 6-F | X-7 | | * |
| 91 | 3-$CF_3$ | X-9 | | 412 |
| 92 | 3-(5-chloro-2-fluorophenyl) | X-1 | | 498 |
| 93 | 2-Cl, 3-Cl | X-1 | | 438 |
| 94 | 3-$OCH_2CH_3$ | X-1 | | 414 |
| 95 | 3-(2,5-dichlorophenyl) | X-1 | | 514 |
| 96 | 4-$CH_3$ | X-1 | | 384 |
| 105 | 2-F, 6-F | X-1 | | 406 |
| 106 | 3-$OCH_3$, 5-$OCH_3$ | X-1 | | 430 |
| 107 | 2-$OCH_3$ | X-1 | | 400 |
| 108 | 3-$OCH_3$, 5-$OCH_3$ | X-6 | | 408 |
| 109 | 3-$CF_3$ | X-6 | | 416 |
| 110 | 2-F, 3-$OCH_3$ | X-5 | | 412 |
| 111 | 4-F | X-3 | | 368 |
| 112 | — | X-4 | | 336 |
| 113 | 2-F | X-6 | | 366 |
| 114 | 3-$OCF_3$ | X-6 | | 432 |
| 115 | 2-$OCH_3$, 5-Br | X-5 | | 474 |
| 116 | 2-Cl, 5-$CF_3$ | X-5 | | 466 |
| 117 | 2-F, 3-$CF_3$ | X-5 | | 434 |
| 118 | 3-Cl, 5-$OCF_3$ | X-1 | | 488 |
| 119 | 3-Cl, 5-$CF_3$ | X-1 | | 472 |
| 120 | 2-F, 3-F, 6-F | X-5 | | 418 |
| 121 | 2-F, 3-Cl, 6-F | X-5 | | 434 |
| 122 | 2-F, 3-F | X-6 | | 384 |
| 125 | 2-F, 4-F | X-6 | 226-228 | |
| 126 | 2-F, 6-F | X-5 | | 400 |
| 127 | 3-$OCH_3$ | X-5 | | * |
| 128 | 2-F | X-5 | | * |
| 129 | 2-F, 5-F | X-5 | | * |
| 130 | 2-F, 5-Cl | X-5 | | * |
| 131 | 2-F, 4-F, 6-F | X-5 | | * |
| 132 | 2-F, 3-F | X-5 | | * |
| 133 | 2-F, 5-Br | X-5 | | * |
| 134 | 3-$OCF_3$ | X-1 | 123-125 | |
| 135 | 2-F, 4-F | X-10 | | 444 |
| 136 | 3-$OCH_3$ | X-1 | 184-186 | |
| 137 | 3-Br, 5-$OCF_3$ | X-1 | 209-210 | |
| 138 | 3-Br, 5-$CF_3$ | X-1 | | 516 |
| 140 | 2-F, 4-cyano | X-6 | | 391 |
| 123 | 3-$OCF_3$, 5-(6-F-3-pyridinyl) | X-1 | | 549 |

INDEX TABLE A-continued

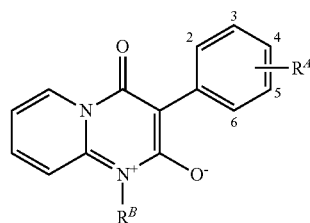

| Cmpd | $R^A$ | $R^B$ | m.p. (° C.) | AP+ (M + 1) |
|---|---|---|---|---|
| 200 | 2-F, 5-CF$_3$ | X-1 | | 456 |
| 201 | 2-F, 5-CF$_3$ | X-6 | | 434 |
| 202 | 3,5-diCl | X-1 | | 438 |
| 203 | 2-F, 5-Cl | X-1 | | 422 |
| 204 | — | X-11 | | 404 |
| 205 | 4-F | X-11 | | 422 |
| 206 | 2,4-diF | X-11 | | 440 |
| 207 | 3-CF$_3$ | X-11 | | 472 |
| 208 | 3-Br, 5-OCH$_3$ | X-1 | | 478 |
| 209 | 2-F, 5-OCH$_3$ | X-1 | | 418 |
| 210 | — | X-12 | | 384 |
| 211 | 4-F | X-12 | | 402 |
| 212 | 2,4-diF | X-12 | | 420 |
| 213 | 3-CF$_3$ | X-12 | | 452 |
| 214 | 3,5-bis(CF$_3$) | X-1 | | 506 |
| 215 | 3-Br, 5-CF$_3$ | CH$_2$CF$_3$ | 189-190 | |
| 216 | 2-F, 3-OCH$_3$ | X-1 | | 418 |
| 217 | 2-F, 5-OCF$_3$ | X-1 | | 472 |
| 218 | — | X-13 | | 370 |
| 219 | 4-F | X-13 | | 388 |
| 220 | 3,5-di(OCH$_3$) | X-5 | | 424 |
| 221 | 3,5-di(OCH$_3$) | CH$_2$CF$_3$ | | 381 |
| 223 | 2,4-di(OCH$_3$) | X-1 | | 430 |
| 225 | 2,4,5-triF | X-6 | 215-217 | |
| 226 | 4-CN | X-6 | | 373 |
| 227 | 3-OCH$_3$ | X-6 | | 378 |
| 228 | 2-F, 3-OCH$_3$ | CH$_2$CF$_3$ | | * |
| 229 | 3-F, 5-CF$_3$ | X-1 | | 456 |
| 230 | — | X-3 | | 350 |
| 231 | 4-F | X-4 | | 354 |
| 232 | 3-(3-pyridinyl) | X-5 | | 441 |
| 233 | 3-(6-Cl-3-pyridinyl) | X-5 | | 474 |
| 234 | 2-F, 5-(6-F-3-pyridinyl) | X-5 | | 459 |
| 235 | 3-(6-F-3-pyridinyl) | X-5 | | 477 |
| 236 | 2-F, 4-CN | CH$_2$CF$_3$ | | 364 |
| 237 | 4-F | CH$_2$CHFCF$_2$Cl | | 387 |
| 238 | 2,4-diF | CH$_2$CHFCF$_2$Cl | | 405 |
| 239 | 4-(6-Cl-3-pyridinyl) | X-5 | | 475 |
| 240 | 3-(6-Cl-3-pyridinyl) | X-1 | | 481 |
| 241 | 3-CF$_3$, 5-(6-F-3-pyridinyl) | X-5 | | 527 |
| 242 | 3-(6-Cl-3-pyridinyl), 4-F | X-5 | | 493 |
| 244 | 2-OCH$_3$, 5-CF$_3$ | X-5 | | 549 |
| 245 | 2-OCH$_3$, 5-Cl | X-5 | | 428 |
| 246 | 2-OCH$_3$ | X-6 | | 378 |
| 248 | 2,4,6-tri(CH$_3$) | X-5 | | 406 |
| 249 | 2,4,6-tri(CH$_3$) | X-1 | | 412 |
| 250 | 2-OCH$_3$, 5-(6-Cl-3-pyridinyl) | X-5 | | 505 |
| 252 | 3-(6-Cl-3-pyridinyl), 4-F | X-1 | | 499 |
| 253 | 3-(6-F-3-pyridinyl) | X-1 | | 465 |
| 254 | 3-CF$_3$, 5-(6-Cl-3-pyridinyl) | X-1 | | 549 |
| 255 | 3-CF$_3$, 5-(6-F-3-pyridinyl) | X-1 | | 533 |
| 256 | 2-Cl, 5-OCF$_3$ | X-6 | | 466 |
| 259 | 2-OCF$_3$ | X-6 | | 432 |
| 260 | 2-CF$_3$ | X-6 | | 416 |
| 261 | 2-OCF$_3$ | X-1 | | 454 |
| 262 | 2-CF$_3$ | X-1 | | 438 |
| 263 | 2-I | X-1 | | 496 |
| 264 | 3-I | X-1 | | 496 |
| 266 | 3-Br, 4-OCH$_3$ | X-1 | | 478 |
| 267 | 2-(6-Cl-3-pyridinyl) | X-1 | | 481 |
| 268 | 2-OCH$_3$, 5-Br | X-1 | | 478 |
| 269 | 3-(6-Cl-3-pyridinyl), 4-OCH$_3$ | X-1 | | 511 |
| 270 | 3-(6-Br-3-pyridinyl) | X-1 | | 525 |
| 271 | 3-(6-CF$_3$-3-pyridinyl) | X-1 | | 515 |
| 272 | 2,3,6-triF | X-1 | | 424 |

INDEX TABLE A-continued

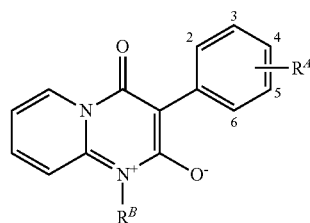

| Cmpd | $R^A$ | $R^B$ | m.p. (° C.) | AP+ (M + 1) |
|---|---|---|---|---|
| 273 | 2-F, 3-Cl, 5-CF$_3$ | X-1 | | 490 |
| 274 | 3-CF$_3$ | X-1 | | 438 |
| 275 | 2-F | X-2 | | 432 |
| 276 | 4-F | X-2 | | 432 |
| 277 | 3-OCF$_3$ | X-2 | | 498 |
| 278 | 3-(6-Cl-3-pyridinyl) | X-2 | | 525 |
| 279 | 3-Br, 5-CF$_3$ | X-2 | | 560 |
| 281 | 2-I | X-5 | | 490 |
| 282 | 3-OCF$_3$, 5-(6-Cl-3-pyridinyl) | X-1 | | 565 |
| 285 | 2-F, 3-Cl, 5-CF$_3$ | X-5 | | 484 |
| 287 | 3-OCH$_3$, 5-(6-Cl-3-pyridinyl) | X-1 | | 511 |
| 288 | 2,6-diF, 3-Cl | X-1 | | 440 |
| 289 | 2,3-diF, 6-OCH$_3$ | X-5 | | 430 |
| 290 | 2,3-diF, 6-OCH$_3$ | X-1 | | 436 |
| 291 | 3-OCF$_3$, 5-(6-CF$_3$-3-pyridinyl) | X-1 | | 599 |
| 292 | 3-CF$_3$, 5-(6-CF$_3$-3-pyridinyl) | X-1 | | 583 |
| 293 | 3-(6-CF$_3$-3-pyridinyl), 4-OCH$_3$ | X-1 | | 545 |
| 294 | 3-(6-CF$_3$-3-pyridinyl) | X-6 | | 493 |
| 295 | 3-(6-CF$_3$-3-pyridinyl) | X-5 | | 509 |
| 296 | 3-(6-CF$_3$-3-pyridinyl) | X-2 | | 559 |
| 297 | 3-Br, 5-OCF$_3$ | X-2 | | 576 |
| 298 | 2-F, 5-(6-CF$_3$-3-pyridinyl) | X-1 | | 533 |
| 299 | 2-F, 5-(6-CF$_3$-3-pyridinyl) | X-2 | | 577 |
| 300 | 2-OCH$_3$, 3,5-diF | X-5 | | 430 |
| 301 | 2,6-diF, 3-OCH$_3$ | X-5 | | 430 |
| 302 | 2-OCH$_3$, 3,5-diF | X-1 | | 436 |
| 303 | 2,6-diF, 3-OCH$_3$ | X-1 | | 436 |
| 304 | 2-F, 5-OCH$_3$ | X-5 | | 412 |
| 305 | 2-F, 5-OCH$_3$ | CH$_2$CF$_3$ | | 369 |
| 306 | 3,5-bis(6-CF$_3$-3-pyridinyl) | X-1 | | 660 |
| 307 | 3-OCF$_3$ | CH$_2$CF$_3$ | 140-141 | |
| 308 | 3-CF$_3$ | CH$_2$CF$_3$ | 178-179 | |
| 309 | 4-CF$_3$ | CH$_2$CF$_3$ | | 389 |
| 310 | 3,5-bis(CF$_3$) | CH$_2$CF$_3$ | | 457 |
| 311 | 3,5-diF | CH$_2$CF$_3$ | | 357 |
| 312 | 3,5-diF | CH$_2$CF$_3$ | | * |
| 313 | 3,5-diCl | CH$_2$CF$_3$ | | * |
| 314 | 3-Br, 5-OCH$_3$ | CH$_2$CF$_3$ | | 429 |
| 315 | 2-CF$_3$ | CH$_2$CF$_3$ | | 389 |
| 316 | 2-OCF$_3$ | CH$_2$CF$_3$ | | 405 |
| 317 | 4-OCF$_3$ | CH$_2$CF$_3$ | | 405 |
| 318 | 4-F | CH$_2$CF$_3$ | 205-206 | |
| 319 | 4-CN | CH$_2$CF$_3$ | | 346 |
| 320 | — | CH$_2$CH$_2$CHFCF$_2$Cl | | 383 |
| 321 | — | CH$_2$CH$_2$CF$_3$ | | * |
| 322 | 3-Cl | CH$_2$CF$_3$ | | * |
| 323 | 3-Br | CH$_2$CF$_3$ | 233-234 | |
| 324 | 3,4-di(OCH$_3$) | CH$_2$CF$_3$ | | 381 |
| 325 | 2-F, 3-CH$_3$, 5-Cl | CH$_2$CF$_3$ | | 387 |
| 326 | 2-OCH$_3$, 5-Cl | CH$_2$CF$_3$ | | * |
| 327 | 2,3-diF | CH$_2$CF$_3$ | | 357 |
| 328 | 2-F, 4-Cl, 5-OCH$_3$ | CH$_2$CF$_3$ | | 403 |
| 329 | 3-CF$_3$, 4-OCH$_3$ | CH$_2$CF$_3$ | | 419 |
| 330 | 2-F, 5-OCH$_3$ | CH$_2$CF$_3$ | | * |
| 331 | 2-OCH$_2$CH$_3$, 5-CF$_3$ | CH$_2$CF$_3$ | | * |
| 332 | 2-F, 3-CF$_3$ | CH$_2$CF$_3$ | | 407 |
| 333 | 3-OCF$_3$ | CH$_2$CH$_2$CHFCF$_2$Cl | | * |
| 334 | 4-CN | CH$_2$CH$_2$CHFCF$_2$Cl | | * |
| 335 | 2,4-diF | CH$_2$CF$_3$ | | * |
| 336 | 2,5-diF | CH$_2$CF$_3$ | | * |
| 337 | 3,4-diF | CH$_2$CF$_3$ | 118-119 | |
| 338 | 3-Cl, 4-F | CH$_2$CF$_3$ | | 373 |
| 339 | 4-CH$_2$CH$_2$CH$_2$CH$_3$ | CH$_2$CF$_3$ | | 377 |
| 340 | 3-CF$_3$, 4-F | CH$_2$CF$_3$ | | 407 |
| 341 | 3-Br, 4-F | CH$_2$CF$_3$ | 213-214 | |

INDEX TABLE A-continued

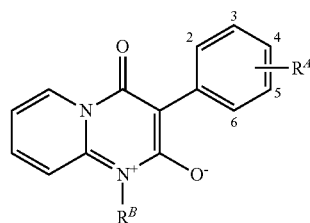

| Cmpd | $R^A$ | $R^B$ | m.p. (°C.) | AP+ (M + 1) |
|---|---|---|---|---|
| 342 | 4-F | $CH_2CH_2CHFCF_2Cl$ | | * |
| 343 | 3-F, 4-CN | $CH_2CF_3$ | | 338 |
| 344 | 2-Cl, 4-F | $CH_2CF_3$ | | 373 |
| 345 | 2-OCH$_3$, 4-F | $CH_2CF_3$ | | 368 |
| 346 | 2-OCH$_3$, 5-CF$_3$ | $CH_2CF_3$ | | 419 |
| 347 | 3-F | $CH_2CF_3$ | | 339 |
| 348 | 4-Cl | $CH_2CF_3$ | 226-227 | |
| 349 | 4-CH$_3$ | $CH_2CF_3$ | | 335 |
| 350 | 4-OCH$_3$ | $CH_2CF_3$ | | 351 |
| 351 | 3-CH$_3$ | $CH_2CF_3$ | | 335 |
| 352 | 3-OCH$_3$ | $CH_2CF_3$ | 124-125 | |
| 353 | 4-Br | $CH_2CF_3$ | | 399 |
| 354 | 4-F | $CH_2CF_3$ | | 353 |
| 355 | 4-F | $CH_2CF_2CF_3$ | | * |
| 356 | — | $CH_2CF_2CF_3$ | | * |
| 357 | 3-OCF$_3$ | $CH_2CF_2CF_3$ | | * |
| 358 | 3-CN, 4-F | $CH_2CF_3$ | | * |
| 359 | 2,4-diF | $CH_2CF_2CF_3$ | | * |
| 360 | 2,4-diF | $CH_2CH_2CHFCF_2Cl$ | | * |
| 361 | 3-CF$_3$ | $CH_2CF_2CF_3$ | | 439 |
| 362 | 3-CF$_3$ | $CH_2CH_2CHFCF_2Cl$ | | 451 |
| 363 | 2,4-diCl | $CH_2CF_3$ | | * |
| 364 | 2,4-diCl | $CH_2CH_2CHFCF_2Cl$ | | 451 |
| 365 | 2,4-diCl | $CH_2CF_2CF_3$ | | 439 |
| 366 | 2-OCH$_3$ | $CH_2CF_3$ | | * |
| 367 | 2-CH$_3$ | $CH_2CF_3$ | | 335 |
| 368 | 2-Br | $CH_2CF_3$ | | 399 |
| 369 | 2-Cl | $CH_2CF_3$ | | 355 |
| 370 | 3-CH$_2$CH$_2$CH$_3$, 4-I | $CH_2CF_3$ | | 503 |
| 371 | 3-CH$_2$CH$_2$CH$_3$ | $CH_2CF_3$ | | 377 |
| 372 | 2,4,6-triCl | $CH_2CF_3$ | | 423 |
| 373 | 2,4,6-triCl | $CH_2CH_2CHFCF_2Cl$ | | 485 |
| 374 | 2-F, 4-Cl | $CH_2CF_3$ | | * |
| 375 | 2,6-diCl | $CH_2CF_3$ | | 389 |
| 376 | 2,4-di(CH$_3$) | $CH_2CF_3$ | | 349 |
| 377 | 2-F | $CH_2CF_3$ | 211-212 | |
| 378 | 3-CN | $CH_2CF_3$ | | 346 |
| 379 | 2-CH$_2$CH$_2$CH$_3$ | $CH_2CF_3$ | | 377 |
| 380 | 3-CH$_3$, 4-F | $CH_2CF_3$ | 239-240 | |
| 381 | 2,4,6-triCl | $CH_2CF_2CF_3$ | | 473 |
| 382 | 4-F | $CH_2CH_2CH_2CF_2Cl$ | | 383 |
| 383 | 2,4-diF | $CH_2CH_2CH_2CF_2Cl$ | | 401 |
| 385 | 3-OCF$_3$ | $CH_2CH_2CH_2CF_2Cl$ | | 449 |
| 386 | 2,3,4-triF | $CH_2CF_3$ | | 375 |
| 387 | 2,4,5-triF | $CH_2CF_3$ | | 375 |
| 388 | 2,4,6-triF | $CH_2CF_3$ | | 375 |
| 389 | 3,4,5-triF | $CH_2CF_3$ | | 375 |
| 390 | 2-CF$_3$, 4-F | $CH_2CF_3$ | | 407 |
| 391 | 2-Cl, 5-OCF$_3$ | $CH_2CF_3$ | | 439 |
| 392 | 2-CN | $CH_2CF_3$ | | 346 |
| 393 | — | X-5 | | * |
| 394 | 2-F, 4-Br | $CH_2CF_3$ | | 417 |
| 395 | 2,4-diF | X-5 | | * |
| 396 | 3-OCF$_3$ | X-5 | | * |
| 397 | 2-Br, 4,6-diF | $CH_2CF_3$ | | 435 |
| 399 | 4-F | X-5 | | * |
| 400 | 3-CN, 4-F | $CH_2CH_2CHFCF_2Cl$ | | 426 |
| 401 | 3-OCF$_3$ | X-14 | | 414 |
| 402 | 4-F | X-14 | | 348 |
| 403 | 2,4-diF | X-14 | | 365 |
| 404 | — | X-14 | | 330 |
| 405 | 3-CF$_3$, 4-F | X-5 | | * |
| 406 | 2-Cl, 4-F | X-5 | | * |
| 407 | 2-CF$_3$, 4-F | X-5 | | 450 |
| 408 | 3-Br, 4-F | X-5 | | * |

INDEX TABLE A-continued

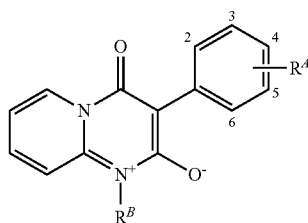

| Cmpd | $R^A$ | $R^B$ | m.p. (°C.) | AP+ (M + 1) |
|---|---|---|---|---|
| 409 | 2-Cl, 5-OCF$_3$ | X-5 | | * |
| 410 | 2-F, 4-Br | X-5 | | * |
| 411 | 2-Br, 4-F | X-5 | | * |
| 414 | 2,4-diCl | X-5 | | * |
| 415 | 4-Br | X-5 | | * |
| 416 | 4-CN | X-5 | | * |
| 417 | 2-CH$_3$, 4-Br | X-5 | | * |
| 418 | — | X-15 | | * |
| 419 | 3-CF$_3$ | X-5 | | * |
| 420 | 2-CH$_3$, 4-CN | X-5 | | * |
| 421 | 4-Cl | X-5 | | * |
| 422 | 3,5-diCl | X-5 | | * |
| 423 | 2-Cl | X-5 | | 398 |
| 424 | 2-CH$_3$ | X-5 | | 378 |
| 425 | 2-OCF$_3$ | X-5 | | 448 |
| 426 | 2-CN | X-5 | | 389 |
| 427 | 2-OCH$_3$ | X-5 | | 394 |
| 429 | 3-Cl | X-5 | | * |
| 430 | 3-Br | X-5 | | * |
| 431 | 4-OCH$_3$ | X-5 | | * |
| 432 | 4-OCF$_3$ | X-5 | | * |
| 433 | 3,4-diF | X-5 | | * |
| 434 | 2,3,4-triF | X-5 | | * |
| 435 | 2,4,5-triF | X-5 | | * |
| 436 | 3-Br, 5-OCF$_3$ | X-5 | | * |
| 437 | 3-OCH$_3$, 4-F | X-5 | | * |
| 438 | 2-F, 5-OCF$_3$ | X-5 | | * |
| 439 | — | X-16 | | 330 |
| 440 | — | X-17 | | 330 |
| 441 | 3-CN | X-5 | | * |
| 442 | 4-F | X-16 | | * |
| 444 | 3-Br, 5-OCF$_3$ | X-14 | | * |
| 445 | 2-CH$_3$, 4-F | CH$_2$CF$_3$ | | * |
| 446 | 4-F | X-18 | | * |
| 447 | 3-OCF$_3$ | X-18 | | * |
| 448 | 2-CH$_3$, 4-F | X-5 | | * |
| 449 | 2,4-diF | X-18 | | 434 |
| 450 | — | X-18 | | * |
| 451 | 3-F | X-5 | | * |
| 452 | 4-CF$_3$ | X-5 | | * |
| 453 | 3,5-bis(CF$_3$) | X-5 | | 500 |
| 454 | 3-OCH$_2$CF$_3$ | CH$_2$CF$_3$ | 162-163 | |
| 455 | 4-CH$_3$ | X-5 | | * |
| 456 | 4-OCHF$_2$ | X-5 | | * |
| 457 | 2,4-di(CH$_3$) | X-5 | | 424 |
| 458 | 2-F, 3-CF$_3$ | X-5 | | * |
| 459 | 4-OCH$_3$ | X-18 | | * |
| 460 | 2-F | X-18 | | 416 |
| 461 | 2-F, 4-OCH$_3$ | X-5 | | * |
| 462 | 3-CF$_3$, 4-OCH$_3$ | X-5 | | 462 |
| 463 | 2,3-diF, 4-OCH$_3$ | X-5 | | 430 |
| 464 | 3-F, 4-OCH$_3$ | X-5 | | * |
| 467 | 3-Br, 5-CF$_3$ | X-5 | | * |
| 469 | 2-F, 4-CF$_3$ | X-5 | | * |
| 470 | 3-Cl, 5-CF$_3$ | X-5 | | * |
| 472 | 4-F | X-19 | | 416 |
| 474 | 3-OCF$_3$ | X-19 | | * |
| 476 | 2-F, 5-CF$_3$ | X-5 | | * |
| 479 | — | X-1 | 233-235 | |
| 480 | 4-F | X-1 | | * |
| 481 | 2,4-diF | X-1 | | * |
| 482 | — | X-6 | 241-243 | |
| 483 | 4-F | X-6 | 211-213 | |
| 487 | 2-F, 4-CN | X-5 | | * |
| 491 | 3-CF$_3$ | X-1 | 152-153 | |

INDEX TABLE A-continued

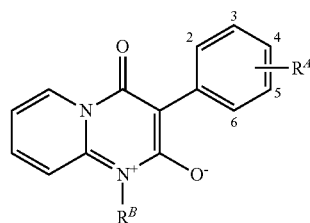

| Cmpd | R$^A$ | R$^B$ | m.p. (° C.) | AP+ (M + 1) |
|---|---|---|---|---|
| 492 | 3-Cl | X-1 | 235-237 | |
| 493 | 4-OCHF$_2$ | X-1 | 182-183 | |
| 494 | 4-OCH$_3$ | X-1 | 215-217 | |
| 495 | — | X-9 | | 344 |
| 496 | 4-F | X-9 | | 362 |
| 497 | 2,4-diF | X-9 | | 380 |
| 498 | 3-Br | X-1 | 224-226 | |
| 499 | 2-F, 4-CN | X-1 | | 413 |
| 500 | — | X-10 | | 408 |
| 501 | 4-F | X-10 | | 426 |
| 502 | 3-CF$_3$, 4-F | X-1 | | 455 |
| 503 | 2-Cl, 4-F | X-1 | | 422 |
| 504 | 4-CN | X-1 | | 395 |
| 505 | 3,5-diF | X-5 | | 400 |
| 506 | 3-F | X-1 | | 388 |
| 507 | 4-CF$_3$ | X-1 | | 438 |
| 508 | 4-OCF$_3$ | X-1 | | 454 |
| 509 | 4-CH$_3$ | X-1 | | 384 |
| 510 | 2-CN | X-1 | | 395 |
| 511 | 3,4-diF | X-1 | | 406 |
| 512 | 3-OCH$_3$, 4-F | X-1 | | * |
| 513 | 2-Br, 4-F | X-1 | | 466 |
| 514 | 2-CH$_3$, 4-CN | X-1 | | 409 |
| 515 | 2,4-diCl | X-1 | | 438 |
| 516 | 2-Cl, 5-OCF$_3$ | X-1 | | 488 |
| 517 | 2,3,4-triF | X-1 | 196-198 | 424 |
| 518 | 2,4,5-triF | X-1 | 195-197 | 424 |
| 519 | 2-F, 5-Br | X-1 | | 466 |
| 522 | 3,5-diF | X-1 | | 406 |
| 523 | 3-F, 4-OCH$_3$ | X-1 | 205-207 | 418 |
| 524 | 2,4,6-triF | X-1 | | * |
| 525 | 3-OCF$_3$ | X-10 | 153-155 | 504 |
| 526 | 3-OCH$_3$ | X-10 | | 438 |
| 527 | — | X-21 | 216-220 | |
| 528 | — | X-22 | 200-202 | |
| 529 | 3-(3-chloro-4-(trifluoromethyl)phenyl) | X-1 | | 548 |
| 530 | 3-CH$_3$, 5-CF$_3$ | X-1 | | 452 |
| 531 | 3-Cl, 5-CH$_3$ | X-1 | | 418 |
| 532 | 3-CH$_3$ | X-8 | | 345 |
| 533 | 3-CH$_3$ | X-7 | | 359 |
| 534 | 3,5-di(CH$_2$CH$_3$) | X-1 | | 426 |
| 535 | 2-CH$_3$, 5-Cl | X-1 | | 418 |
| 536 | 2-OCH$_3$, 5-CH$_3$ | X-1 | | 414 |
| 537 | 2-F, 5-CH$_3$ | X-1 | | 402 |
| 538 | 3-F, 5-(4-chlorophenyl) | X-1 | | 498 |
| 539 | — | X-23 | 290-294 | |
| 540 | 3-C(CH$_3$)$_3$ | X-1 | | 426 |
| 541 | 3-(2-fluoro-4-chlorophenyl) | X-1 | | 498 |
| 542 | 3-(2-chloro-4-(trifluoromethyl)phenyl) | X-1 | | 548 |
| 543 | 3-(4-bromophenyl) | X-1 | | 524 |
| 544 | 3-(3-methylphenyl) | X-1 | | 460 |
| 545 | — | X-24 | 290-294 | |
| 546 | — | X-25 | 319-323 | |
| 547 | 3-CF$_3$, 4-F | X-8 | | 417 |
| 548 | 2-F, 3-CH$_3$ | X-1 | | 402 |
| 549 | 2-OCH$_3$, 3-CH$_3$ | X-1 | | 414 |
| 550 | 3-(2-methyl-4-chlorophenyl) | X-1 | | 494 |
| 551 | 3-(3-chloro-4-fluorophenyl) | X-1 | | 498 |
| 552 | 3-CH$_2$CH$_2$CH$_3$ | X-1 | | 412 |
| 553 | 3,5-di(CH$_3$) | X-1 | | 398 |
| 554 | 3-(2-fluoro-4-chlorophenyl) | X-8 | | 459 |
| 555 | — | X-26 | 292-294 | |
| 556 | 2-F | X-21 | 186-191 | |
| 557 | 2-F | X-22 | 223-227 | |
| 558 | 2-F | X-24 | 197-201 | |

INDEX TABLE A-continued

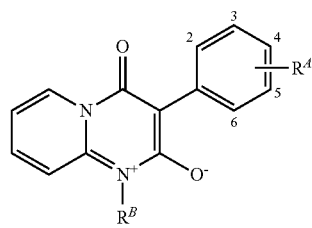

| Cmpd | $R^A$ | $R^B$ | m.p. (° C.) | AP+ (M + 1) |
|---|---|---|---|---|
| 559 | 2-F | X-23 | 284-286 | |
| 560 | 2-F | X-25 | 310-312 | |
| 561 | 2-F | X-26 | 281-284 | |
| 562 | 3-(4-chlorophenyl), 4-F | X-1 | | 498 |
| 563 | 3-(2-fluoro-4-chlorophenyl), 4-F | X-1 | | 516 |
| 564 | 2-OCH₃, 5-(4-chlorophenyl) | X-1 | | 510 |
| 565 | 2-OCH₃, 5-(2-fluoro-4-chlorophenyl) | X-1 | | 528 |
| 566 | 2-Cl | X-8 | | 365 |
| 567 | 2-F, 5-(2-fluoro-4-chlorophenyl) | X-1 | | 516 |
| 568 | 2-F, 5-(4-chlorophenyl) | X-1 | | 498 |
| 569 | 3-CF₃ | X-27 | | 433 |
| 570 | 3-Br | X-27 | | 444 |
| 571 | 3-OCF₃ | X-27 | | 449 |
| 572 | 3-OCF₃, 4-F | X-1 | | 544 |
| 573 | 3-Br, 4-F | X-1 | | 466 |
| 574 | 3-CN, 5-CF₃ | X-1 | | 463 |
| 575 | 3-Br, 5-CH₃ | X-1 | | 462 |
| 576 | 3-(2-fluoro-5-(trifluoromethyl)phenyl) | X-1 | | 532 |
| 577 | 3-(2-fluoro-4-bromophenyl) | X-1 | | 542 |
| 578 | 3-OCF₃ | X-21 | 83-87 | |
| 579 | 3-OCF₃ | X-22 | 124-126 | |
| 580 | 3-OCF₃ | X-24 | 186-189 | |
| 581 | 3-OCF₃ | X-23 | 191-195 | |
| 582 | 3-OCF₃ | X-25 | 191-195 | |
| 583 | 3-(2-fluoro-5-(trifluoromethoxy)phenyl) | X-1 | | 548 |
| 584 | 3-CN, 4-F | X-1 | | 414 |
| 585 | 3-(2-fluoro-4-chlorophenyl), 4-OCH₃ | X-1 | | 528 |
| 586 | 3-(4-chlorophenyl), 4-OCH₃ | X-1 | | 510 |
| 587 | 3-CH(CH₃)₂ | X-1 | | 412 |
| 588 | 3-CH₃, 5-(6-(trifluoromethyl)-3-pyridinyl) | X-1 | | 529 |
| 589 | 3-(2,4-difluorophenyl) | X-1 | | 482 |
| 592 | 2-OCH₃, 3-(2-chloro-4-fluorophenyl) | X-1 | | 528 |
| 593 | 3-(2-chloro-4-fluorophenyl), 4-F | X-1 | | 516 |
| 594 | 3-(2-fluoro-4-chlorophenyl) | X-1 | | 498 |
| 595 | 3-Cl, 5-CF₃ | X-8 | | 433 |
| 598 | 3-(4-chlorophenyl) | X-5 | | 474 |
| 599 | 3-(4-chlorophenyl) | X-6 | | 458 |
| 600 | 3-Cl, 5-(4-chlorophenyl) | X-1 | | 514 |
| 601 | 3-Cl, 3-(2,4-dichlorophenyl) | X-1 | | 548 |
| 603 | 3-F, 5-(4-(trifluoromethyl)phenyl) | X-1 | | 532 |
| 604 | 3-Cl, 5-(4-(trifluoromethyl)phenyl) | X-1 | | 548 |
| 605 | 3-CN | X-1 | | 395 |
| 606 | 3-CN, 5-OCH₃ | X-1 | | 425 |
| 607 | 3-phenyl | X-1 | | 446 |
| 608 | 2-F, 5-(4-fluorophenyl) | X-1 | | 482 |
| 609 | 3-(3,5-difluorophenyl) | X-1 | | 482 |
| 610 | 3-Cl, 5-(6-(trifluoromethyl)-3-pyridinyl) | X-1 | | 549 |
| 612 | 3-(3-chloro-5-(trifluoromethyl)phenyl) | X-1 | | 548 |
| 613 | 3-(2-chloro-4-(trifluoromethyl)phenyl), 4-CH₃ | X-1 | | 562 |
| 614 | 3-F, 5-(6-(trifluoromethyl)-3-pyridinyl) | X-1 | | 533 |
| 615 | 3-(2-(trifluoromethyl)-4-chlorophenyl) | X-1 | | 562 |
| 616 | 3-CF₃, 5-(4-chlorophenyl) | X-1 | | 548 |
| 618 | 3-(2-chloro-4-(trifluoromethyl)phenyl), 4-F | X-1 | | 566 |
| 619 | 3-(6-(trifluoromethyl)-3-pyridinyl), 4-F | X-1 | | 533 |
| 620 | 3-(2,4-dichlorophenyl), 4-F | X-1 | | 532 |
| 621 | 3-Cl, 5-CN | X-1 | | 429 |
| 622 | 3-F, 5-CN | X-1 | | 413 |
| 623 | 3-CH₃, 5-CN | X-1 | | 409 |
| 624 | 3-Br, 5-CN | X-1 | | 473 |
| 625 | 2-F, 5-(4-(trifluoromethyl)phenyl) | X-1 | | 532 |
| 627 | 2-Cl, 5-(4-(trifluoromethyl)phenyl) | X-1 | | 548 |
| 628 | 2-Cl, 5-(6-(trifluoromethyl)-3-pyridinyl) | X-1 | | 549 |
| 629 | 3-(4-(trifluoromethyl)phenyl), 4-Cl | X-1 | | 548 |
| 630 | 3-(6-(trifluoromethyl)-3-pyridinyl), 4-Cl | X-1 | | 549 |
| 631 | 3-(4,6-dichloro-3-pyridinyl) | X-1 | | 515 |

INDEX TABLE A-continued

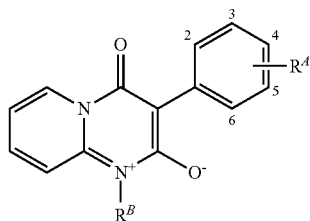

| Cmpd | $R^A$ | $R^B$ | m.p. (° C.) | AP+ (M + 1) |
|---|---|---|---|---|
| 632 | 3-(4-(trifluoromethyl)phenyl), 4-CH$_3$ | X-1 | | 528 |
| 633 | 3-(6-(trifluoromethyl)-3-pyridinyl), 4-CH$_3$ | X-1 | | 529 |
| 635 | 2-CH$_3$, 5-(6-(trifluoromethyl)-3-pyridinyl) | X-1 | | 529 |
| 636 | 2-CH$_3$, 5-(2-chloro-4-(trifluoromethyl)phenyl) | X-1 | | 562 |
| 637 | 2-CH$_3$, 5-(4-(trifluoromethyl)phenyl) | X-1 | | 528 |
| 638 | 3-(2-chloro-4-(trifluoromethyl)phenyl), 4-OCH$_3$ | X-1 | | 578 |
| 639 | 2-OCH$_3$, 5-(4-(trifluoromethyl)phenyl) | X-1 | | 544 |
| 640 | 2-OCH$_3$, 5-(2-chloro-4-(trifluoromethyl)phenyl) | X-1 | | 578 |
| 643 | 3-(2-chloro-4-(trifluoromethyl)phenyl), 4-CN | X-1 | | 573 |
| 644 | 3-(4-(trifluoromethyl)phenyl), 4-OCH$_3$ | X-1 | | 544 |
| 645 | 3-(3-chloro-5-(trifluoromethyl)phenyl), 4-F | X-1 | | 566 |
| 646 | 3,5-diCl | X-8 | | 399 |
| 647 | 3,5-diCl, 4-F | X-8 | | 417 |
| 648 | 3,5-diCl, 4-F | X-1 | | 456 |
| 649 | 3,5-diCl, 4-F | X-5 | | 450 |
| 650 | 3-(2-fluoro-4-(trifluoromethyl)phenyl), 4-OCH$_3$ | X-1 | | 562 |
| 651 | 3-(3-bromo-5-fluorophenyl) | X-1 | | 542 |
| 652 | 2-Cl, 5-Br | X-1 | | 482 |
| 653 | 2-F, 5-(2-chloro-4-(trifluoromethyl)phenyl) | X-1 | | 566 |
| 654 | 3-(2-chloro-4-(trifluoromethyl)phenyl), 4-Cl | X-1 | | 582 |
| 655 | 3-(2-fluoro-4-chlorophenyl), 4-CH$_3$ | X-1 | | 512 |
| 656 | 3-(3-chloro-5-fluorophenyl) | X-1 | | 498 |
| 657 | 3-CH$_3$, 5-(2-chloro-4-(trifluoromethyl)phenyl) | X-1 | | 562 |
| 658 | 3-Br, 4-CH$_3$ | X-1 | | 462 |
| 659 | 3-(2,6-dichloro-3-pyridinyl), 4-F | X-1 | | 533 |
| 660 | 2-F, 5-(4,6-dichloro-3-pyridinyl) | X-1 | | 533 |
| 661 | 2-F, 5-(2-bromo-5-chloro-4-pyridinyl) | X-1 | | 559 |
| 665 | 3-(2-fluoro-6-chloro-3-pyridinyl) | X-1 | | 499 |
| 666 | 3-(2-fluoro-4-(trifluoromethyl)phenyl), 4-F | X-1 | | 550 |
| 667 | 3-(2-chloro-5-(trifluoromethyl)phenyl) | X-1 | | 548 |
| 668 | 3-(2-(trifluoromethyl)-4-chlorophenyl), 4-Cl | X-1 | | 566 |
| 669 | 3-(2-fluoro-4-chlorophenyl), 4-Cl | X-1 | | 532 |
| 670 | 3-(2,4-bis(trifluoromethyl)phenyl) | X-1 | | 582 |
| 671 | 3-CH$_3$, 5-(2-(trifluoromethyl)-4-chlorophenyl) | X-1 | | 578 |
| 672 | 3-(2-fluoro-4-chlorophenyl), 4-F | X-1 | | 512 |
| 673 | 3-(2-fluoro-4-(trifluoromethyl)phenyl), 4-CH$_3$ | X-1 | | 546 |
| 674 | 3-(3-fluoro-4-chlorophenyl), 4-OCH$_3$ | X-1 | | 528 |
| 675 | 3-(3-fluoro-4-chlorophenyl), 4-F | X-1 | | 516 |
| 676 | 3-(3-fluoro-4-(trifluoromethyl)phenyl), 4-F | X-1 | | 566 |
| 677 | 3-(2,6-dichloro-3-pyridinyl), 4-OCH$_3$ | X-1 | | 545 |
| 680 | 3-Cl, 5-F | X-1 | | 422 |
| 681 | 3-(3-(trifluoromethyl)-4-chlorophenyl) | X-1 | | 548 |
| 682 | 3-Cl, 5-(2-chloro-4-(trifluoromethyl)phenyl) | X-1 | | 582 |
| 683 | 3-Cl, 5-(2-fluoro-4-chlorophenyl) | X-1 | | 532 |
| 684 | 3-Cl, 5-OCH$_3$ | X-1 | | 434 |
| 685 | 3-CH$_3$, 4-F | X-1 | | 402 |
| 687 | 3-Cl, 5-(2,6-dichloro-3-pyridinyl) | X-1 | | 549 |
| 688 | 3-Cl, 5-(2-fluoro-4-(trifluoromethyl)phenyl) | X-1 | | 566 |
| 689 | 3-(2-(trifluoromethyl)-4-chlorophenyl), 4-CH$_3$ | X-1 | | 562 |
| 690 | 3-CF$_3$, 5-(2-chloro-4-(trifluoromethyl)phenyl) | X-1 | | 616 |
| 691 | 4-(2-chloro-4-(trifluoromethyl)phenyl) | X-1 | | 548 |
| 692 | 4-I | X-1 | | 496 |
| 693 | 4-(2-chloro-4-fluorophenyl) | X-1 | | 498 |
| 694 | 4-(3-chloro-5-(trifluoromethyl)phenyl) | X-1 | | 548 |
| 698 | 4-(3-chloro-4-(trifluoromethyl)phenyl) | X-1 | | 548 |
| 699 | 2-F, 5-(2-fluoro-4-(trifluoromethyl)phenyl) | X-1 | | 550 |
| 700 | 2-OCH$_3$, 5-(2-fluoro-4-(trifluoromethyl)phenyl) | X-1 | | 562 |
| 701 | 2-(2-chloro-4-(trifluoromethyl)phenyl) | X-1 | | 548 |
| 702 | 3-F, 5-OCH$_3$ | X-1 | | 418 |
| 703 | 3-Cl, 5-I | X-1 | | 530 |
| 704 | 3-OCH$_3$, 5-CF$_3$ | X-1 | | 468 |
| 705 | 4-(2-fluorophenyl) | X-1 | | 464 |
| 706 | 4-(3-fluorophenyl) | X-1 | | 464 |
| 707 | 4-(4-fluorophenyl) | X-1 | | 464 |
| 708 | 3-(2-chloro-5-(trifluoromethyl)phenyl), 4-F | X-1 | | 566 |

INDEX TABLE A-continued

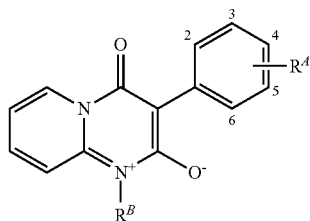

| Cmpd | R$^A$ | R$^B$ | m.p. (° C.) | AP+ (M + 1) |
|---|---|---|---|---|
| 709 | 2-(2-chloro-4-fluorophenyl) | X-1 | | 498 |
| 710 | 3-(2-chloro-5-(trifluoromethyl)phenyl), 4-CH$_3$ | X-1 | | 562 |
| 711 | 3-(2-chloro-5-(trifluoromethyl)phenyl), 4-OCH$_3$ | X-1 | | 578 |
| 712 | 2-F, 5-I | X-1 | | 514 |
| 713 | 2-F, 5-(2-chloro-5-(trifluoromethyl)phenyl) | X-1 | | 566 |
| 714 | 3-F, 5-(2-chloro-4-(trifluoromethyl)phenyl) | X-1 | | 566 |
| 716 | 3-F, 5-(2-chloro-5-(trifluoromethyl)phenyl) | X-1 | | 566 |
| 718 | 3-F, 5-(2-fluoro-4-chlorophenyl) | X-1 | | 516 |
| 719 | 3-(2,4-bis(trifluoromethyl)phenyl, 4-F | X-1 | | 600 |
| 724 | 3-CN, 5-(2-fluoro-4-bromophenyl) | X-1 | | 567 |
| 725 | 3-(2-fluoro-5-(trifluoromethyl)phenyl), 4-OCH$_3$ | X-1 | | 562 |
| 726 | 3-OCH$_3$, 5-(2-chloro-4-(trifluoromethyl)phenyl) | X-1 | | 550 |
| 727 | 3-(2-fluoro-5-(trifluoromethyl)phenyl), 4-F | X-1 | | 578 |
| 728 | 4-(2-chlorophenyl) | X-1 | | 480 |
| 729 | 4-(3-chlorophenyl) | X-1 | | 480 |
| 730 | 4-(4-chlorophenyl) | X-1 | | 480 |
| 731 | 4-phenyl | X-1 | | 446 |
| 732 | 2-OCH$_3$, 5-CN | X-1 | | 425 |
| 733 | 3-Cl, 5-(2-fluoro-6-chloro-3-pyridinyl) | X-1 | | 533 |
| 734 | 3-Cl, 5-(4,6-dichloro-3-pyridinyl) | X-1 | | 549 |
| 735 | 3-(2-(trifluoromethyl)-4-fluorophenyl) | X-1 | | 532 |
| 737 | 3-CN, 5-(2-chloro-4-(trifluoromethyl)phenyl) | X-1 | | 573 |
| 738 | 3-(2-chloro-6-(trifluoromethyl)-3-pyridinyl) | X-1 | | 549 |
| 739 | 3-Cl, 5-(2-fluoro-5-(trifluoromethyl)phenyl) | X-1 | | 566 |
| 740 | 3-Cl, 4-Br | X-1 | | 484 |
| 741 | 3-CF$_3$, 4-Br | X-1 | | 517 |
| 742 | 2-F, 3-Cl, 4-Br | X-1 | | 501 |
| 743 | 3-(2,6-dichloro-3-pyridinyl), 4-Cl | X-1 | | 549 |
| 744 | 3-(2-fluoro-5-(trifluoromethyl)phenyl), 4-CH$_3$ | X-1 | | 546 |
| 745 | 3-(2,4-bis(trifluoromethyl)phenyl), 4-CH$_3$ | X-1 | | 596 |
| 746 | 3-F, 5-(2-fluoro-4-(trifluoromethyl)phenyl) | X-1 | | 550 |
| 747 | 3-F, 5-(2,6-dichloro-3-pyridinyl) | X-1 | | 533 |
| 748 | 3-(2,4-bis(trifluoromethyl)phenyl), 4-OCH$_3$ | X-1 | | 612 |
| 749 | 3-OCH$_3$, 5-(2-fluoro-4-(trifluoromethyl)phenyl) | X-1 | | 562 |
| 750 | 3-OCH$_3$, 5-(2-fluoro-4-chlorophenyl) | X-1 | | 528 |
| 751 | 3-CN, 5-(2-fluoro-4-chlorophenyl) | X-1 | | 523 |
| 900 | 3-(6-methoxy-3-pyridinyl) | X-5 | | 471 |
| 901 | 3-(3-cyano-4-methoxyphenyl) | X-1 | | 515 |
| 902 | 3-(6-methoxy-3-pyridinyl) | X-1 | | 477 |
| 903 | 3-(4-(trifluoromethoxy)phenyl) | X-1 | | 530 |
| 904 | 3-(6-cyano-3-pyridinyl) | X-1 | | 472 |
| 905 | 3-(3-(trifluoromethoxy)phenyl) | X-1 | | 530 |
| 906 | 3-(3-(trifluoromethoxy)phenyl) | X-5 | | 524 |
| 907 | 3-(4-methoxyphenyl) | X-1 | | 476 |
| 908 | 3-OCF$_3$, 5-(4-(trifluoromethoxy)phenyl) | X-1 | | 614 |
| 909 | 3-(4-cyanophenyl) | X-1 | | 471 |
| 910 | 3-(3-cyanophenyl) | X-1 | | 471 |
| 911 | 3-(2-methylphenyl) | X-1 | | 460 |
| 912 | 3-(2-methyl-4-(trifluoromethyl)phenyl) | X-1 | | 528 |
| 913 | 3-CF$_3$, 5-(2-methyl-4-chlorophenyl) | X-1 | | 562 |
| 915 | 3-(2-methyl-4-(trifluoromethyl)phenyl), 4-F | X-1 | | 546 |
| 916 | 3-(2-methyl-4-chlorophenyl), 4-F | X-1 | | 513 |
| 917 | 3-(2,4-dimethylphenyl) | X-1 | | 474 |
| 918 | 3-(2-methyl-4-(trifluoromethyl)phenyl), 4-OCH$_3$ | X-1 | | 558 |
| 919 | 3-(2-methyl-4-chlorophenyl), 4-OCH$_3$ | X-1 | | 524 |
| 920 | 3-(2-fluoro-5-(trifluoromethoxy)phenyl), 4-F | X-1 | | 566 |
| 921 | 3-(2-fluoro-5-(trifluoromethoxy)phenyl), 4-OCH$_3$ | X-1 | | 578 |
| 922 | 3-(2-fluoro-5-(trifluoromethoxy)phenyl), 4-CH$_3$ | X-1 | | 562 |
| 923 | 3-Cl, 5-(2-fluoro-5-(trifluoromethoxy)phenyl) | X-1 | | 582 |
| 924 | 3-Cl, 5-(2-methyl-4-(trifluoromethyl)phenyl) | X-1 | | 562 |
| 925 | 2-F, 5-(2-methyl-4-(trifluoromethyl)phenyl) | X-1 | | 546 |
| 926 | 3-F, 5-(2-methyl-4-(trifluoromethyl)phenyl) | X-1 | | 546 |
| 927 | 3-(3-cyano-4-chlorophenyl) | X-1 | | 505 |
| 928 | 3-(2-fluoro-4-cyanophenyl) | X-1 | | 489 |
| 929 | 3-(2-methyl-4-(trifluoromethyl)phenyl), 4-CH$_3$ | X-1 | | 542 |

INDEX TABLE A-continued

| Cmpd | R^A | R^B | m.p. (°C.) | AP+ (M+1) |
|---|---|---|---|---|
| 930 | 3-(2-methyl-4-(trifluoromethyl)phenyl), 4-Cl | X-1 | | 562 |
| 931 | 3-F, 5-(2-fluoro-5-(trifluoromethyl)phenyl) | X-1 | | 550 |
| 932 | 3-(2-(trifluoromethyl)-4-fluorophenyl), 4-F | X-1 | | 550 |
| 933 | 3-CH$_3$, 5-(2-fluoro-5-(trifluoromethoxy)phenyl) | X-1 | | 562 |
| 934 | 3-(2-methoxy-4-(trifluoromethyl)phenyl) | X-1 | | 544 |
| 935 | 2-F, 5-(2-(trifluoromethyl)-4-chlorophenyl) | X-1 | | 566 |
| 936 | 2-F, 5-(2,4-bis(trifluoromethyl)phenyl) | X-1 | | 600 |
| 937 | 3-(C(CH$_3$)=NOCH$_3$) | X-1 | | * |

* See Index Table D for $^1$H NMR data.

INDEX TABLE B-1

| Cmpd | R^A | R^B | m.p. (°C.) | AP+ (M+1) |
|---|---|---|---|---|
| 97 | 5-Br | X-5 | | 443 |
| 139 | 4-CF$_3$ | X-1 | | 439 |
| 222 | 4-CF$_3$ | CH$_2$CF$_3$ | | * |
| 224 | 4-CF$_3$ | X-6 | 118-120 | |
| 257 | 6-CF$_3$ | X-6 | | * |
| 466 | 5-F | X-5 | | 383 |
| 484 | 5-OCH$_3$ | X-5 | | 395 |
| 485 | 3-F | X-5 | | 383 |
| 486 | 3-Cl | X-5 | | 399 |
| 488 | 4-CF$_3$ | X-5 | | 433 |
| 489 | 6-CF$_3$ | X-5 | | 433 |
| 521 | 6-CF$_3$ | X-1 | | * |
| 602 | 6-(3-(trifluoromethyl)phenyl) | X-1 | | 515 |
| 686 | 4-Br | X-1 | | 449 |
| 720 | 4-(2-chloro-4-(trifluoromethyl)phenyl) | X-1 | | 549 |
| 721 | 3-CN | X-1 | | 396 |
| 722 | 3-CN | X-5 | | 390 |
| 736 | 5-CN | X-1 | | * |

* See Index Table D for $^1$H NMR data.

INDEX TABLE B-2

| Cmpd | R^A | R^B | AP+ (M+1) |
|---|---|---|---|
| 102 | 6-cyano | X-1 | 390 |
| 103 | 6-cyano | CH$_2$CF$_3$ | 347 |
| 258 | 5-(6-Cl-3-pyridinyl) | X-1 | 482 |
| 384 | 6-Cl | CH$_2$CF$_3$ | 356 |
| 398 | 6-F | CH$_2$CF$_3$ | 340 |
| 412 | 6-F | X-5 | * |
| 413 | 6-Cl | X-5 | * |
| 465 | 6-OCH$_3$ | X-5 | 395 |
| 468 | 5-CF$_3$ | X-5 | 433 |
| 471 | 2-F | X-5 | 383 |
| 626 | 3-(2,6-dichloro-3-pyridinyl) | X-1 | 515 |
| 641 | 5-Br | X-1 | * |
| 642 | 5-(2-chloro-4-(trifluoromethyl)phenyl) | X-1 | 549 |
| 662 | 6-Cl | X-1 | 405 |
| 663 | 6-CH$_3$ | X-1 | 385 |
| 664 | 6-CH$_2$CH$_3$ | X-1 | 399 |
| 678 | 5-CH$_3$ | X-1 | 385 |
| 679 | 5-CH$_2$CH$_3$ | X-1 | 399 |
| 695 | 6-F | X-1 | 389 |
| 696 | 2-Cl | X-1 | 405 |
| 697 | 2-F | X-1 | 389 |
| 717 | 2-(2-chloro-4-(trifluoromethyl)phenyl) | X-1 | 549 |
| 723 | 6-(4-(trifluoromethyl)phenyl) | X-1 | 515 |
| 752 | 6-OCH$_3$ | X-1 | * |
| 753 | 6-CN | X-1 | 396 |

* See Index Table D for $^1$H NMR data.

INDEX TABLE B-3

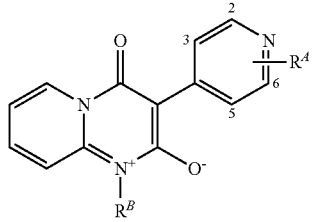

| Cmpd | $R^A$ | $R^B$ | m.p. (° C.) | AP+ (M + 1) |
|---|---|---|---|---|
| 98 | 2-($CF_3$) | X-6 | | 417 |
| 99 | 2,6-bis($CF_3$) | X-6 | | 485 |
| 100 | 2,6-bis($CF_3$) | X-5 | | 501 |
| 101 | 2,6-bis($CF_3$) | X-1 | | 507 |
| 243 | 2-Br | X-5 | | 443 |
| 247 | 2-(6-Cl-3-pyridinyl) | X-5 | | 476 |
| 251 | 2-Br | X-1 | | 449 |
| 265 | 2-CN | X-1 | | 396 |
| 280 | 2-Br | X-2 | | 493 |
| 283 | 2-$OCH_3$ | X-1 | | 401 |
| 284 | 2-$CF_3$ | X-1 | | 439 |
| 428 | 2-Cl | $CH_2CF_3$ | 248-249 | |
| 475 | 3-F | X-5 | | 383 |
| 520 | 2-Cl | X-1 | 242-243 | 405 |
| 590 | 2-Br | $CH_2CF_3$ | | 400 |
| 591 | 2-(4-(trifluoromethyl)phenyl) | X-1 | | 515 |
| 596 | 2-(4-(trifluoromethyl)phenyl) | $CH_2CF_3$ | | 466 |
| 597 | 2-(4-(trifluoromethyl)phenyl) | X-5 | | 509 |
| 611 | 2-Cl, 6-$CF_3$ | X-1 | | 473 |
| 617 | 2,6-diCl | X-1 | | 439 |
| 634 | 2-(2-chloro-4-(trifluoromethyl)phenyl) | X-1 | | 549 |

* See Index Table D for $^1H$ NMR data.

INDEX TABLE C

| Cmpd | $R^A$ | $R^B$ | m.p. (° C.) | AP+ (M + 1) |
|---|---|---|---|---|
| 104 | 3-Cl, 5-$OCF_3$ | X-1 | | 494 |
| 124 | 2,3-diF | X-5 | | 406 |
| 800 | 2,4-diF | $CH_2CF_3$ | | * |
| 801 | — | $CH_2CF_3$ | | * |
| 802 | 3-$OCF_3$ | $CH_2CF_3$ | | * |
| 803 | — | X-5 | | * |
| 804 | 4-F | X-5 | | * |
| 805 | — | X-1 | | * |
| 806 | 4-F | X-1 | | * |
| 807 | 3-$OCF_3$ | X-1 | | * |
| 808 | 3-Br, 5-$OCF_3$ | X-1 | | 538 |
| 809 | 2,4-diF | X-1 | | 412 |
| 810 | 3-$OCH_3$ | X-1 | | * |
| 811 | 2-F, 5-Cl | X-1 | | 428 |
| 812 | 3-$OCH_3$ | X-5 | | 400 |
| 813 | 3,5-di($OCH_3$) | X-5 | | 430 |
| 814 | 2,4-diF | X-5 | | 406 |
| 815 | 2-F, 5-$CF_3$ | X-1 | | * |
| 816 | 2-F, 5-$CF_3$ | X-5 | | 456 |
| 817 | 2-F, 5-Cl | X-5 | | 422 |
| 818 | 3-Br, 5-$OCF_3$ | X-5 | | 532 |
| 819 | 3,5-di($OCH_3$) | X-1 | | 436 |
| 820 | 2-$OCH_3$ | X-5 | 99-100 | |
| 821 | 2-F | X-1 | 192-194 | |
| 822 | 2-$OCH_3$ | X-1 | | * |
| 823 | — | X-6 | 223-225 | |
| 824 | 2-I | X-5 | | 496 |
| 825 | 3-$OCF_3$ | X-6 | | * |
| 826 | 2,4-diF | X-6 | 235-237 | |
| 827 | 2-F | X-6 | 223-225 | |
| 828 | 2-$OCH_3$ | X-6 | | * |
| 829 | 4-F | X-6 | | 372 |
| 830 | 3-$OCH_3$ | X-6 | | 384 |
| 831 | 2,3-diF | X-1 | | 412 |
| 832 | 2,3-diF | X-6 | | 390 |

* See Index Table D for $^1H$ NMR data.

INDEX TABLE D

| Cmpd No. | $^1H$ NMR Data $^a$ |
|---|---|
| 15 | δ (acetone-$d_6$) 9.48 (d, 1H), 9.07 (s, 1H), 8.90 (s, 2H), 8.33 (t, 1H), 8.05 (d, 1H), 7.88 (d, 1H), 7.56 (t, 1H), 7.42 (m, 3H), 7.30 (t, 2H) 5.76 (s, 2H). |
| 38 | δ (acetone-$d_6$) 9.48 (d, 1H), 9.07 (s, 1H), 8.89 (s, 2H), 8.33 (t, 1H), 8.05 (d, 1H), 7.91-7.94 (m, 2H), 7.57 (t, 1H), 7.06 (t, 2H), 5.76 (s, 2H). |
| 40 | δ (acetone-$d_6$) 9.41 (d, 1H), 9.07 (s, 1H), 8.90 (s, 2H), 8.31 (t, 1H), 7.93 (d, 1H), 7.53 (t, 1H), 7.36 (d, 1H), 7.24 (t, 1H), 7.01 (d, 1H), 6.95 (d, 1H), 5.64-5.81 (ab quartet, 2H), 3.31 (s, 3H). |
| 42 | δ (acetone-$d_6$) 9.41 (d, 1H), 9.07 (s, 1H), 8.89 (s, 2H), 8.36 (dd, 1H), 7.96 (d, 1H), 7.54-7.60 (m, 2H), 6.95-7.00 (m, 2H), 5.74 (s, 2H). |
| 43 | δ (acetone-$d_6$) 9.48 (d, 1H), 9.07 (s, 1H), 8.90 (s, 2H), 8.36 (dd, 1H), 8.05 (d, 1H), 8.02 (s, 1H), 7.94 (d, 1H), 7.59 (t, 1H), 7.42 (t, 1H), 7.10 (d, 1H) 5.77 (s, 2H). |
| 44 | δ (acetone-$d_6$) 9.47 (d, 1H), 9.07 (s, 1H), 8.90 (s, 2H), 8.35 (dd, 1H), 8.19 (s, 1H), 7.93-7.97 (m, 2H), 7.59 (t, 1H), 7.31 (t, 1H), 7.26 (t, 1H) 5.62 (s, 2H). |
| 89 | δ (acetone-$d_6$) 9.47 (d, 1H), 8.78 (s, 2H), 8.35 (t, 1H), 8.05 (d, 1H), 8.02 (s, 1H), 7.93 (d, 1H), 7.58 (t, 1H), 7.41 (t, 1H), 7.10 (d, 1H), 5.71 (s, 2H), 2.58 (s, 3H). |
| 90 | δ (acetone-$d_6$) 9.39 (d, 1H), 8.78 (s, 2H), 8.38 (t, 1H), 7.97 (d, 1H), 7.58 (t, 1H), 7.37 (t, 1H), 7.00 (t, 2H), 5.68 (s, 2H) 2.59 (s, 3H). |
| 127 | δ 9.56 (d, 1H), 8.48 (s, 1H), 8.05 (dd, 1H), 7.70 (d, 1H), 7.28-7.40 (m, 6H), 6.84 (m, 1H), 5.59 (br s, 2H), 3.84 (s, 3H). |
| 128 | δ 9.50 (d, 1H), 8.47 (s, 1H), 8.03 (dd, 1H), 7.69 (dd, 1H), 7.57 (td, 1H), 7.26-7.45 (m, 4H), 7.19 (t, 1H), 7.12 (dd, 1H), 5.56 (br s, 2H). |
| 129 | δ 9.53 (d, 1H), 8.49 (s, 1H), 8.10 (dd, 1H), 7.70 (dd, 1H), 7.26-7.45 (m, 4H), 7.10 (td, 1H), 7.00 (m, 1H), 5.58 (br s, 2H). |

INDEX TABLE D-continued

| Cmpd No. | $^1$H NMR Data $^a$ |
|---|---|
| 130 | δ 9.52 (d, 1H), 8.49 (s, 1H), 8.10 (dd, 1H), 7.69 (dd, 1H), 7.56 (dd, 1H), 7.4 (m, 2H), 7.09 (t, 1H), 5.58 (br s, 2H). |
| 131 | δ 9.51 (d, 1H), 8.48 (s, 1H), 8.11 (dd, 1H), 7.68 (dd, 1H), 7.4 (m, 3H), 7.34 (d, 1H), 6.76 (dd, 2H), 5.58 (br s, 2H). |
| 132 | δ 9.51 (d, 1H), 8.48 (s, 1H), 8.10 (dd, 1H), 7.70 (dd, 1H), 7.28-7.45 (m, 4H), 7.12 (m, 2H), 5.57 (br s, 2H). |
| 133 | δ 9.51 (d, 1H), 8.48 (s, 1H), 8.10 (dd, 1H), 7.10 (m, 2H), 7.3-7.45 (m, 4H), 7.03 (dd, 1H), 5.58 (br s, 2H). |
| 222 | δ (acetone-d$_6$) 9.50 (d, 1H), 8.85 (d, 1 H), 8.55 (t, 1H), 8.17 (d, 1H), 7.92 (s, 1H), 7.71 (t, 1H), 7.45 (d, 1H), 5.39 (br d, 2H). |
| 228 | δ (acetone-d$_6$) 9.45 (d, 1H), 8.48 (t, 1 H), 8.13 (d, 1H), 7.63 (t, 1H), 6.98-7.08 (m, 3H), 5.38 (br d, 2H), 3.87 (s, 3H). |
| 257 | δ (acetone-d$_6$) 9.41 (d, 1H), 8.35-8.43 (m, 2H), 7.98-8.05 (m, 2H), 7.88-7.92 (m, 2H), 7.63 (d, 1H), 7.59 (t, 1H), 7.05 (d, 1H), 5.74 (s, 2H). |
| 312 | δ 9.61 (d, 1H), 8.24 (t, 1H), 7.78 (dd, 1H), 7.67 (d, 1H), 7.50 (t, 1H), 7.44 (d, 2H), 6.69 (t, 1H). |
| 313 | δ 9.60 (d, 1H), 8.23 (t, 1H), 7.75 (d, 2H), 7.59 (d, 1H), 7.51 (t, 2H), 7.24 (m, 2H). |
| 321 | δ 9.58 (d, 1H), 8.16 (t, 1H), 7.74 (d, 2H), 7.49 (d, 1H), 7.40 (t, 3H), 7.25 (m, 1H), 4.58 (dd, 2H), 2.85 (m, 2H). |
| 322 | δ (acetone-d$_6$) 9.5 (m, 1H), 8.5 (m, 1H), 8.1 (m, 1H), 7.97 (s, 1H), 7.75 (dd, 1H), 7.69 (m, 1H), 7.31 (t, 1H), 7.15 (m, 1H), 5.35 (br s, 2H). |
| 326 | δ 9.57 (d, 1H), 8.23 (t, 1H), 7.58 (d, 1H), 7.46 (t, 2H), 7.38(s, 1H), 6.90 (d, 1H), 3.79 (s, 3H). |
| 330 | δ 9.58 (d, 1H), 8.23 (t, 1H), 7.61 (d, 1H), 7.51 (t, 1H), 7.48 (d, 1H), 7.14 (m, 2H). |
| 331 | δ 9.55 (dd, 1H), 8.17 (t, 1H), 7.67 (d, 1H), 7.59 (d, 1H), 7.52 (dd, 1H), 7.45 (t, 1H), 6.99 (d, 1h), 5.3 (br s, 1H), 4.9 (br s, 1H), 4.10 (q, 2H), 1.31 (t, 3H). |
| 333 | δ 9.57 (d, 1H), 8.19 (t, 1H), 7.78 (dd, 1H), 7.67 (dd, 1H), 7.35-7.55 (m, 3H), 7.09 (d, 1H), 4.7-5.05 (m, 2H), 4.37 (m, 1H), 2.2-2.55 (m, 2H). |
| 334 | δ 9.55 (d, 1H), 8.23 (t, 1H), 7.98 (d, 2H), 7.66 (d, 2H), 7.52 (d, 1H), 7.44 (t, 1H), 4.85-5.05 (m, 1H), 4.75 (m, 1H), 4.40 (m, 1H), 2.2-2.6 (m, 2H). |
| 335 | δ 9.57 (d, 1H), 8.23 (t, 1H), 7.61 (d, 1H), 7.49 (m, 2H), 6.8-6.95 (m, 2H), 5.2 (br s, 2H). |
| 336 | δ 9.59 (dd, 1H), 8.25 (t, 1H), 7.59 (d, 1H), 7.50 (t, 1H), 7.23-7.28 (m, 1H), 7.07 (td, 1H), 7.04 (m, 1H), 5.10 (br s, 2H). |
| 342 | δ 9.57 (d, 1H), 8.17 (t, 1H), 7.74 (m, 2H), 7.49 (d, 1H), 7.41 (t, 1H), 7.08 (t, 2H), 4.7-5.05 (m, 2H), 4.37 (m, 1H), 2.2-2.55 (m, 2H). |
| 355 | δ 9.61 (d, 1H), 8.21 (t, 1H), 7.73 (m, 2H), 7.56 (d, 1H), 7.49 (t, 1H), 7.08 (t, 2H). |
| 356 | δ 9.59 (d, 1H), 8.15 (t, 1H), 7.72 (d, 2H), 7.52 (d, 1H), 7.44 (t, 1H), 7.38 (t, 2H), 7.23 (t, 1H), 5.5 (br s, 2H). |
| 357 | δ 9.61 (d, 1H), 8.21 (t, 1H), 7.76 (d, 1H), 7.71 (s, 1H), 7.55 (dt, 1H), 7.49 (t, 1H), 7.39 (t, 1H), 7.10 (d, 1H). |
| 358 | δ 9.60 (dd, 1H), 8.26 (t, 1H), 8.16 (t, 1H), 8.12 (m, 1H), 7.62 (d, 1H), 7.53 (t, 1H), 7.20 (t, 1H), 5.10 (br s, 2H). |
| 359 | δ 9.59 (d, 1H), 8.23 (t, 1H), 7.58 (d, 1H), 7.50 (m, 2H), 7.50 (t, 1H), 6.85-6.95 (m, 2H). |
| 360 | δ 9.54 (d, 1H), 8.21 (t, 1H), 7.51 (m, 2H), 7.42 (t, 1H), 6.9 (m, 2H), 4.7-5.05 (m, 2H), 4.37 (m, 1H), 2.2-2.55 (m, 2H). |
| 363 | δ 9.57 (d, 1H), 8.23 (t, 1H), 7.61 (d, 1H), 7.49 (t, 2H), 7.41 (d, 1H), 7.29 (d, 1H), 5.2 (br s, 2H). |
| 366 | δ (acetone-d$_6$) 9.45 (d, 1H), 8.45 (m, 1H), 8.1 (d, 1H), 7.63 (t, 1H), 7.3 (d, 1H), 7.22 (m, 1H), 7.95 (dd, 1H), 6.9 (t, 1H), 5.35 (br s, 2H), 3.73 (s, 3H). |
| 374 | δ 9.56 (d, 1H), 8.23 (t, 1H), 7.59 (d, 1H), 7.49 (m, 2H), 7.16 (t, 2H), 5.2 (br s, 2H). |
| 393 | δ 9.56 (d, 1H), 8.48 (s, 1H), 8.05 (dd, 1H), 7.79 (d, 2H), 7.70 (dd, 1H), 7.2-7.45 (m, 6H), 5.59 (br s, 2H). |
| 395 | δ 9.51 (d, 1H), 8.48 (s, 1H), 8.08 (dd, 1H), 7.69 (ddd, 1H), 7.54 (q, 1H), 7.3-7.45 (m, 4H), 6.85-7.0 (m, 2H), 5.57 (br s, 2H). |
| 396 | δ 9.56 (d, 1H), 8.47 (s, 1H), 8.08 (dd, 1H), 7.81 (d, 1H), 7.77 (s, 1H), 7.68 (dd, 1H), 7.3-7.45 (m, 4H), 7.12 (d, 1H), 5.59 (br s, 2H). |
| 399 | δ 9.56 (d, 1H), 8.48 (s, 1H), 8.05 (dd, 1H), 7.79 (d, 1H), 7.77 (dd, 1H), 7.3-7.45 (m, 4H), 7.24 (d, 1H), 5.59 (br s, 2H). |
| 405 | δ 9.54 (d, 1H), 8.47 (s, 1H), 8.0-8.15 (m, 3H), 7.67 (dd, 1H), 7.4 (m, 2H), 7.33 (d, 1H), 7.21 (dd, 1H), 5.59 (br s, 2H). |
| 406 | δ 9.52 (d, 1H), 8.48 (s, 1H), 8.10 (dd, 1H), 7.70 (d, 1H), 7.48 (dd, 1H), 7.42 (m, 2H), 7.34 (d, 1H), 7.25 (d, 1H), 7.06 (td, 1H), 5.59 (br s, 2H). |
| 408 | δ 9.54 (d, 1H), 8.48 (s, 1H), 8.1 (m, 2H), 7.75 (m, 1H), 7.68 (dd, 1H), 7.4 (m, 3H), 7.37 (d, 1H), 7.15 (t, 1H), 5.58 (br s, 2H). |
| 409 | δ 9.53 (d, 1H), 8.48 (s, 1H), 8.11 (dd, 1H), 7.79 (d, 1H), 7.70 (dd, 1H), 7.51 (d, 1H), 7.4 (m, 3H), 7.35 (d, 1H), 7.15 (d, 1H), 5.75 (br d, 1H), 5.4 (br d, 1H). |
| 410 | δ 9.52 (d, 1H), 8.48 (s, 1H), 8.10 (dd, 1H), 7.68 (dd, 2H), 7.3-7.5 (m, 6H), 5.57 (br s, 2H). |
| 411 | δ 9.52 (d, 1H), 8.48 (s, 1H), 8.10 (dd, 1H), 7.72 (dd, 1H), 7.3-7.5 (m, 5H), 7.11 (td, 1H), 5.8 (br d, 1H), 5.4 (br d, 1H). |
| 412 | δ 9.55 (d, 1H), 8.71 (s, 1H), 8.47 (s, 1H), 8.30 (dd, 1H), 8.11 (dd, 1H), 7.67 (dd, 1H), 7.42 (m, 2H), 7.33 (d, 1H), 5.60 (br s, 2H). |
| 413 | δ 9.56 (d, 1H), 8.92 (s, 1H), 8.47 (s, 1H), 8.21 (dd, 1H), 8.11 (dd, 1H), 7.3-7.45 (m, 4H), 5.59 (br s, 2H). |
| 414 | δ 9.50 (d, 1H), 8.47 (s, 1H), 8.08 (dd, 1H), 7.68 (dd, 1H), 7.50 (d, 1H), 7.3-7.45 (m, 5H), 5.7 (br d, 1H), 5.4 (br d, 1H). |
| 415 | δ 9.55 (d, 1H), 8.47 (s, 1H), 8.07 (dd, 1H), 7.65-7.75 (m, 3H), 7.53 (d, 2H), 7.51 (d, 1H), 7.4 (m, 2H), 7.32 (d, 1H), 5.58 (br s, 2H). |
| 416 | δ 9.56 (d, 1H), 8.48 (s, 1H), 8.12 (dd, 1H), 8.02 (d, 2H), 7.67 (d, 2H), 7.4 (m, 3H), 7.34 (d, 1H), 5.59 (br s, 2H). |

INDEX TABLE D-continued

| Cmpd No. | ¹H NMR Data<sup>a</sup> |
|---|---|
| 417 | δ 9.52 (d, 1H), 8.46 (s, 1H), 8.06 (dd, 1H), 7.68 (d, 1H), 7.3-7.55 (m, 5H), 7.25 (d, 1H), 5.6 (br dd, 2H), 2.26 (s, 3H). |
| 418 | δ 9.51 (d, 1H), 8.50 (s, 1H), 8.08 (d, 2H), 7.75 (d, 2H), 7.66 (dd, 2H), 7.3-7.45 (m, 3H), 7.2-7.25 (m, 1H), 5.69 (s, 2H). |
| 419 | δ 9.56 (d, 1H), 8.48 (s, 1H), 8.14 (s, 1H), 8.09 (dd, 1H), 8.07 (d, 1H), 7.69 (dd, 1H), 7.51 (m, 2H), 7.40 (m, 2H), 5.6 (br s, 2H). |
| 420 | δ 9.53 (d, 1H), 8.47 (s, 1H), 8.13 (dd, 1H), 7.68 (d, 1H), 7.60 (s, 1H), 7.53 (s, 2H), 7.43 (m, 2H), 7.35 (d, 1H) 5.60 (br d, 2H). |
| 421 | δ 9.55 (d, 1H), 8.48 (s, 1H), 8.07 (dd, 1H), 7.78 (d, 2H), 7.69 (dd, 1H), 7.4 (m, 4H), 7.32 (d, 1H), 5.59 (br s, 2H). |
| 422 | δ 9.54 (dd, 1H), 8.47 (d, 1H), 8.10 (m, 1H), 7.79 (d, 1H), 7.67 (dd, 1H), 7.33-7.43 (m, 2H), 7.2-7.3 (m, 3H), 5.58 (br s, 2H). |
| 429 | δ 9.55 (d, 1H), 8.48 (s, 1H), 8.08 (dd, 1H), 7.83 (d, 1H), 7.77 (dd, 1H), 7.3-7.45 (m, 4H), 7.24 (d, 1H), 5.59 (br s, 2H). |
| 430 | δ 9.54 (d, 1H), 8.47 (s, 1H), 8.07 (dd, 1H), 7.99 (s, 1H), 7.76 (d, 1H), 7.68 (d, 1H), 7.25-7.45 (m, 5H), 5.58 (br s, 2H). |
| 431 | δ 9.56 (d, 1H), 8.48 (s, 1H), 8.03 (dd, 1H), 7.74 (d, 2H), 7.69 (dd, 1H), 7.3-7.4 (m, 3H), 6.97 (d, 2H), 5.59 (br s, 2H). |
| 432 | δ 9.56 (d, 1H), 8.48 (s, 1H), 8.08 (dd, 1H), 7.86 (d, 2H), 7.69 (dd, 1H), 7.3-7.45 (m, 3H), 7.26 (d, 1H), 5.59 (br s, 2H). |
| 433 | δ 9.55 (d, 1H), 8.48 (s, 1H), 8.09 (dd, 1H), 7.65-7.75 (m, 2H), 7.6 (m, 1H), 7.41 (m, 2H), 7.33 (d, 1H), 7.17 (q, 1H), 5.58 (br s, 2H). |
| 434 | δ 9.51 (d, 1H), 8.48 (s, 1H), 8.12 (dd, 1H), 7.69 (dd, 1H), 7.4-7.5 (m, 2H), 7.33 (d, 1H), 7.27 (m, 1H), 7.02 (dd, 1H), 5.58 (br s, 2H). |
| 435 | δ 9.52 (d, 1H), 8.48 (s, 1H), 8.11 (dd, 1H), 7.68 (dd, 2H), 7.35-7.45 (m, 3H), 7.34 (d, 1H), 6.95-7.05 (m, 1H), 5.57 (br s, 2H). |
| 436 | δ 9.52 (d, 1H), 8.47 (s, 1H), 8.10 (dd, 1H), 8.04 (s, 1H), 7.78 (s, 1H), 7.66 (dd, 1H), 7.3-7.45 (m, 4H), 5.57 (br s, 2H). |
| 437 | δ 9.56 (d, 1H), 8.48 (s, 1H), 8.07 (dd, 1H), 7.69 (d, 1H), 7.49 (d, 1H), 7.3-7.45 (m, 4H), 7.12 (dd, 1H), 5.59 (br s, 2H), 3.93 (s, 3H). |
| 438 | δ 9.53 (d, 1H), 8.49 (s, 1H), 8.11 (dd, 1H), 7.69 (d, 1H), 7.50 (d, 1H), 7.41 (m, 2H), 7.34 (d, 1H), 7.16 (d, 2H), 7.58 (br s, 2H). |
| 441 | δ 9.53 (d, 1H), 8.48 (s, 1H), 8.20 (s, 1H), 8.11 (m, 2H), 7.68 (dd, 1H), 7.4-7.55 (m, 4H), 7.34 (d, 1H), 5.59 (br s, 2H). |
| 442 | δ 9.49 (d, 1H), 8.53 (d, 1H), 8.05 (s, 2H), 7.78 (m, 2H), 7.68 (t, 1H), 7.55 (d, 1H), 7.33 (m, 1H), 7.09 (t, 2H), 5.68 (br s, 2H). |
| 444 | δ 9.53 (d, 1H), 8.69 (s, 1H), 8.60 (d, 1H), 8.07 (m, 2H), 7.80 (s, 1H), 7.66 (d, 1H), 7.4 (m, 2H), 7.25 (m, 2H), 5.63 (br s, 2H). |
| 445 | δ 9.58 (d, 1H), 8.22 (m, 1H), 7.61 (d, 1H), 7.48 (t, 1H), 7.30 (m, 1H), 6.98 (d, 1H), 6.93 (m, 1H), 5.2 (br s, 2H), 2.24 (s, 3H). |
| 446 | δ 9.59 (d, 1H), 8.38 (s, 1H), 8.10 (dd, 1H), 7.8 (m, 3H), 7.42 (t, 1H), 7.36 (d, 1H), 7.11 (t, 2H), 5.59 (br s, 2H). |
| 447 | δ 9.58 (dd, 1H), 8.38 (s, 1H), 8.11 (t, 1H), 7.80 (m, 3H), 7.42 (m, 2H), 7.36 (d, 1H), 7.11 (d, 1H), 5.58 (br s, 2H). |
| 448 | δ 9.53 (d, 1H), 8.47 (s, 1H), 8.08 (dd, 1H), 7.69 (t, 1H), 7.3-7.45 (m, 4H), 6.9-7.05 (m, 2H), 5.6 (br dd, 2H), 2.28 (s, 3H). |
| 450 | δ 9.58 (d, 1H), 8.38 (s, 1H), 8.07 (dd, 1H), 7.8 (m, 3H), 7.3-7.45 (m, 4H), 7.26 (m, 1H), 5.57 (br s, 2H). |
| 451 | δ 9.56 (d, 1H), 8.48 (s, 1H), 8.08 (dd, 1H), 7.70 (dd, 1H), 7.63 (d, 1H), 7.58 (m, 1H), 7.3-7.45 (m, 4H), 6.95 (td, 1H), 5.58 (br s, 2H). |
| 452 | δ 9.56 (d, 1H), 8.48 (s, 1H), 8.10 (dd, 1H), 7.97 (d, 2H), 7.6-7.75 (m, 3H), 7.41 (m, 2H), 7.33 (d, 1H), 5.60 (br s, 2H). |
| 455 | δ 9.56 (d, 1H), 8.48 (s, 1H), 8.03 (dd, 1H), 7.68 (m, 3H), 7.36 (m, 1H), 7.31 (d, 1H), 7.23 (d, 1H), 5.58 (br s, 2H), 2.37 (s, 3H). |
| 456 | δ 9.56 (d, 1H), 8.48 (s, 1H), 8.05 (dd, 1H), 7.81 (d, 2H), 7.69 (dd, 1H), 7.3-7.45 (m, 3H), 7.17 (d, 2H), 6.52 (t, 1H), 5.59 (br s, 2H). |
| 458 | δ 9.53 (d, 1H), 8.48 (s, 1H), 8.11 (dd, 1H), 7.79 (t, 1H), 7.69 (dd, 1H), 7.25-7.45 (m, 4H), 5.58 (br s, 2H). |
| 459 | δ 9.59 (dd, 1H), 8.38 (s, 1H), 8.07 (t, 1H), 7.82 (s, 1H), 7.74 (d, 2H), 7.40 (t, 1H), 7.37 (d, 1H), 6.98 (d, 2H), 5.58 (br s, 2H), 3.84 (s, 3H). |
| 461 | δ 9.53 (d, 1H), 8.48 (s, 1H), 8.07 (t, 1H), 7.71 (d, 1H), 7.47 (t, 1H), 7.38 (m, 2H), 7.32 (d, 1H), 6.75 (m, 2H), 5.58 (br s, 2H). |
| 464 | δ 9.55 (d, 1H), 8.48 (s, 1H), 8.05 (dd, 1H), 7.55-7.95 (m, 3H), 7.3-7.45 (m, 3H), 7.02 (dd, 1H), 5.58 (br s, 2H), 3.91 (s, 3H). |
| 467 | δ 9.55 (d, 1H), 8.48 (s, 1H), 8.25 (s, 1H), 8.14 (s, 1H), 8.11 (dd, 1H), 7.66 (m, 2H), 7.4 (m, 2H), 7.34 (d, 1H), 5.59 (br s, 2H). |
| 469 | δ 9.52 (d, 1H), 8.48 (s, 1H), 8.12 (dd, 1H), 7.65-7.75 (m, 2H), 7.47 (d, 1H), 7.42 (t, 2H), 7.37 (d, 1H), 5.58 (br s, 2H). |
| 470 | δ 9.55 (d, 1H), 8.48 (s, 1H), 8.10 (m, 3H), 7.67 (d, 1H), 7.48 (s, 1H), 7.42 (m, 2H), 7.36 (d, 1H), 5.59 (br s, 2H). |
| 474 | δ 9.58 (dd, 1H), 8.12 (m, 1H), 7.82 (d, 1H), 7.78 (s, 1H), 7.49 (d, 1H), 7.42 (m, 2H), 7.26 (m, 2H), 7.12 (d, 1H), 5.67 (br s, 2H). |
| 476 | δ 9.53 (d, 1H), 8.49 (s, 1H), 8.12 (dd, 1H), 7.90 (d, 1H), 7.69 (dd, 1H), 7.65 (m, 1H), 7.2-7.45 (m, 4H), 5.59 (br s, 2H). |
| 480 | δ 9.55 (m, 1H), 8.15 (m, 1H), 7.75 (m, 2H), 7.67 (s, 1H), 7.6 (dd, 1H), 7.42 (m, 1H), 7.1 (m, 2H), 5.58 (br s, 2H). |
| 481 | δ 9.5 (m, 1H), 8.15 (m, 1H), 7.65 (s, 1H), 7.6 (dd, 1H), 7.5 (m, 1H), 7.4 (m, 1H), 6.9 (m, 2H), 5.55 (br s, 2H). |

INDEX TABLE D-continued

| Cmpd No. | $^1$H NMR Data $^a$ |
|---|---|
| 487 | δ 9.53 (d, 1H), 8.48 (s, 1H), 8.14 (t, 1H), 7.75 (t, 1H), 7.68 (dd, 1H), 7.51 (d, 1H), 7.4 (m, 3H), 7.34 (d, 1H), 5.58 (br s, 2H). |
| 512 | δ (acetone-d$_6$) 9.43 (d, 1H), 8.41 (t, 1H), 8.18 (d, 1H), 7.96 (s, 1H), 7.75 (d, 1H), 7.59 (t, 1H), 7.50-7.56 (m, 1H), 7.05 (dd, 1H), 5.77 (s, 2H), 3.88 (s, 3H). |
| 521 | δ (acetone-d$_6$) 9.41 (d, 1H), 8.45 (t, 1H), 8.20 (d, 1H), 7.95-8.05 (m, 2H), 7.88 (d, 1H), 7.59-7.65 (m, 2H), 5.75 (br s, 2H). |
| 524 | δ 9.51 (d, 1H), 8.21 (t, 1H), 7.67 (s, 1H), 7.62 (d, 1H), 7.42 (t, 1H), 6.75 (t, 2H), 5.59 (s, 2H). |
| 641 | δ (acetone-d$_6$) 9.45 (d, 1H), 9.21 (s, 1H), 8.60 (s, 1H), 8.50-8.40 (m, 2H), 8.22 (d, 1H), 7.97 (s, 1H), 7.62 (t, 1H), 5.79 (s, 2H). |
| 736 | δ (acetone-d$_6$) 9.43 (dd, 1), 8.92 (s, 1), 8.47 (m, 1), 8.21 (d, 1), 8.10 (dd, 1), 7.95 (m, 2), 7.62 (t, 1), 5.76 (s, 2). |
| 752 | δ (acetone-d$_6$) 9.46 (dd, 1), 8.71 (d, 1), 8.40-8.44 (m, 1), 8.17-8.21 (m, 2), 7.97 (s, 1), 7.60 (t, 1), 6.74 (d, 1), 5.77 (s, 2), 3.90 (s, 3). |
| 800 | δ 8.30 (d, 1H), 7.46 (m, 1H), 7.16 (d, 1H), 6.8-6.9 (m, 2H), 4.8 (br s, 2H). |
| 801 | δ 8.32 (d, 1H), 7.72 (d, 2H), 7.38 (dd, 2H), 7.23 (dd, 1H), 7.13 (d, 1H), 4.81 (q, 2H). |
| 802 | δ 8.32 (d, 1H), 7.73 (d, 1H), 7.69 (s, 1H), 7.37 (t, 1H), 7.15 (d, 1H), 7.08 (d, 1H), 4.81 (q, 2H). |
| 803 | δ 8.52 (d, 1H), 8.28 (d, 1H), 7.91 (dd, 1H), 7.72 (d, 2H), 7.35-7.4 (m, 3H), 7.25 (m, 1H, partially obscured by solvent peak), 7.03 (d, 1H), 5.31 (s, 2H). |
| 804 | δ (acetone-d$_6$) 8.61 (d, 1H), 8.20 (d, 1H), 7.98 (d, 1H), 7.89 (m, 2H), 7.55 (dd, 1H), 7.47 (m, 1H), 7.03 (dd, 2H), 5.46 (s, 2H). |
| 805 | δ 8.29 (d, 1H), 7.67-7.72 (m, 3H), 7.25 (m, 1H, partially obscured by solvent peak), 7.09 (d, 1H), 5.34 (s, 2H). |
| 806 | δ 8.28 (d, 1H), 7.67-7.73 (m, 3H), 7.04-7.11 (m, 3H), 5.33 (s, 2H). |
| 807 | δ 8.25 (s, 1H), 7.65-7.75 (m, 3H), 7.38 (dd, 1H), 7.08 (d, 1H), 5.32 (d, 1H). |
| 810 | δ 8.27 (d, 1H), 7.67 (s, 1H), 7.31 (m, 3H), 7.07 (d, 1H), 6.80 (m, 1H), 5.33 (s, 2H), 3.82 (s, 3H). |
| 815 | δ 8.27 (d, 1H), 7.82 (m, 1H), 7.69 (s, 1H), 7.56 (m, 1H), 7.23 (m, 1H), 7.14 (d, 1H), 5.35 (s, 2H). |
| 822 | δ (acetone-d$_6$) 8.17 (d, 1H), 7.88 (s, 1 H), 7.59 (d, 1H), 7.21-7.29 (m, 2H), 6.99 (d, 1H), 6.88 (t, 1H), 5.45 (d, 2H), 3.76 (s, 3H). |
| 825 | δ (acetone-d$_6$) 8.45 (d, 1H), 8.19 (m, 1H), 8.10 (m, 1H), 8.00 (m, 2H), 7.53 (m, 1H), 7.38 (m, 1H), 7.10-7.00 (m, 2H), 5.45 (s, 2H). |
| 828 | δ (acetone-d$_6$) 8.45 (s, 1H), 8.10 (m, 2H), 7.50 (m, 1H), 7.30 (m, 1H), 7.20 (m, 1H), 7.15 (m, 1H), 6.95 (m, 1H), 6.90 (m, 1H), 5.50-5.30 (dd, 2H), 3.76 (s, 3H). |
| 937 | δ 9.52 (dd, 1H), 8.10 (td, 1H), 8.03 s, 1H), 7.75 (d, 1H), 7.65 (s, 1H), 7.55 (d, 2H), 7.38 (q, 2H), 5.55 (br s, 2H), 3.98 (s, 3H), 2.24 (s, 3H). |

$^a$ $^1$H NMR data are in ppm downfield from tetramethylsilane. CDCl$_3$ solution unless indicated otherwise.
Couplings are designated by (s)—singlet, (d)—doublet, (t)—triplet, (m)—multiplet, (dd)—doublet of doublets, (ddd)—doublet of doublet of doublets, (dt)—doublet of triplets, (td)—triplet of doublets, (br)—broad.

Synergism manifested by mixtures of two active ingredients may allow a substantial reduction in the application rates of one or both of these active ingredients, while maintaining good biological efficacy. The greater than expected effect may persist for days after application, facilitating rapid knockdown and mortality. Decreasing application rates reduces treatment cost to the farmer and also eases the burden on the environment both from manufacturing waste and crop protection chemical residues.

The presence of a synergistic effect between two active ingredients can be established with the aid of the Colby equation (see Colby, S. R., "Calculating Synergistic and Antagonistic Responses of Herbicide Combinations", *Weeds* 1967, 15, 20-22):

$$p = A + B - \left[\frac{A \times B}{100}\right]$$

Using the method of Colby, the presence of a synergistic interaction between two active ingredients is established by first calculating the predicted activity, p, of the mixture based on activities of the two components applied alone. In the equation above, A is the biological activity in percentage control of one component applied alone at rate x. The B term is the biological activity in percentage control of the second component applied at rate y. The equation calculates p, the predicted biological activity of the mixture of A at rate x with B at rate y if their effects are strictly additive and no interaction has occurred. If the experimentally established effect of the mixture is greater than the predicted activity, p, synergism is present. To use the Colby equation the active ingredients of the mixture are applied in a test separately as well as in combination.

The following Tests demonstrate the control efficacy of compositions of this invention on specific pests. "Control efficacy" represents inhibition of invertebrate pest development (including mortality) that causes significantly reduced feeding. The pest control protection afforded by the compounds is not limited, however, to these species. See Index Tables A-C for compound descriptions.

Biological Examples of the Invention

Test A

For evaluating control of diamondback moth (*Plutella xylostella*) the test unit consisted of a small open container with a 12-14-day-old radish plant inside. This was pre-infested with ~50 neonate larvae that were dispensed into the test unit via corn cob grits using a bazooka inoculator. The larvae moved onto the test plant after being dispensed into the test unit.

Test compounds and compositions were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc. Greeley, Colo., USA). The formulated compounds or compositions were applied in 1 mL of liquid through a SUJ2 atomizer nozzle with 1/8 JJ custom body (Spraying Systems Co. Wheaton, Ill., USA) positioned 1.27 cm (0.5 inches) above the top of each test unit. Tests were replicated three times. After spraying of the formulated test compound or compositions, each test unit was allowed to dry for 1 h and then a black, screened cap was placed on top. The test units were held for 6 days in a growth chamber at 25° C. and 70% relative humidity. Plant feeding damage was then visually assessed based on foliage consumed.

The results calculated as mean averages of results from the three replicates are listed in Table A. Compound 123 was applied at a rate of 0.1 ppm. Compound 8 was applied at a rate of 20 ppm. The additional invertebrate pest control agent is designated as "Compound A" and was applied at the rates shown in Table A.

TABLE A

| | | Plant Protection * | | | | | | |
|---|---|---|---|---|---|---|---|---|
| | | Observed | | | | | Expected ** | |
| Compound A | rate (ppm) | Cmpd 123 | Cmpd 8 | Cmpd A | Cmpd 123 + Cmpd A | Cmpd 8 + Cmpd A | Cmpd 123 + Cmpd A | Cmpd 8 + Cmpd A |
| thiamethoxam | 21.2 | 33 | 13 | 20 | 73 | 43 | 46 | 30 |
| buprofezin | 250 | 33 | 13 | 0 | 17 | 20 | 33 | 13 |
| dinotefuran | 2.5 | 33 | 13 | 17 | 0 | 0 | 44 | 28 |
| chlorpyrifos | 250 | 33 | 13 | 0 | 43 | 0 | 33 | 13 |
| acetamiprid | 5 | 33 | 13 | 63 | 73 | 0 | 75 | 68 |
| oxamyl | 250 | 17 | 0 | 0 | 63 | 0 | 17 | 0 |
| spirotetramat | 25 | 17 | 0 | 43 | 80 | 70 | 53 | 43 |
| flonicamid | 2 | 17 | 0 | 10 | 63 | 23 | 25 | 10 |
| methomyl | 10 | 17 | 0 | 27 | 70 | 13 | 39 | 27 |
| lambda-cyhalothrin | 0.01 | 17 | 0 | 40 | 90 | 23 | 50 | 40 |
| indoxacarb | 1 | 17 | 0 | 40 | 47 | 80 | 50 | 40 |
| spinetoram | 0.01 | 17 | 0 | 40 | 63 | 73 | 50 | 40 |
| fipronil | 1 | 17 | 0 | 97 | 97 | 93 | 98 | 97 |
| pyriproxifen | 250 | 17 | 0 | 0 | 53 | 7 | 17 | 0 |
| thiodicarb | 0.2 | 17 | 0 | 33 | 20 | 27 | 44 | 33 |
| chlorfenapyr | 0.2 | 17 | 0 | 3 | 50 | 23 | 19 | 3 |
| chlorantraniliprole | 0.02 | 97 | 40 | 93 | 93 | 63 | 100 | 96 |
| cyantraniliprole | 0.025 | 97 | 40 | 43 | 77 | 63 | 98 | 66 |
| clothianidin | 5 | 97 | 40 | 27 | 63 | 40 | 98 | 56 |
| tolfenpyrad | 0.5 | 97 | 40 | 0 | 43 | 0 | 97 | 40 |
| cartap | 250 | 97 | 40 | 10 | 70 | 10 | 97 | 46 |
| methoxyfenozide | 10 | 97 | 40 | 30 | 67 | 13 | 98 | 58 |
| pyridalyl | 10 | 80 | 17 | 43 | 93 | 0 | 89 | 53 |
| flubendiamide | 0.05 | 80 | 17 | 57 | 67 | 60 | 91 | 64 |
| abamectin | 0.00125 | 80 | 17 | 50 | 73 | 60 | 90 | 59 |
| pymetrozine | 250 | 80 | 17 | 53 | 97 | 47 | 91 | 61 |
| thiacloprid | 0.25 | 80 | 17 | 23 | 63 | 27 | 85 | 36 |
| novaluron | 0.1 | 80 | 17 | 27 | 100 | 57 | 85 | 39 |

* Plant Protection = (0 to 10 rating) × 10. Rating is on a scale of 0 to 10, 0 meaning no visible plant damage and 10 meaning complete plant damage.
** Expected based on calculation using the Colby equation.

Test B

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The aphids moved onto the test plant as the leaf piece desiccated. After pre-infestation, the soil of the test unit was covered with a layer of sand.

Test compounds and compositions were formulated and sprayed as described for Test A. The applications were replicated three times. After spraying of the formulated test compound or composition, each test unit was allowed to dry for 1 h and then a black, screened cap was placed on top. The test units were held for 6 days in a growth chamber at 19-21° C. and 50-70% relative humidity. Each test unit was then visually assessed for insect mortality.

The results calculated as mean averages of results from the three replicates are listed in Table B. Compound 123 was applied at a rate of 50 ppm. Compound 8 was applied at a rate of 250 ppm. The additional invertebrate pest control agent is designated as "Compound A" and was applied at the rates shown in Table B.

TABLE B

| | | Percent Mortality | | | | | | |
|---|---|---|---|---|---|---|---|---|
| | | Observed | | | | | Expected * | |
| Compound A | rate (ppm) | Cmpd 123 | Cmpd 8 | Cmpd A | Cmpd 123 + Cmpd A | Cmpd 8 + Cmpd A | Cmpd 123 + Cmpd A | Cmpd 8 + Cmpd A |
| thiamethoxam | 0.2 | 15 | 25 | 40 | 48 | 38 | 49 | 55 |
| buprofezin | 250 | 15 | 25 | 14 | 31 | | 27 | 35 |
| dinotefuran | 2.5 | 15 | 25 | 33 | 50 | 31 | 43 | 50 |
| chlorpyrifos | 250 | 15 | 25 | 18 | 19 | 23 | 30 | 39 |
| acetamiprid | 0.2 | 15 | 25 | 9 | 21 | 48 | 23 | 32 |
| oxamyl | 83.3 | 18 | 13 | 23 | 22 | 39 | 37 | 33 |
| spirotetramat | 0.25 | 18 | 13 | 8 | 21 | 34 | 24 | 19 |
| flonicamid | 1 | 18 | 13 | 14 | 26 | 62 | 29 | 25 |
| methomyl | 20 | 18 | 13 | 28 | 13 | 10 | 41 | 37 |
| lambda-cyhalothrin | 250 | 18 | 13 | 39 | 76 | 69 | 50 | 47 |
| indoxacarb | 50 | 22 | 10 | 32 | 43 | 70 | 47 | 39 |
| spinetoram | 5 | 22 | 10 | 10 | 15 | 33 | 30 | 19 |
| fipronil | 10 | 22 | 10 | 87 | 77 | 96 | 90 | 88 |
| pyriproxifen | 250 | 22 | 10 | 10 | 5 | 9 | 30 | 19 |
| thiodicarb | 30 | 22 | 10 | 25 | 13 | 19 | 42 | 33 |
| chlorfenapyr | 10 | 22 | 10 | 54 | 40 | 65 | 64 | 58 |
| chlorantraniliprole | 4 | 9 | 15 | 11 | 19 | 25 | 19 | 24 |
| cyantraniliprole | 0.5 | 9 | 15 | 10 | 15 | 44 | 17 | 23 |
| clothianidin | 0.2 | 9 | 15 | 16 | 46 | 76 | 23 | 29 |
| tolfenpyrad | 3 | 9 | 15 | 77 | 30 | 80 | 79 | 81 |
| cartap | 250 | 9 | 15 | 15 | 3 | 12 | 22 | 27 |
| methoxyfenozide | 250 | 9 | 15 | 16 | 4 | 12 | 23 | 29 |
| pyridalyl | 250 | 66 | 13 | 13 | 5 | 10 | 70 | 25 |
| flubendiamide | 250 | 66 | 13 | 5 | 41 | 10 | 67 | 18 |
| abamectin | 0.25 | 66 | 13 | 91 | 70 | 100 | 97 | 92 |
| pymetrozine | 1 | 66 | 13 | 28 | 86 | 38 | 75 | 38 |
| thiacloprid | 0.5 | 66 | 13 | 12 | 95 | 92 | 69 | 23 |
| novaluron | 250 | 66 | 13 | 7 | 68 | 59 | 68 | 19 |

* Expected based on calculation using the Colby equation.

Test C

For evaluating control of corn planthopper (*Peregrinus maidis*) through contact and/or systemic means, the test unit consisted of a small open container with a 3-4-day-old maize plant (spike) inside. White sand was added to the top of the soil prior to application. Test compounds and compositions were formulated, sprayed, and replicated three times as described for Test A. After spraying, the test units were allowed to dry for 1 h before they were post-infested with ~15-20 nymphs (18 to 21 day old) by sprinkling them onto the sand with a salt shaker. A black, screened cap was placed on the top of the cylinder. The test units were held for 6 days in a growth chamber at 22-24° C. and 50-70% relative humidity. Each test unit was then visually assessed for insect mortality.

The results calculated as mean averages of results from the three replicates are listed in Table C. Compound 123 was applied at a rate of 2.5 ppm. Compound 8 was applied at a rate of 0.2 ppm. The additional invertebrate pest control agent is designated as "Compound A" and was applied at the rates shown in Table C.

TABLE C

| | | Percent Mortality | | | | | | |
|---|---|---|---|---|---|---|---|---|
| | | Observed | | | | | Expected * | |
| Compound A | rate (ppm) | Cmpd 123 | Cmpd 8 | Cmpd A | Cmpd 123 + Cmpd A | Cmpd 8 + Cmpd A | Cmpd 123 + Cmpd A | Cmpd 8 + Cmpd A |
| thiamethoxam | 0.1 | 28 | 38 | 29 | 52 | 63 | 49 | 56 |
| buprofezin | 0.08 | 28 | 38 | 44 | 30 | 42 | 60 | 66 |

TABLE C-continued

|  |  | Percent Mortality | | | | | | |
|---|---|---|---|---|---|---|---|---|
|  |  | Observed | | | | | Expected * | |
| Compound A | rate (ppm) | Cmpd 123 | Cmpd 8 | Cmpd A | Cmpd 123 + Cmpd A | Cmpd 8 + Cmpd A | Cmpd 123 + Cmpd A | Cmpd 8 + Cmpd A |
| dinotefuran | 100 | 28 | 38 | 42 | 42 | 39 | 58 | 64 |
| chlorpyrifos | 250 | 28 | 38 | 48 | 69 | 54 | 62 | 68 |
| acetamiprid | 0.05 | 28 | 38 | 32 | 39 | 35 | 51 | 58 |
| oxamyl | 10.4 | 21 | 71 | 32 | 25 | 55 | 46 | 80 |
| spirotetramat | 75 | 21 | 71 | 65 | 84 | 83 | 72 | 90 |
| flonicamid | 10 | 21 | 71 | 70 | 67 | 78 | 76 | 91 |
| methomyl | 3.3 | 21 | 71 | 80 | 78 | 88 | 84 | 94 |
| lambda-cyhalothrin | 0.1 | 21 | 71 | 45 | 49 | 69 | 56 | 84 |
| indoxacarb | 250 | 8 | 8 | 21 | 44 | 55 | 28 | 27 |
| spinetoram | 25 | 8 | 8 | 58 | 71 | 45 | 62 | 62 |
| fipronil | 0.2 | 8 | 8 | 21 | 18 | 19 | 27 | 27 |
| pyriproxifen | 250 | 8 | 8 | 20 | 19 | 24 | 26 | 26 |
| thiodicarb | 10 | 8 | 8 | 64 | 61 | 70 | 67 | 66 |
| chlorfenapyr | 10 | 8 | 8 | 81 | 35 | 79 | 82 | 82 |
| chlorantraniliprole | 120 | 42 | 55 | 33 | 50 | 40 | 61 | 70 |
| cyantraniliprole | 5 | 42 | 55 | 67 | 31 | 67 | 81 | 85 |
| clothianidin | 0.1 | 42 | 55 | 35 | 79 | 88 | 62 | 71 |
| tolfenpyrad | 21 | 42 | 55 | 98 | 100 | 100 | 99 | 99 |
| cartap | 250 | 42 | 55 | 40 | 28 | 23 | 65 | 73 |
| methoxyfenozide | 250 | 42 | 55 | 33 | 15 | 23 | 61 | 70 |
| pyridalyl | 250 | 68 | 76 | 62 | 61 | 87 | 88 | 91 |
| flubendiamide | 250 | 68 | 76 | 42 | 76 | 62 | 81 | 86 |
| abamectin | 2.5 | 68 | 76 | 90 | 92 | 89 | 97 | 98 |
| pymetrozine | 1 | 68 | 76 | 76 | 100 | 95 | 92 | 94 |
| thiacloprid | 0.5 | 68 | 76 | 60 | 88 | 58 | 87 | 90 |
| novaluron | 250 | 68 | 76 | 51 | 81 | 65 | 84 | 88 |

* Expected based on calculation using the Colby equation.

Test D

For evaluating control of the Western Flower Thrip (*Frankliniellla occidentalis*) through contact and/or systemic means, the test unit consisted of a small open container with a 5-7-day-old Soleil bean plant inside.

Test compounds and compositions were formulated, sprayed, and replicated three times as described for Test A. After spraying, the test units were allowed to dry for 1 hour and then 22-27 adult thrips were added to the unit and then a black, screened cap was placed on top. The test units were held for 7 days at 25° C. and 45-55% relative humidity.

The results calculated as mean averages of results from the three replicates are listed in Table D. Compound 123 was applied at a rate of 25 ppm. Compound 8 was applied at a rate of 250 ppm. The additional invertebrate pest control agent is designated as "Compound A" and was applied at the rates shown in Table D.

TABLE D

|  |  | Plant Protection * | | | | | | |
|---|---|---|---|---|---|---|---|---|
|  |  | Observed | | | | | Expected ** | |
| Compound A | rate (ppm) | Cmpd 123 | Cmpd 8 | Cmpd A | Cmpd 123 + Cmpd A | Cmpd 8 + Cmpd A | Cmpd 123 + Cmpd A | Cmpd 8 + Cmpd A |
| thiamethoxam | 62.5 | 23 | 53 | 70 | 80 | 90 | 77 | 86 |
| buprofezin | 250 | 23 | 53 | 7 | 30 | 70 | 28 | 56 |
| dinotefuran | 0.05 | 23 | 53 | 70 | 90 | 90 | 77 | 86 |
| chlorpyrifos | 250 | 23 | 53 | 0 | 30 | 53 | 23 | 53 |
| acetamiprid | 100 | 23 | 53 | 43 | 53 | 70 | 56 | 73 |
| oxamyl | 250 | 30 | 37 | 13 | 37 | 30 | 39 | 45 |
| spirotetramat | 250 | 30 | 37 | 13 | 33 | 40 | 39 | 45 |
| flonicamid | 250 | 30 | 37 | 60 | 80 | 97 | 72 | 75 |
| methomyl | 40 | 30 | 37 | 40 | 77 | 77 | 58 | 62 |
| lambda-cyhalothrin | 250 | 30 | 37 | 30 | 77 | 83 | 51 | 56 |
| indoxacarb | 250 | 33 | 50 | 23 | 43 | 60 | 48 | 62 |
| spinetoram | 0.25 | 33 | 50 | 27 | 30 | 83 | 51 | 64 |
| fipronil | 0.2 | 33 | 50 | 17 | 10 | 77 | 44 | 59 |
| pyriproxifen | 250 | 33 | 50 | 7 | 40 | 73 | 38 | 54 |
| thiodicarb | 210 | 33 | 50 | 67 | 77 | 93 | 78 | 84 |
| chlorfenapyr | 20 | 33 | 50 | 70 | 97 | 100 | 80 | 85 |
| chlorantraniliprole | 240 | 3 | 10 | 3 | 20 | 37 | 6 | 13 |
| cyantraniliprole | 10 | 3 | 10 | 33 | 23 | 30 | 35 | 40 |
| clothianidin | 250 | 3 | 10 | 53 | 83 | 90 | 54 | 58 |
| tolfenpyrad | 210 | 3 | 10 | 37 | 30 | 77 | 39 | 43 |
| cartap | 250 | 3 | 10 | 7 | 7 | 13 | 10 | 16 |
| methoxyfenozide | 250 | 3 | 10 | 7 | 0 | 17 | 10 | 16 |

TABLE D-continued

|  |  | Plant Protection * | | | | | | |
|  |  | Observed | | | | | Expected ** | |
| Compound A | rate (ppm) | Cmpd 123 | Cmpd 8 | Cmpd A | Cmpd 123 + Cmpd A | Cmpd 8 + Cmpd A | Cmpd 123 + Cmpd A | Cmpd 8 + Cmpd A |
|---|---|---|---|---|---|---|---|---|
| pyridalyl | 50 | 40 | 30 | 60 | 70 | 57 | 76 | 72 |
| flubendiamide | 250 | 40 | 30 | 7 | 53 | 63 | 44 | 35 |
| abamectin | 1 | 40 | 30 | 20 | 37 | 60 | 52 | 44 |
| pymetrozine | 250 | 40 | 30 | 30 | 87 | 70 | 58 | 51 |
| thiacloprid | 250 | 40 | 30 | 27 | 67 | 60 | 56 | 49 |
| novaluron | 250 | 40 | 30 | 7 | 83 | 67 | 44 | 35 |

\* Plant Protection = (0 to 10 rating) × 10. Rating is on a scale of 0 to 10, 0 meaning no visible plant damage and 10 meaning complete plant damage.
\*\* Expected based on calculation using the Colby equation.

What is claimed is:
1. A compound that is selected from the group consisting of:
3-(2-chloro-6-fluorophenyl)-1-[(6-chloro-3-pyridinyl) methyl]-2-hydroxy-4-oxo-4H-pyrido[1,2-a]pyrimidinium inner salt;
1-[(2-chloro-5-thiazolyl)methyl]-3-(2-ethoxyphenyl)-2-hydroxy-4-oxo-4H-pyrido[1,2-a]pyrimidinium inner salt;
1-[(2-chloro-5-thiazolyl)methyl]-2-hydroxy-3-(3-methylphenyl)-4-oxo-4H-pyrido[1,2-a]pyrimidinium inner salt;
3-(3-chloro-2-fluorophenyl)-1-[(6-chloro-3-pyridinyl) methyl]-2-hydroxy-4-oxo-4H-pyrido[1,2-a]pyrimidinium inner salt;
2-hydroxy-4-oxo-1-(5-pyrimidinylmethyl)-3-[3-(trifluoromethyl)phenyl]-4H-pyrido[1,2-a]pyrimidinium inner salt;
1-[(2-chloro-5-thiazolyl)methyl]-2-hydroxy-4-oxo-3-(4'-(trifluoromethyl)[1,1'-biphenyl]-3-yl)-4H-pyrido[1,2-a]pyrimidinium inner salt;
1-[(2-chloro-5-thiazolyl)methyl]-3-(4'-fluoro[1,1'-biphenyl]-3-yl)-2-hydroxy-4-oxo-4H-pyrido[1,2-a]pyrimidinium inner salt; and
3-(5-chloro-2-fluorophenyl)-1-[(6-fluoro-3-pyridinyl) methyl]-2-hydroxy-4-oxo-4H-pyrido[1,2-a]pyrimidinium inner salt.

\* \* \* \* \*